United States Patent
Jara et al.

(10) Patent No.: US 11,375,918 B2
(45) Date of Patent: Jul. 5, 2022

(54) WHITE MATTER FIBROGRAPHY BY SYNTHETIC MAGNETIC RESONANCE IMAGING

(71) Applicants: BOSTON MEDICAL CENTER CORPORATION, Boston, MA (US); TRUSTEES OF BOSTON UNIVERSITY, Boston, MA (US)

(72) Inventors: Hernan Jara, Belmont, MA (US); Ryan McNaughton, Brookline, MA (US)

(73) Assignees: Boston Medical Center Corporation, Boston, MA (US); Trustees of Boston University, Boston, MA (US)

( * ) Notice: Subject to any disclaimer, the term of this patent is extended or adjusted under 35 U.S.C. 154(b) by 0 days.

(21) Appl. No.: 17/104,787

(22) Filed: Nov. 25, 2020

(65) Prior Publication Data

US 2021/0082113 A1 Mar. 18, 2021

Related U.S. Application Data

(63) Continuation-in-part of application No. PCT/US2019/034756, filed on May 30, 2019.
(Continued)

(51) Int. Cl.
*G01V 3/00* (2006.01)
*A61B 5/055* (2006.01)
(Continued)

(52) U.S. Cl.
CPC ............ *A61B 5/055* (2013.01); *A61B 5/0042* (2013.01); *G01R 33/4828* (2013.01);
(Continued)

(58) Field of Classification Search
CPC .............. G01R 33/543; G01R 33/5659; G01R 33/3415; G01R 33/36; A61B 5/055
(Continued)

(56) References Cited

U.S. PATENT DOCUMENTS

| 5,560,360 A | 10/1996 | Filler |
| 6,665,448 B1 | 12/2003 | Maurer |

(Continued)

FOREIGN PATENT DOCUMENTS

| WO | 2014/111266 A2 | 7/2014 |
| WO | 2015/031408 A1 | 3/2015 |
| WO | 2015057745 A1 | 4/2015 |

OTHER PUBLICATIONS

Basser PJ, Mattiello J, & LeBihan D (1994) Estimation of the effective self-diffusion tensor from the NMR spin echo. J. Magn Reson B 103(3):247-254.
(Continued)

*Primary Examiner* — Walter L Lindsay, Jr.
*Assistant Examiner* — Frederick Wenderoth
(74) *Attorney, Agent, or Firm* — Burns & Levinson LLP; Steven M. Mills

(57) ABSTRACT

Methods of characterizing the brain of a subject, comprising: (a) performing a multispectral multislice magnetic resonance scan on the brain of a subject, (b) storing image data indicative of a plurality of magnetic resonance weightings of each of a plurality of slices of the brain of the subject to provide directly acquired images, (c) processing the directly acquired images to generate a plurality of quantitative maps of the brain indicative of a plurality of qMRI parameters of the subject, (d) constructing a plurality of magnetic resonance images indicative of white matter structure from the quantitative maps, and (e) generating a spatial entropy map of the brain of the subject from the plurality of
(Continued)

magnetic resonance images; and/or generating a myelin water map of the brain of the subject from the plurality of magnetic resonance images.

19 Claims, 25 Drawing Sheets

Related U.S. Application Data

(60) Provisional application No. 62/678,725, filed on May 31, 2018.

(51) Int. Cl.

| | | |
|---|---|---|
| G01R 33/56 | (2006.01) | |
| A61B 5/00 | (2006.01) | |
| G01R 33/563 | (2006.01) | |
| G01R 33/48 | (2006.01) | |
| G01R 33/483 | (2006.01) | |
| G06T 7/00 | (2017.01) | |
| G06T 11/00 | (2006.01) | |
| G01R 33/50 | (2006.01) | |

(52) U.S. Cl.
CPC ..... *G01R 33/4835* (2013.01); *G01R 33/5602* (2013.01); *G01R 33/56341* (2013.01); *G06T 7/0012* (2013.01); *G06T 11/008* (2013.01); *A61B 5/4076* (2013.01); *A61B 2576/026* (2013.01); *G01R 33/50* (2013.01); *G01R 33/5608* (2013.01); *G06T 2207/10088* (2013.01); *G06T 2207/30016* (2013.01)

(58) Field of Classification Search
USPC .......................................................... 324/309
See application file for complete search history.

(56) References Cited

U.S. PATENT DOCUMENTS

| | | | |
|---|---|---|---|
| 7,298,143 | B2 | 11/2007 | Jaermann |
| 8,149,238 | B2 | 4/2012 | Buyanovskiy |
| 8,577,112 | B2 | 11/2013 | Mori |
| 8,781,197 | B2 | 7/2014 | Wang |
| 9,383,423 | B2 | 7/2016 | Liu |
| 9,436,869 | B2 | 9/2016 | Kim |
| 9,478,026 | B2 | 10/2016 | Jensen et al. |
| 9,568,580 | B2 | 2/2017 | Dale |
| 9,764,109 | B2 | 9/2017 | Brewer |
| 9,964,620 | B2 | 5/2018 | van Meel |
| 10,307,139 | B2 | 6/2019 | Boada |
| 10,324,154 | B2 | 6/2019 | Sperl |
| 2005/0212517 | A1 | 9/2005 | Jaermann |
| 2008/0119720 | A1 | 5/2008 | Carroll |
| 2008/0205733 | A1 | 8/2008 | Laidlaw |
| 2009/0137908 | A1* | 5/2009 | Patwardhan ......... A61B 5/0071 600/476 |
| 2009/0290770 | A1 | 11/2009 | Mori |
| 2010/0004527 | A1 | 1/2010 | Dale |
| 2010/0079140 | A1 | 4/2010 | Holthuizen |
| 2011/0044524 | A1 | 2/2011 | Wang |
| 2011/0170759 | A1 | 7/2011 | Bjornerud |
| 2012/0197105 | A1 | 8/2012 | Mezer |
| 2013/0004049 | A1 | 1/2013 | Weeden |
| 2013/0131438 | A1 | 5/2013 | Brewer |
| 2013/0221961 | A1* | 8/2013 | Liu .................. G01R 33/56545 324/307 |
| 2013/0249555 | A1 | 9/2013 | Chen |
| 2013/0289398 | A1* | 10/2013 | Borden .................. A61B 8/481 600/431 |
| 2014/0233819 | A1 | 8/2014 | Kim |
| 2015/0055845 | A1 | 2/2015 | Jensen |
| 2015/0073258 | A1 | 3/2015 | Mezer |
| 2015/0363951 | A1 | 12/2015 | Wedeen |
| 2016/0334489 | A1 | 11/2016 | Sperl |
| 2016/0343129 | A1 | 11/2016 | Novikov |
| 2017/0089997 | A1 | 3/2017 | Jara et al. |
| 2017/0220900 | A1 | 8/2017 | Boada |
| 2017/0236294 | A1 | 8/2017 | Fisher |
| 2018/0064902 | A1 | 3/2018 | Brewer |
| 2018/0089863 | A1* | 3/2018 | Marschner ......... G01R 33/5608 |
| 2018/0168500 | A1* | 6/2018 | Badeer ................. A61B 5/7278 |
| 2018/0286041 | A1 | 10/2018 | Hu |
| 2018/0321345 | A1* | 11/2018 | Van Den Brink .... G06T 11/003 |
| 2018/0329009 | A1 | 11/2018 | James |
| 2018/0344161 | A1 | 12/2018 | Meyer |
| 2019/0087978 | A1* | 3/2019 | Tourapis .................. G06T 9/00 |
| 2019/0310338 | A1 | 10/2019 | James |

OTHER PUBLICATIONS

Hernan Jara, et al., "White Matter Structure Revealed by Correlation-Time Diffusion Synthetic MRI: Age Effects," Abstract 2016.
Application No. PCT/US19/34756, filed May 30, 2019, for "White Matter Fibrography by Synthetic Magnetic Resonance Imaging," Hernan JARA.
International Search Report for Application No. PCT/US19/34756, dated Aug. 19, 2019.
Written Opinion for Application No. PCT/US19/34756, dated Aug. 19, 2019.
Sporns, O, Tononi G. & Kotter R. (2005) The human connectome: a structural description of the human brain. PLOS Computational Biology 1(4):e42.
Sotiropoulos SN & Zalesky A (2017) Building connectomes using diffusion MRI: why, how and but. NMR in Biomedicine:n/a-n/a.
Swanson LW & Lichtman JW (2016) From Cajal to connectome and beyond. Annual Review of Neuroscience 39(1):197-216.
Craddock RC, et al. (2013) Imaging human connectomes at the macroscale. Nat Meth 10(6):524-539.
Van Essen DC, et al. (2012) The Human Connectome Project: A data acquisition perspective. NeuroImage 62(4):2222-2231.
Assaf Y, et al. (2013) The CONNECT project: combining macro- and micro-structure. NeuroImage 80:272-282.
McNab JA, et al. (2013) The Human Connectome project and beyond: Initial applications of 300 mT/m gradients. NeuroImage 80:234-245.
Stejskal E & Tanner J (1965) Spin diffusion measurements: spin echoes in the presence of a time-dependent field gradient. Journal of Chemical Physics, vol. 42:288-292.
Merboldt KD, Hanicke W. & Frahm J (1985) Self-diffusion NMR imaging using stimulated echoes. Journal of Magnetic Resonance 64(3):479-486.
Taylor D & Bushell M (1985) The spatial mapping of translational diffusion coefficients by the NMR imaging technique. Physics in Medicine and Biology 30:345.
Wandell BA (2016) Clarifying human white matter. Annual Review of Neuroscience 39(1):103-128.
Riederer SJ, et al. (1984) Automated MR image synthesis: feasibility studies. Radiology 153(1):203-206.
Fatouros P. Marmarou A. Use of magnetic resonance imaging for in vivo measurements of water content in human brain: method and normal values. Journal of neurosurgery. 1999:90(1):109.
Jara H., Sakai O, Mankal P, Irving RP, Norbash AM. Multispectral quantitative magnetic resonance imaging of brain iron stores: a theoretical perspective. Top Magn Reson Imaging. 2006;17(1):19-30.
Thomas C. et al. (2014) Anatomical accuracy of brain connections derived from diffusion MRI tractography is inherently limited. Proceedings of the National Academy of Science 111(46):16574-16579.
Shawna Farquharson, et al (2013) White matter fiber tractography: why we need to move beyond DTI. Journal of neuroscience 118(6):1367-1377.
Jones DK, Knosche TR & Turner R (2013) White matter integrity, fiber count, and other fallacies: The do's and don'ts of diffusion MRI. Neuroimage 73:239-254.

(56) References Cited

OTHER PUBLICATIONS

Schindelin J, et al. (2012) Fiji: an open-source platform for biological-image analysis. Nature methods 9(7):676.
O'Muircheartaigh J. et al. (2014) White matter development and early cognition in babies and toddlers. Human Brain Mapping 15(9):4475-4487.
Le Bihan D & Johansen-Berg H (2012) Diffusion MRI at 25: exploring brain tissue structure and function. NeuroImage 61(2):324-341.
O'Donnell LJ & Pasternak O (2015) Does diffusion MRI tell us anything about the white matter? An overview of methods and pitfalls. Schizophrenia Research 161(1):133-141.
Fan Q et al. (2017) High b-value and High Resolution Integrated Diffusion (HIBRID) imaging. NeuroImage 150:162-176.
Torrey H. (1956) Bioch equations with diffusion terms. Physical Review, vol. 105(3):563-565.
Stejskal E (1965) Use of spin echoes in a pulsed magnetic-field gradient to study anisotropic restricted diffusion and flow. Journal of Chemical Physics, vol. 43:3597-3603.
Basser PJ, Mattielo J. & LeBihan D (1994) MR diffusion tensor spectroscopy and imaging. Biophys J 66(1):259-267.
Basser PJ & Pierpaoli C (1996) Microstructural and physiological features of tissues eludidated by quantitative-diffusion-tensor MRI. J. Magn Reson B 111(3):209-219.
Piepraoli C & Basser PJ (1996) Toward a quantitative assessment of diffusion anisotropy. Magn Reson Med 36 (6):893-906.
Piepraoli C, Jezzard P, Basser PJ, Barnett A, & Di Chiro G (1996) Diffusion tensor MR imaging of the human brain. Radiology 201(3):637-648.
Mattiello J, Basser PJ, & Le Bihan D (1997) The b matrix in diffusion tensor echo-planar imaging. Magn Reson Med 37 (2):292-300.
Basser P, Pajevic S, Pierpaoli C, Duda J, & Aldroubi A (2000) In vivo fiber tractography using DT-MRI data. Magnetic Resonance in Medicine 44(4):625-632.
Tuch DS, et al. (2002) High angular resolution diffusion imaging reveals intravoxel white matter fiber heterogeneity. Magnetic Resonance in Medicine 48(4):577-582.
Tuch DS (2004) Q-ball imaging. Magnetic Resonance in Medicine. 52(6):1358-1372.
Alexander DC (2005) Multiple-fiber reconstruction algorithms for diffusion MRI. Annals of the New York Academy of Sciences 1064(1):113-133.
Behrens TE, Berg HJ, Jbabdi S, Rushworth MF & Woolrich MW (2007) Probabilistic diffusion tractography with multiple fibre orientations. What can we gain? NeuoImage 34(1):144-155.
Jeurissen B, Leemans A, Jones DK, Tournier JD & Sijbers J (2011) Probabilistic fiber tracking using the residual bootstrap with constrained spherical deconvolution. Human brain mapping 32(3):461-479.
Mangin JF, et al. (2013) Toward global tractography. NeuroImage 80(Supplement C):290-296.
Feng L, et al. (2017) Compressed sensing for body MRI. Journal of Magnetic Resonance Imaging 45(4):966-987.
Barth M, Breuer F, Koopmans PJ, Norris DG, & Poser BA (2016) Simultaneous multislice (SMS) imaging techniques. Magnetic Resonance in Medicine 75(1):63-81.
Gagoski BA, et al. (2015) RARE/turbo spin echo imaging with simultaneous mutlislice Wave-CAIPI. Magnetic Resonance in Medicine 73(3):929-938.
MacKay AL & Laule C (2016) Magnetic resonance of myelin water: an in vivo marker for myelin. Brain Plasticity 2(1):71-91.
Labadie C, et al. (2014) Myelin water mapping by spatially regularized longitudinal relaxographic imaging at high magnetic fields. Magnetic Resonance in Medicine 71(1):375-387.
O'Shea TM, et al. (2009) The ELGAN study of the brain and related disorders in extremely low gestational age newborns. Early Human Development 85(11):719-725.
Joseph RM et al. (2016) Neurocognitive and academic outcomes at age 10 years of extremely preterm newborns. Pediatrics 137(4).
Hernan Jara et al., "High Spatial Resolution White Matter Fibrography (WMF): Technique Optimization," Abstract, 2017.
Hernan Jara, et al., "Connectome of the Extremely Preterm Brain at Adolescence Measures of Cognitive Functioning: Early Experience with White Matter Fibrography (WMF) and Latent Profile Analysis (LPA)," Abstract 2018.
Hernan Jara, et al., Connectome of the Extremely Preterm Brain at Adolescence Measures of Cognitive Functioning: Early Experience with White Matter Fibrography (WMF) Abstract 2017.
Ryan McNaughton, et al., "White matter fibrography of the extremely preterm brain: longitudinal connectome changes from childhood to adolescence," Abstract 2019.

\* cited by examiner

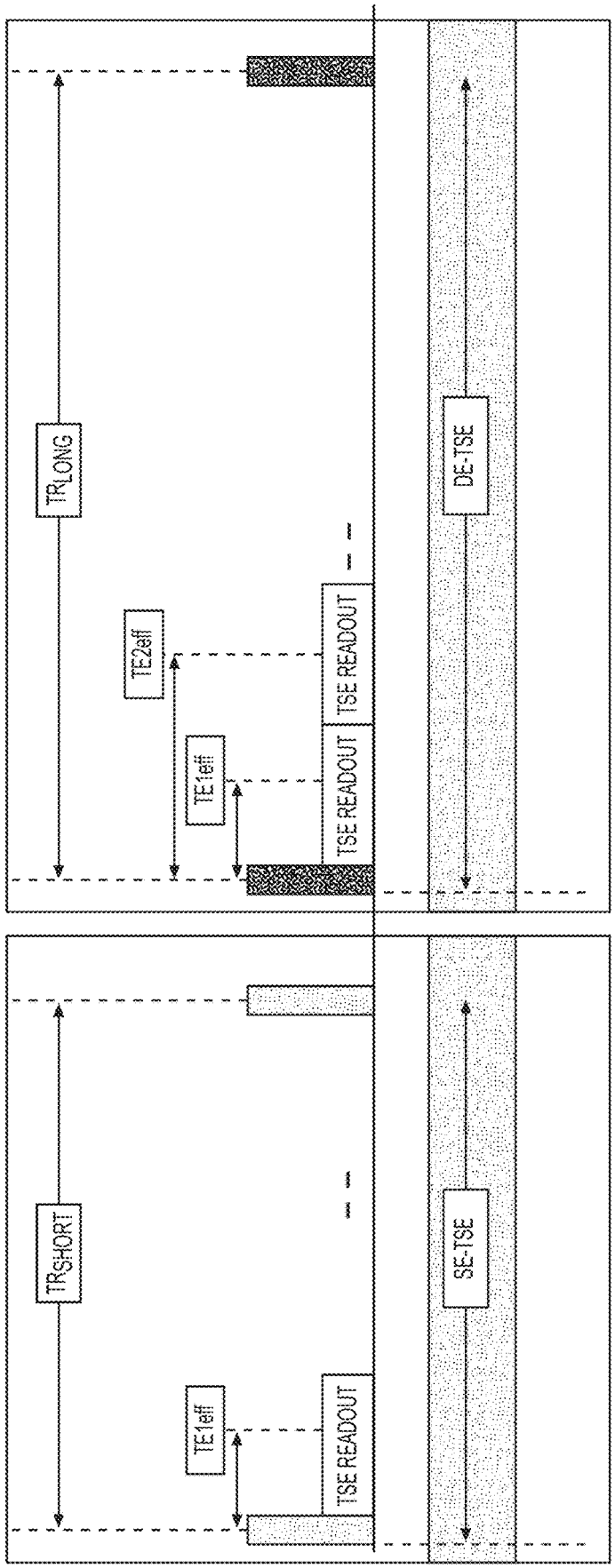
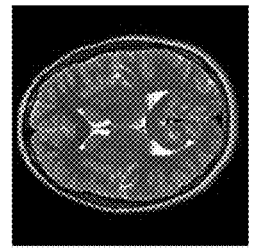
FIG. 4D
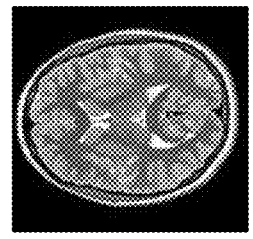
FIG. 4C
FIG. 4A
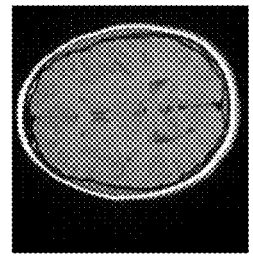
FIG. 4B

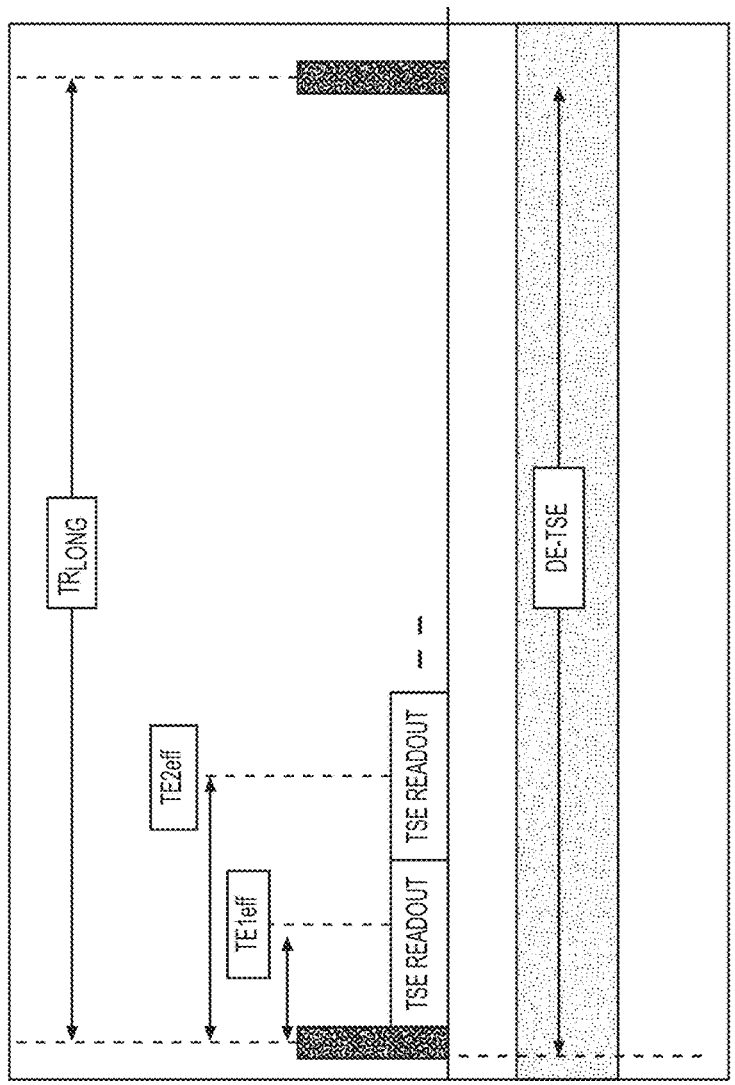
FIG. 5A
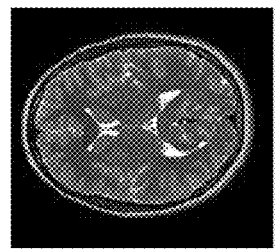
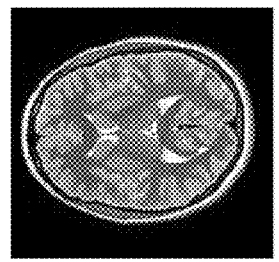
FIG. 5C
FIG. 5B

FEMALE 15YO (3T)
ENHANCED AND ISOTROPIC SPATIAL RESOLUTION
0.25 mm3

WHITE MATTER FIBROGRAPHY BY SYNTHETIC MAGNETIC RESONANCE IMAGING

GOVERNMENT FUNDING

This invention was made with Government support under Grant Nos. OD023348, NS040069 and HD018655 awarded by the National Institutes of Health. The Government has certain rights in the invention.

INTRODUCTION

The connectome concept was introduced in 2005 (1) to refer to a network inventory of the human brain that accounts for the totality of neural elements—neurons and synapses—as well as the axonal interconnections, which can be intrinsic to gray matter (GM) or extrinsic traversing white matter (WM) (2, 3). From the onset (1), connectome realizations were conceptualized at three progressively coarser neuro-structural scales, from the microscale of individual neurons and synapses, to the mesoscale of mini columns of neurons and their connection patterns, to the macroscale of brain regions and pathways.

A microscopic rendition of the human brain connectome through imaging would entail creating a comprehensive three-dimensional map of its neural connection matrix as sampled at sub-cellular spatial resolution of a voxel$\leq$(1 $\mu$m)$^3$. The creation of such microscopic connectomes in vivo, not currently possible, would have profound implications for understanding normal neurological function as well as for deciphering the complexities of neurologic disorders. Similarly, noninvasive in vivo connectome rendering at the mesoscale using voxel$\leq$(50 $\mu$m)$^3$ is also currently out of reach.

The more modest goal of creating in vivo macroscopic connectome renditions (4) at the coarser spatial resolution possible with current magnetic resonance imaging (MRI) technologies voxel$\geq$(500 $\mu$m)$^3$ could have far-reaching research and clinical implications provided that such connectome renditions are spatially accurate, reproducible, obtained with the short scan times needed for routine clinical workflow, and generated with standard configuration clinical equipment.

Diffusion MRI (dMRI) white matter tractography (WMT) is currently the only imaging technique described in the scientific literature for in vivo macroscopic connectomics. It has been adopted by large scale research initiatives such as the human connectome project (5, 6), which employs unique ultra-powerful imaging hardware (7). The defining technical feature of dMRI pulse sequences is the use of pulsed-field-gradient (PFG) technique for diffusion encoding (8-11). PFG diffusion encoding pulses are typically applied along numerous spatial directions—typically greater than 16—in order to generate sufficient experimental data as needed for modeling the geometrically intricate fiber orientation distribution functions (ODF) at each point. ODFs are intermediate mathematical objects used for tracing the streamlines—also known as estimated fascicles (12)—that are ultimately inferred as physical WM fibertracts.

There is a need in the art for alternative methods of making connectomes. There is also a need for algorithms, computational methods, and software for identifying, isolating, and manipulating mathematically and selectively the pixels of the fundamental white matter skeleton of the connectome. This disclosure meets this and other needs.

SUMMARY

This disclosure provides a conceptually different and likely complementary magnetic resonance imaging (MRI) technique for in vivo connectomics, referred to as white matter fibrography (WMF) in order to distinguish it from dMRI-WMT (FIG. 1).

At the image acquisition frontend, WMF is an application of multispectral quantitative MRI (MS-qMRI) scanning, which can use any of several MRI pulse sequences including mixed-TSE, multi-echo turbo spin echo with magnetization recovery (meTSEmr, FIG. 3), tri-TSE (FIGS. 4A to 4D), and DE-TSE (FIGS. 5A to 5C).

Post image acquisition WMF has at its core an MRI Synthesis mathematical algorithm (13) that is used for enhancing the subtle WM texture observed in maps of the longitudinal magnetization relaxation rate R1=1/T1 (see FIG. 2).

Alternatively, WMF can use an analogous qMRI parameter, specifically pseudoR1=1/pseudoT1, which can be mapped with a faster MRI scan; dual echo turbo spin echo (DE-TSE).

WMF uses model-free direct and deterministic image processing techniques at the backend; the image processing chain may include MS-qMRI algorithms for mapping R1, R2 and PD, an image synthesis engine for R1-weighting, a brain segmentation algorithm, as well as standard image sharpening filters, 3D-to-2D projection and 3D rendering techniques.

In the absence of a definite reference technique for in vivo connectomics (2, 14-16), this disclosure validates WMF by illustrating the defining organizational features and symmetry properties of normal connectomes, and by illustrating connectome alterations in the context of self-evident and independently confirmed pathology (acute ischemia), as well as more subtle organizational disorder possibly associated with impaired cognition. Accordingly, this disclosure demonstrates: 1) that WMF can be used to create realistic and symmetric connectome renditions using two MRI scanners of different manufacturers; 2) that WMF connectome development proceeds in a predictable pattern as a function of increasing age—range: 0.6-to-34 years-consistent with known developmental trajectory and patterns; 3) structural connectome alterations in areas of WM lesions following ischemic stroke detected by concurrent dMRI, and 4) diminished connectome order and/or symmetry in a prospectively studied cohort of adolescents born extremely preterm who have subnormal cognition.

The methods of this disclosure may be used for constructing white matter fibrograms with Synthetic MRI. Such methods allow for creating three-dimensional visual renditions of the human connectome with high spatial resolution and geometrical accuracy. These connectome renderings include highly complex visual information. This disclosure also provides methods of characterizing and quantifying of these connectomes. In certain embodiments computational methods for processing quantitatively and thus characterizing such connectome renditions in terms of fiber organization, order, and complexity via spatial entropy (SE) analysis are provided. Additionally, image processing methods for quantifying connectome tissue composition in terms of hydration (PD), and MR relaxometry of the longitudinal and transverse magnetizations R1=1/T1 and R2=1/T2 respectively are also provided.

This disclosure also provides algorithms, computational methods, and software for identifying, isolating, and manipulating mathematically and selectively the pixels of the fundamental white matter skeleton of the connectome. This is accomplished in certain embodiments by thresholding and binarizing the WMF images generated with R1-weighted synthetic MR, such that only the shortest T1 components are included. As shown in the subsequent parts of this disclosure, these data reduction methods enable the quantification of connectome information content measured in units of kBytes and measures of connectome water content via PD mapping. In turn, connectome-specific water content quantification enables a new technique for absolute myelin water imaging. This is accomplished by masking the PD calibrated maps with the binary mask of the connectome.

The following abbreviations and terminology are used herein. "Mixed-TSE" refers to mixed turbo spin echo, which is a multislice four time points multispectral quantitative MRI (MS-qMRI) scan. "TSE" and "FSE" stand for turbo spin echo or fast spin echo. "meTSEmr" stands for multi-echo turbo spin echo with magnetization recovery. "DE-TSE" stands for dual echo turbo spin echo. "Tri-TSE" stands for concatenation of a single echo TSE and a dual echo TSE sequences that are run consecutively without delay and with identical geometrical settings (voxel dimensions, field of view, and slice specifications: slice thickness and gap).

Thus, in an aspect this disclosure provides methods of making a white matter fibrogram representing the connectome of the brain of a subject. In some embodiments the methods comprise (a) performing a multispectral multislice magnetic resonance scan on the brain of a subject, (b) storing image data indicative of a plurality of magnetic resonance weightings of each of a plurality of slices of the brain of the subject to provide directly acquired images, (c) processing the directly acquired images to generate a plurality of quantitative maps of the brain indicative of a plurality of qMRI parameters of the subject, (d) constructing a plurality of magnetic resonance images indicative of white matter structure from the quantitative maps, and (e) rendering a white matter fibrogram of the brain of the subject from the plurality of magnetic resonance images.

In some embodiments the multispectral multislice magnetic resonance scan of (a) comprises performing a 2D scan. In some embodiments the 2D scan is a multispectral 2D scan. In some embodiments the multispectral 2D scan is selected from the group consisting of a 2D mixed-TSE scan, a 2D meTSEmr scan, 2D DE-TSE scan, and a 2D Tri-TSE scan.

In some embodiments the multispectral multislice magnetic resonance scan of (a) comprises performing a 3D scan. In some embodiments the 3D scan is a multispectral 3D scan. In some embodiments the multispectral 3D scan is selected from the group consisting of a 3D mixed-TSE scan, a 3D meTSEmr scan, a 3D DE-TSE scan, and a 3D Tri-TSE scan.

In some embodiments of the methods, (b) comprises storing the directly acquired images. In some embodiments the directly acquired images are stored in a location selected from a remote computer, a dedicated workstation, a smart device (phone or tablet), and a computer cloud.

In some embodiments of the methods (c) comprises processing the directly acquired images in an MRI scanner console, and/or (d) comprises processing the magnetic resonance images in an MRI scanner console, and/or (e) comprises processing the magnetic resonance images in an MRI scanner console.

In some embodiments of the methods (c) comprises processing the directly acquired images in a remote computer or dedicated workstation, and/or (d) comprises processing the magnetic resonance images in a remote computer or dedicated workstation, and/or (e) comprises processing the magnetic resonance images in a remote computer or dedicated workstation.

In some embodiments of the methods (c) comprises processing the directly acquired images in a smart device (phone or tablet), and/or (d) comprises processing the magnetic resonance images in a smart device (phone or tablet), and/or (e) comprises processing the magnetic resonance images in a smart device (phone or tablet).

In some embodiments of the methods (c) comprises processing the directly acquired images in a server in a computer cloud, and/or (d) comprises processing the magnetic resonance images in a server in a computer cloud, and/or (e) comprises processing the magnetic resonance images in a server in a computer cloud.

In some embodiments of the methods (d) comprises performing a synthetic MRI scan. In some embodiments of the synthetic MRI scan of (d) is selected from a synthetic MRI scan with quantitative R1 weighting, a synthetic MRI scan with quantitative pseudoR1 weighting, and a synthetic MRI scan with qualitative R1 weighting.

In some embodiments of the methods (c) comprises processing the directly acquired images with an image sharpening filter, and/or (d) comprises processing the magnetic resonance images with an image sharpening filter, and/or (e) comprises processing the magnetic resonance images with an image sharpening filter. In some embodiments the image sharpening filter is an unsharp mask filter or a deconvolution filter.

In some embodiments of the methods (e) comprises performing a 3D to 2D projection algorithm and the white matter fibrogram of (e) is a 3D to 2D projection image.

In some embodiments of the methods (e) comprises performing a 3D to 2D maximum intensity algorithm and the white matter fibrogram of (e) is a 3D to 2D maximum intensity projection.

In some embodiments of the methods comprises performing an algorithm selected from the group consisting of a volume rendering algorithm and a tractography algorithm.

In some embodiments of the methods (c) comprises processing a plurality of directly acquired images to generate qMRI maps portraying at least one of the T1, T2, and PD distributions at the native spatial resolution of the directly acquired images.

In some embodiments of the methods (c) comprises processing a plurality of directly acquired images to generate qMRI maps portraying at least one of the R1, R2, and PD distributions at the native spatial resolution of the directly acquired images.

In some embodiments of the methods (c) comprises processing a plurality of directly acquired images to generate synthetic MR images weighted by R1. In some embodiments the directly acquired images are processed with an algorithm comprising a relaxation rate weighting factor ($\Omega$) of from 0 Hz to 25 Hz. In some embodiments the algorithm comprises a relaxation rate weighting factor ($\Omega$) of from 0 Hz to 25 Hz, or from 10 Hz to 50 Hz, or from 15 Hz to 25 Hz, or from 5 Hz to 10 Hz, or from 10 Hz to 15 Hz, or from 15 Hz to 20 Hz, or from 20 Hz to 25 Hz, or from 4 Hz to 15 Hz.

In some embodiments of the methods (c) comprises processing a plurality of directly acquired images to generate synthetic MR images weighted by pseudoR1. In some embodiments the directly acquired images are processed with an algorithm comprising a relaxation rate weighting factor ($\Omega$) of from 0 Hz to 25 Hz. In some embodiments the algorithm comprises a relaxation rate weighting factor ($\Omega$) of from 0 Hz to 25 Hz, or from 10 Hz to 50 Hz, or from 15 Hz to 25 Hz, or from 5 Hz to 10 Hz, or from 10 Hz to 15 Hz, or from 15 Hz to 20 Hz, or from 20 Hz to 25 Hz, or from 4 Hz to 15 Hz.

Also provided are systems configured for making a white matter fibrogram representing the connectome of the brain of a subject. The methods may comprise: i) a magnetic resonance imaging machine configured to apply an external magnetic field and a plurality of excitation pulses to a subject in the magnetic resonance imaging machine; ii) a control system connected to the magnetic resonance imaging machine and configured to perform the method of claim 1; and iii) a computer processor configured to receive magnetic resonance image data and render a connectome from the data.

In another aspect this disclosure provides methods of characterizing the brain of a subject by generating a spatial entropy map of the brain of the subject from the plurality of magnetic resonance images; and/or generating a myelin water map of the brain of the subject from the plurality of magnetic resonance images. In some embodiments, the methods comprise (a) performing a multispectral multislice magnetic resonance scan on the brain of a subject, (b) storing image data indicative of a plurality of magnetic resonance weightings of each of a plurality of slices of the brain of the subject to provide directly acquired images, (c) processing the directly acquired images to generate a plurality of quantitative maps of the brain indicative of a plurality of qMRI parameters of the subject, (d) constructing a plurality of magnetic resonance images indicative of white matter structure from the quantitative maps, and (e) generating a spatial entropy map of the brain of the subject from the plurality of magnetic resonance images; and/or generating a myelin water map of the brain of the subject from the plurality of magnetic resonance images. In some embodiment, in e) only a spatial entropy map is generated. In some embodiment, in e) only a myelin water map is generated. In some embodiment, in e) both a spatial entropy map and a myelin water map are generated.

As used herein, an "integer disk radius" is a disk radius that is a whole number value i.e., 3 pixels, 4 pixels, or 5 pixels. A "disk radius" that is not expressly referred to as an integer disk radius is not necessarily a whole number.

In some embodiment, in e) the spatial entropy map is generated using an integer disk radius of from 2 to 6 pixels, from 3 to 5 pixels, or from 4 to 6 pixels. In some embodiments, in e) the spatial entropy map is generated using an integer disk radius of 4. In some embodiments, in e) the spatial entropy map is generated using disk radius of from 2.0 to 6.0, from 3.0 to 5.0, from 4.0 to 6.0, from 3.1 to 4.9, from 3.2 to 4.8, from 3.3 to 4.7, from 3.4 to 4.6, from 3.5 to 4.5, from 3.6 to 4.4, from 3.7 to 4.3, from 3.8 to 4.2, or from 3.9 to 4.1.

In some embodiments, the multispectral multislice magnetic resonance scan of (a) comprises performing a 2D scan. In some embodiments, the 2D scan is a multispectral 2D scan. In some embodiments, the multispectral 2D scan is selected from the group consisting of a 2D mixed-TSE scan, a 2D meTSEmr scan, 2D DE-TSE scan, and a 2D Tri-TSE scan.

In some embodiments, the multispectral multislice magnetic resonance scan of (a) comprises performing a 3D scan. In some embodiments, the 3D scan is a multispectral 3D scan. In some embodiments, the multispectral 3D scan is selected from the group consisting of a 3D mixed-TSE scan, a 3D meTSEmr scan, a 3D DE-TSE scan, and a 3D Tri-TSE scan.

In some embodiments, (b) comprises storing the directly acquired images. In some embodiments, the directly acquired images are stored in a location selected from a remote computer, a dedicated workstation, a smart device (phone or tablet), and a computer cloud.

In some embodiments, (c) comprises processing the directly acquired images in an MRI scanner console, and/or (d) comprises processing the magnetic resonance images in an MRI scanner console, and/or (e) comprises processing the magnetic resonance images in an MRI scanner console.

In some embodiments, (c) comprises processing the directly acquired images in a remote computer or dedicated workstation, and/or (d) comprises processing the magnetic resonance images in a remote computer or dedicated workstation, and/or (e) comprises processing the magnetic resonance images in a remote computer or dedicated workstation.

In some embodiments, (c) comprises processing the directly acquired images in a smart device (phone or tablet), and/or (d) comprises processing the magnetic resonance images in a smart device (phone or tablet), and/or (e) comprises processing the magnetic resonance images in a smart device (phone or tablet).

In some embodiments, (c) comprises processing the directly acquired images in a server in a computer cloud, and/or (d) comprises processing the magnetic resonance images in a server in a computer cloud, and/or (e) comprises processing the magnetic resonance images in a server in a computer cloud.

In some embodiments, (d) comprises performing a synthetic MRI scan. In some embodiments, the synthetic MRI scan of (d) is selected from a synthetic MRI scan with quantitative R1 weighting, a synthetic MRI scan with quantitative pseudoR1 weighting, and a synthetic MRI scan with qualitative R1 weighting.

In some embodiments, (c) comprises processing the directly acquired images with an image sharpening filter, and/or (d) comprises processing the magnetic resonance images with an image sharpening filter, and/or (e) comprises processing the magnetic resonance images with an image sharpening filter. In some embodiments, the image sharpening filter is an unsharp mask filter or a deconvolution filter.

In some embodiments, the myelin water mapping in (e) comprises thresholding R1-weighted synthetic images to isolate large signal pixels, which correlate with short T1 components of the white matter.

In some embodiments, the myelin water mapping in (e) comprises performing thresholding, binarization, and masking of a PD map to reveal the skeleton of the axon fiber network corresponding to the water trapping within the myelin sheath.

In some embodiments, (e) comprises performing an algorithm selected from the group consisting of calculating anatomically localized spatial entropy measures, global spatial entropy measures, anatomically localized myelin water measures, and/or global myelin water measures.

In some embodiments, (c) comprises processing a plurality of directly acquired images to generate qMRI maps portraying at least one of the T1, T2, and PD distributions at the native spatial resolution of the directly acquired images.

In some embodiments, (c) comprises processing a plurality of directly acquired images to generate qMRI maps portraying at least one of the R1, R2, and PD distributions at the native spatial resolution of the directly acquired images.

In some embodiments of the methods (c) comprises processing a plurality of directly acquired images to generate synthetic MR images weighted by R1. In some embodiments the directly acquired images are processed with an algorithm comprising a relaxation rate weighting factor ($\Omega$) of from 0 Hz to 25 Hz. In some embodiments the algorithm comprises a relaxation rate weighting factor ($\Omega$) of from 0 Hz to 25 Hz, or from 10 Hz to 50 Hz, or from 15 Hz to 25 Hz, or from 5 Hz to 10 Hz, or from 10 Hz to 15 Hz, or from 15 Hz to 20 Hz, or from 20 Hz to 25 Hz, or from 4 Hz to 15 Hz.

In some embodiments of the methods (c) comprises processing a plurality of directly acquired images to generate synthetic MR images weighted by pseudoR1. In some embodiments the directly acquired images are processed with an algorithm comprising a relaxation rate weighting factor ($\Omega$) of from 0 Hz to 25 Hz. In some embodiments the algorithm comprises a relaxation rate weighting factor ($\Omega$) of from 0 Hz to 25 Hz, or from 10 Hz to 50 Hz, or from 15 Hz to 25 Hz, or from 5 Hz to 10 Hz, or from 10 Hz to 15 Hz, or from 15 Hz to 20 Hz, or from 20 Hz to 25 Hz, or from 4 Hz to 15 Hz.

In some embodiments, the methods further comprise determining the total spatial entropy content of the brain of the subject. In some embodiments the methods further comprise comparing the total entropy of the brain of the subject to a total entropy standard of a defined subject parameter. In some embodiments, the defined subject parameter is one or a combination of any two or more of age, gender, ethnicity, cognition status, state of physical health, and state of mental health. In some embodiments, the total entropy measured for the subject is higher than the total entropy standard for the defined subject parameter and the subject is determined to have a condition correlated to the parameter. In some embodiments, the total entropy measured for the subject is lower than the total entropy standard for the defined subject parameter and the subject is determined to not have a condition correlated to the parameter.

Also provided are systems configured for characterizing the brain of a subject by generating a spatial entropy map of the brain of the subject from the plurality of magnetic resonance images; and/or generating a myelin water map of the brain of the subject from the plurality of magnetic resonance images. In some embodiments the systems comprise: i) a magnetic resonance imaging machine configured to apply an external magnetic field and a plurality of excitation pulses to a subject in the magnetic resonance imaging machine; ii) a control system connected to the magnetic resonance imaging machine and configured to perform the method of characterizing the brain of a subject by generating a spatial entropy map of the brain of the subject from the plurality of magnetic resonance images; and/or generating a myelin water map of the brain of the subject from the plurality of magnetic resonance images; and iii) a computer processor configured to receive magnetic resonance image data and render a connectome from the data.

BRIEF DESCRIPTION OF THE DRAWINGS

FIGS. 4A to 4D show a tri-TSE magnetic resonance imaging pulse sequence timing diagram and representative directly acquired images. (A) tri-TSE magnetic resonance imaging pulse sequence timing diagram. (B) T1-weighted directly acquired image, (C) PD-weighted directly acquired image, and (D) T2-weighted directly acquired image, in accordance with an implementation of the invention as described herein.

FIGS. 5A to 5C show a dual echo magnetic resonance pulse sequence timing diagram and representative directly acquired images. (A) a dual echo magnetic resonance pulse sequence timing diagram. (B) PD-weighted directly acquired image, (C) T2-weighted directly acquired image, in accordance with the pseudo-R1 implementation as described herein.

DETAILED DESCRIPTION

To provide a general understanding of the systems and methods described herein, certain illustrative embodiments will now be described. However, it will be understood that the systems and methods described herein may be adapted and modified as is appropriate for the application being addressed and that the systems and methods described herein may be employed in other suitable applications, and that such other additions and modifications will not depart from the scope thereof. In particular, a computerized control system, computer, processor, smartphone, tablet, or server in a cloud as used in this description may be a single computing device or multiple computing devices working collectively and in which the storage of data and the execution of functions are spread out amongst the various computing devices.

A. Introduction

Diffusion-MRI white matter tractography (dMRI-WMT) is currently the only technique available for in vivo mapping the neural connections of the human brain. This disclosure provides a fundamentally different technique for MRI based connectomics that is referred to herein as white matter fibrography (WMF). WMF is a direct connectome rendering technique which is an application of multispectral quantitative MRI (MS-qMRI) and Synthetic-MRI (FIG. 1). WM has a smooth continuous tissue appearance in most MR images, however it can exhibit an irregular, well defined but subtle graininess in qMRI maps of the longitudinal relaxation rate R1 (see FIGS. 6 and 7 for examples at 1.5 T and 3 T). The hypotheses of this disclosure are that 1) Synthetic-MRI with R1 weighting can be used to enhance the WM texture observed on the R1 maps or alternatively pseudoR1 maps to a contrast level that is sufficient for unravelling and visualizing the architectural framework of the underlying WM fiber matrix (myelin water), and 2) that the texture-enhanced images derived from synthetic-MRI with R1 weighting can be used for creating a connectome rendition using standard and direct image processing techniques (i.e., image sharpening filters, 3D rendering and 3D-to-2D projection techniques).

FIG. 1 shows the two different approaches for brain connectomics: DTI and WMF. The left panel shows a diffusion encoded spin echo echoplanar pulse sequence as well as a tractogram example. The right panel depicts the WMF image processing pipeline as well as a fibrogram example.

Figure 1B:
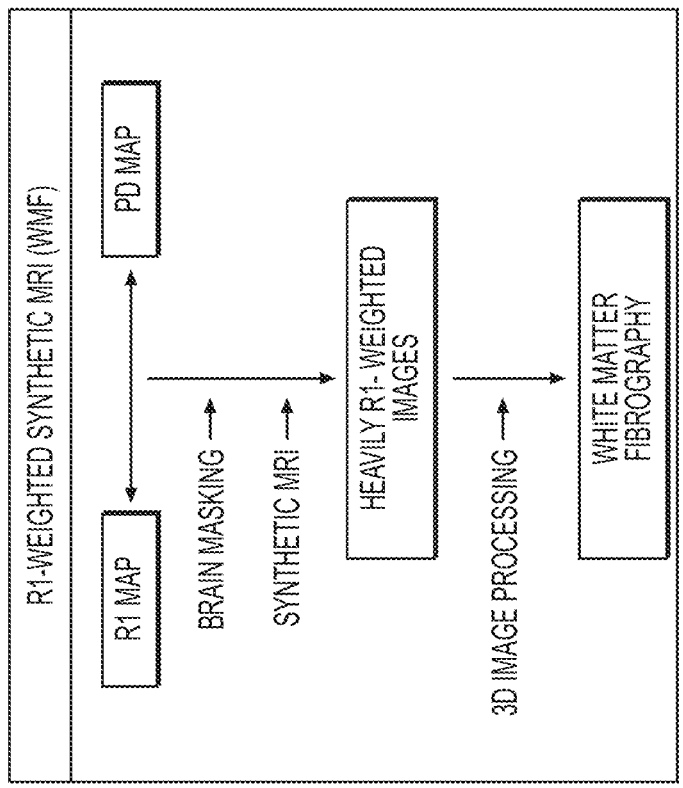
FIGS. 1A and 1B show operational principles of diffusion tensor imaging (DTI) tractography in comparison with those of white matter fibrography (WMF). (A) the general operational principles of diffusion-based MRI diffusion tensor imaging (DTI) tractography. (B) the general operational principles of white matter fibrography (WMF), which is the object of this invention. DTI tractography uses the pulsed-field-gradient (PFG) diffusion encoding method (left panel) and WMF uses non-diffusion encoded pulse sequences. Furthermore, WMF uses qMRI algorithms to generate maps of the proton density (PD) and the longitudinal magnetization rate (R1). The PD and/or R1 maps are multiplied by a mask of the brain on a slice by slice basis in order to eliminate signals from the extracranial tissues. The masked PD and R1 maps are further processed with a synthetic-MRI algorithm (using Eq. 1) to generate heavily R1-weighted images descriptive of the underlying structure of white matter matrix of each slice.
Figure 1B:
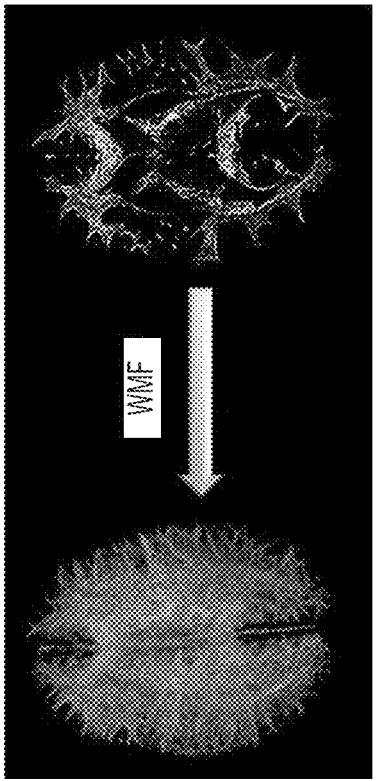
Figure 1A:
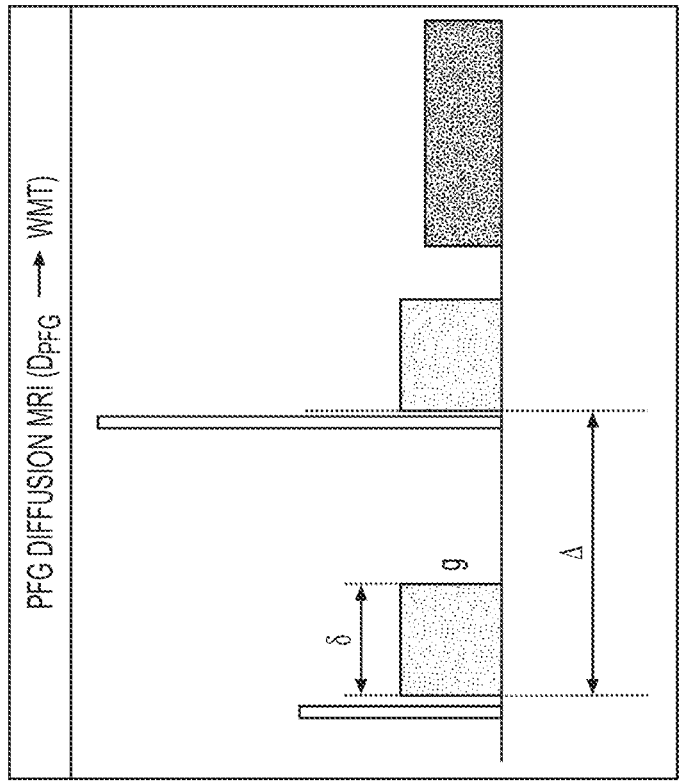
Figure 1A:
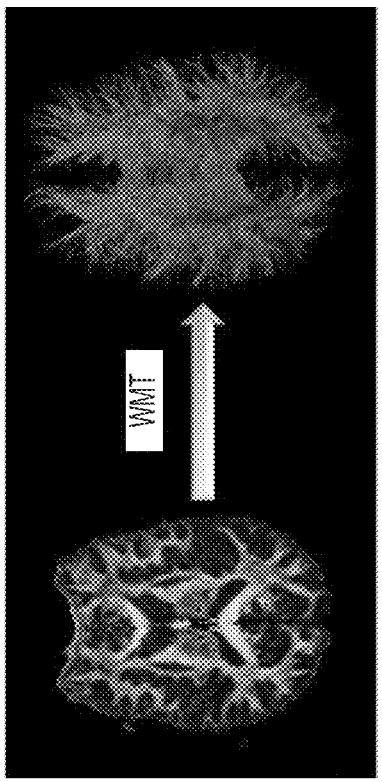
Figure 2:
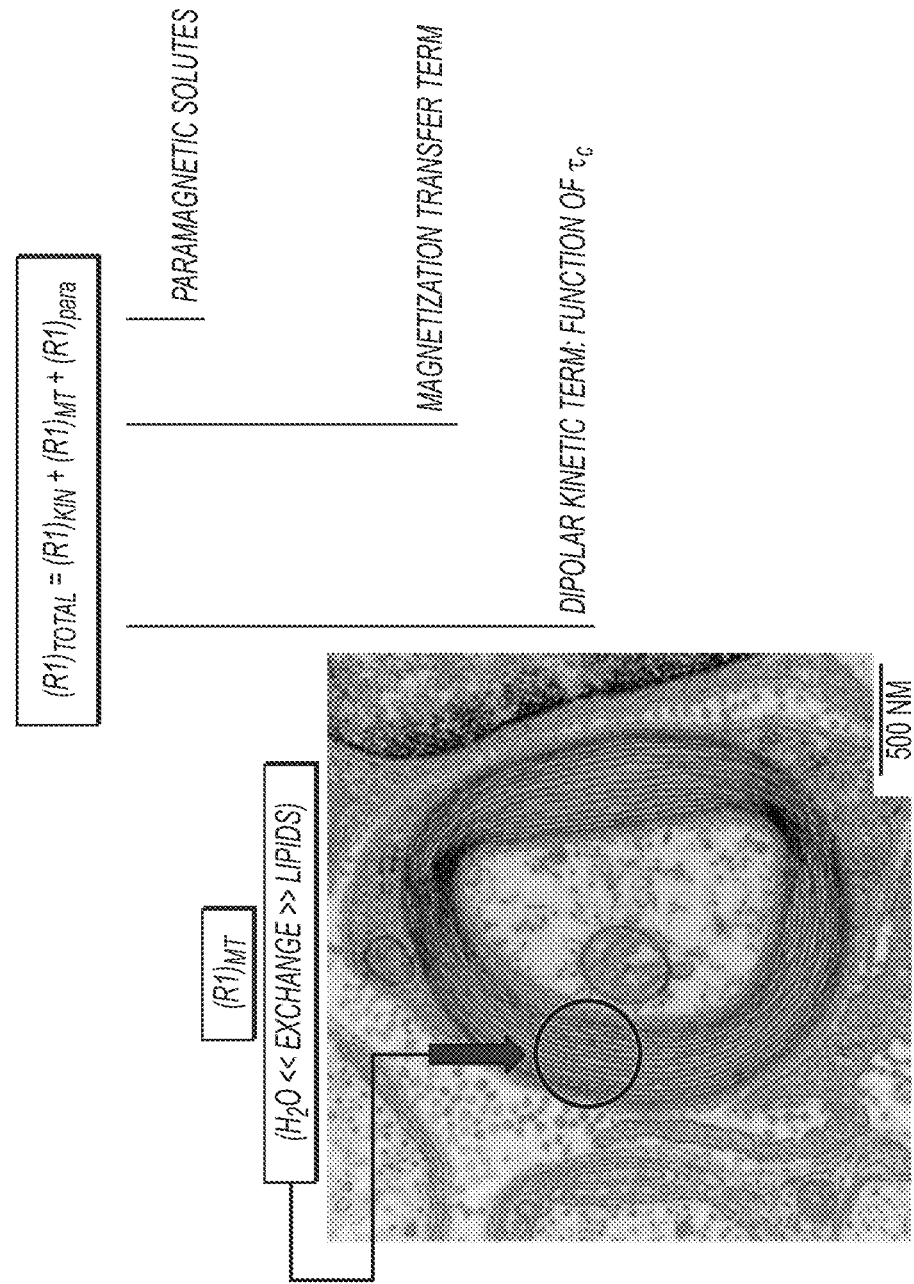
FIG. 2 shows the theoretical underpinnings of the longitudinal relaxation rate (R1) of white matter, the central physical principle in accordance with an implementation as described herein.

FIG. 2 shows the theoretical underpinnings of WMF, whereby the main weighting parameter—specifically the longitudinal magnetization relaxation rate R1—is given in a formula which is the sum of the three major contributions: 1) the dipolar kinetic term, 2) the magnetization transfer term (MT), and a paramagnetic solute term. The largest term in WM is the MT term associated with the 1H-protons of myelin and therefore, the MRI signals of these slow moving and exchange myelin protons are dominant in the extremely R1-weighted regime based on the equation: $Synth_{MRI} = PD \exp[-\Omega/R1]$ where $\Omega$ is an adjustable parameter, the optimum range of which is determined by computer simulation, as shown later herein.

In the absence of definite reference standard for in vivo connectomics, this disclosure validates WMF by illustrating the defining organizational features and symmetry properties of normal connectomes as a function of age, and by demonstrating connectome alterations in the context of self-evident and independently confirmed pathology—acute ischemic stroke—, as well as less obvious organizational connectome disorder, possibly associated with impaired cognition.

The data presented in the Examples demonstrates that WMF is a promising complementary alternative to dMRI-WMT for in vivo connectomics, which can generate undistorted high spatial resolution connectomes in clinically feasible scan times (<10 min) using standard clinical MRI hardware. The examples demonstrate the utility of the invention for the assessment of WM disease and for improving preoperative surgical planning, and building ultrahigh spatial resolution connectomes.

Creating in vivo connectome renditions routinely in the clinic can have far-reaching medical and scientific implications. The described WMF technique bridges a technological gap because the maximum spatial resolution achievable is not hampered by the mathematical and technical requirements associated with diffusion encoded MRI. WMF is promising because it is clinically practical, direct, geometrically accurate, and self-evident.

B. Magnetic Resonance Imaging Pulse Sequences

Figure 3:
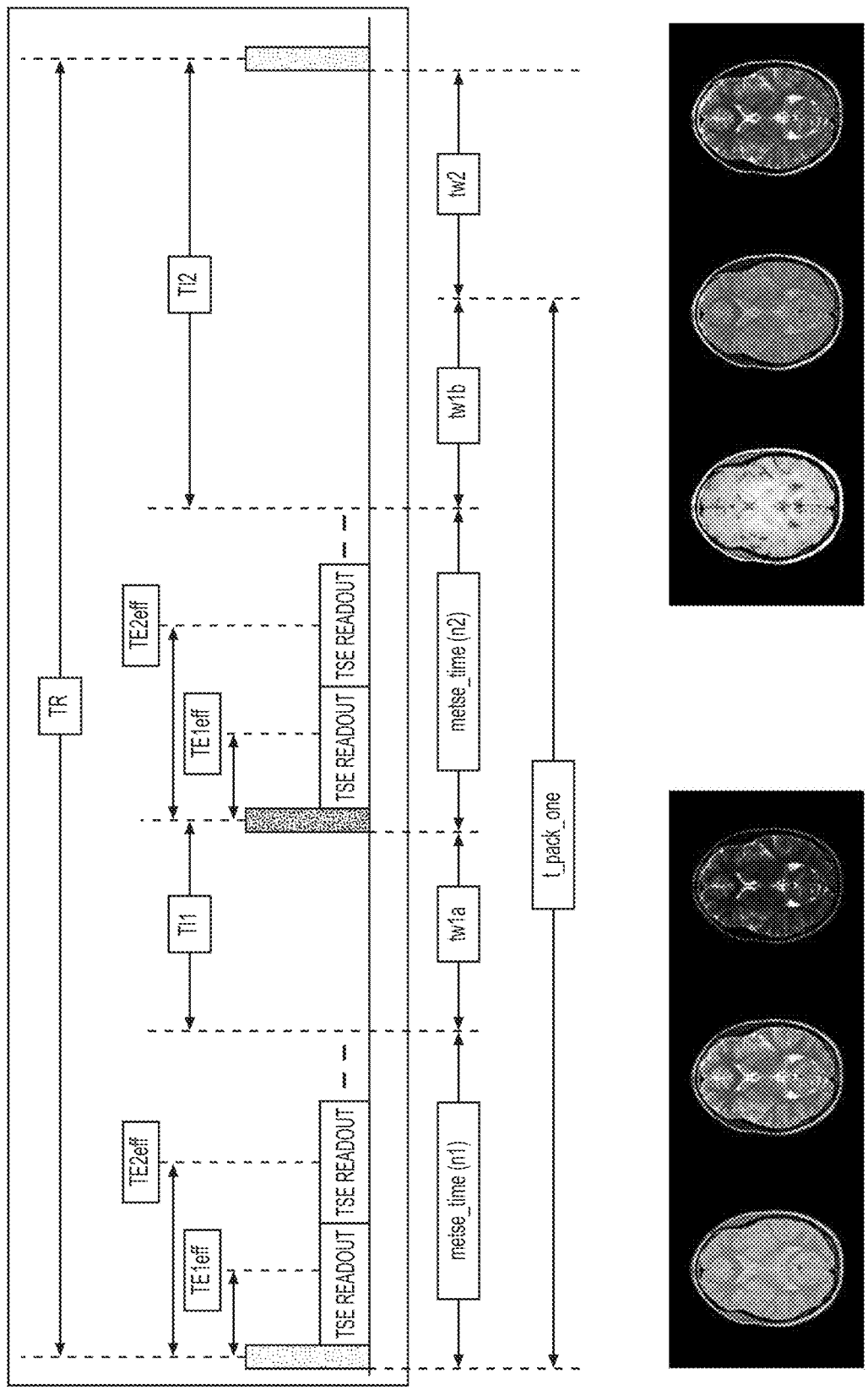
FIG. 3 shows a multi-echo TSE with magnetization recovery (meTSEmr) magnetic resonance imaging pulse sequence timing diagram, in accordance with an implementation of the invention as described herein.

Aspects of the methods described herein comprise use of two dimensional (2D-) MRI pulse sequences capable of generating coregistered PD and R1 maps, with either partial magnetization recovery (multislice multi-echo MS-meTSEmr in FIG. 3), or with magnetization saturation (Tri-TSE in FIGS. 4A to 4D), or with PD analytical conversion to R1 (DE-TSE in FIGS. 5A to 5C) and the use of such pulse sequences to obtain a plurality of magnetic resonance images of a subject.

Aspects of the methods described herein comprise use of three dimensional (3D-) MRI pulse sequences capable of generating coregistered PD and R1 maps, with either partial magnetization recovery (multi-echo MS-meTSEmr in FIG. 3), or with magnetization saturation (Tri-TSE in FIGS. 4A to 4E), or with PD analytical conversion to R1 (DE-TSE in FIGS. 5A to 5C) and the use of such pulse sequences to obtain a plurality of magnetic resonance images of a subject.

The timing diagram core module of the meTSEmr pulse sequence is as follows (see FIG. 3): the pulse sequence has several multi-echo readouts (TE1eff, TE2eff, TE3eff, etc.) and two longitudinal magnetization recovery times (TI1 and TI2). For each of the two excitation pulses there are several (1, 2, n) hybrid readouts, which can be of any of the three types: turbo (fast) spin echo (TSE), gradient and spin echo (GraSE) or gradient echoes only (EPI). In this way, the pulse sequence enables the computation of 1) T1 maps by differential T1-weighting, 2) T2 (T2*) maps by differential T2 (T2*)-weighting, 3) proton density (PD) maps by weighting inversion and pixel auto-calibration, and 4) diffusion coefficient by correlation time theory. The meTSEmr—with hybrid readouts pulse sequence is compatible with parallel imaging (SENSE, ASSET), other acceleration methods (compressed sensing) and could be implemented in multi-slice 2D mode, multi-slab 3D mode, or in full 3D mode. The pulse sequence begins with an RF excitation pulse followed by one or several hybrid readouts then there is a longitudinal magnetization recovery time (TI1) during which other slices are excited and interrogated, then a second excitation RF pulse followed by one or several hybrid readouts are played out. This is followed by a second longitudinal recovery time (TI2) during which other slices are interrogated. The hybrid readouts of the two measurement periods may or may not be identical. In one possible implementation of this pulse sequence the RF excitation pulses are both 90 degree pulses and the there are three hybrid readouts after each RF excitation pulse.

The timing diagram of the Tri-TSE pulse sequence (see FIG. 4A) shows the concatenation of a single echo TSE and a dual echo TSE sequences that are run consecutively without delay and with identical geometrical settings (voxel dimensions, field of view, and slice specifications: slice thickness and gap). In some embodiments of this invention, the scanning order is SE-TSE+DE-TSE or alternatively DE-TSE+SE-TSE, for example.

In certain embodiments the simplest and/or fastest pulse sequence that can be used for WMF as pertaining to this invention is the DE-TSE pulse sequence (see FIGS. 5A to 5C) implemented in the unsaturated regime, specifically TR>T1 of gray matter. In this case, PD can be mapped accurately by inverting the T2 decay at each pixel and proceeding to map pseudoR1 with the experimental equations derived by Fatouros and Marmarou (14), specifically $$R1 = \frac{1}{B} \cdot \left(\frac{1}{PD} - A\right).$$

In these equations A and B are parameters that depend on the main magnetic field strength B0. These can be fitted from the experimental data of Fatouros and Marmarou paper to give: $A=-0.002*B0^2-0.023*B0+0.96$ and $B=-0.004*B0^2+0.106*B0+0.173$.

C. White Matter Fibrography (WMF)

The magnetic resonance images used for WMF processing may be directly acquired images or quantitative maps and in addition may be multispectral—that is, more than one magnetic resonance image parameter may be mapped from a single pulse sequence. One or more of the tissue parameters influence the contrasts of these magnetic resonance images. Such parameters include any of the following: the longitudinal magnetization relaxation time T1, the longitudinal magnetization relaxation rate R1, the transverse magnetization relaxation time T2, the transverse magnetization relaxation rate R2, the reduced transverse magnetization relaxation time T2*, the proton density (PD), and the diffusion coefficient.

Figure 6:
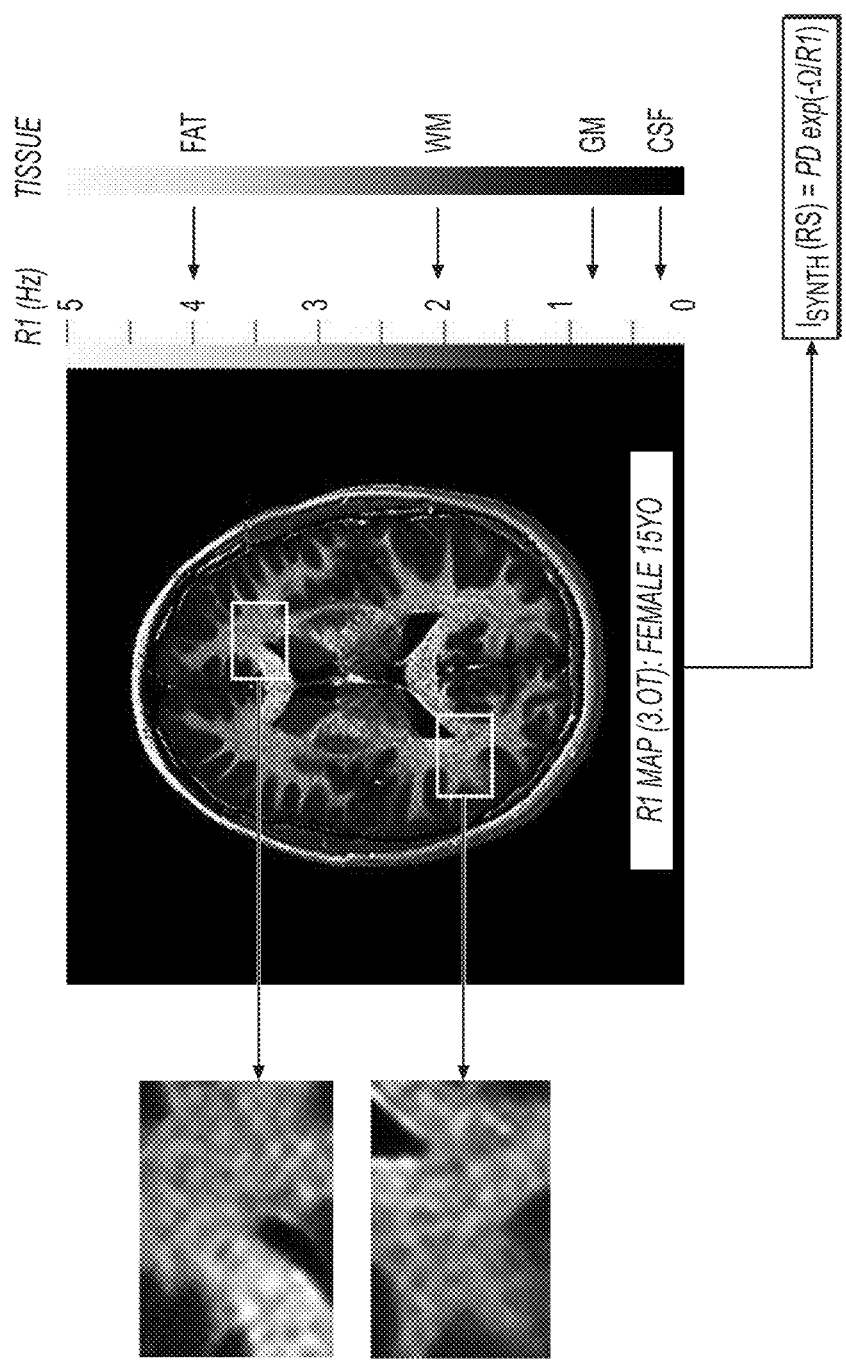
FIG. 6 shows a quantitative R1 map exhibiting the subtle white matter texture which is enhanced by synthetic MRI; in accordance with the main invention principle as described herein.
Figure 7:
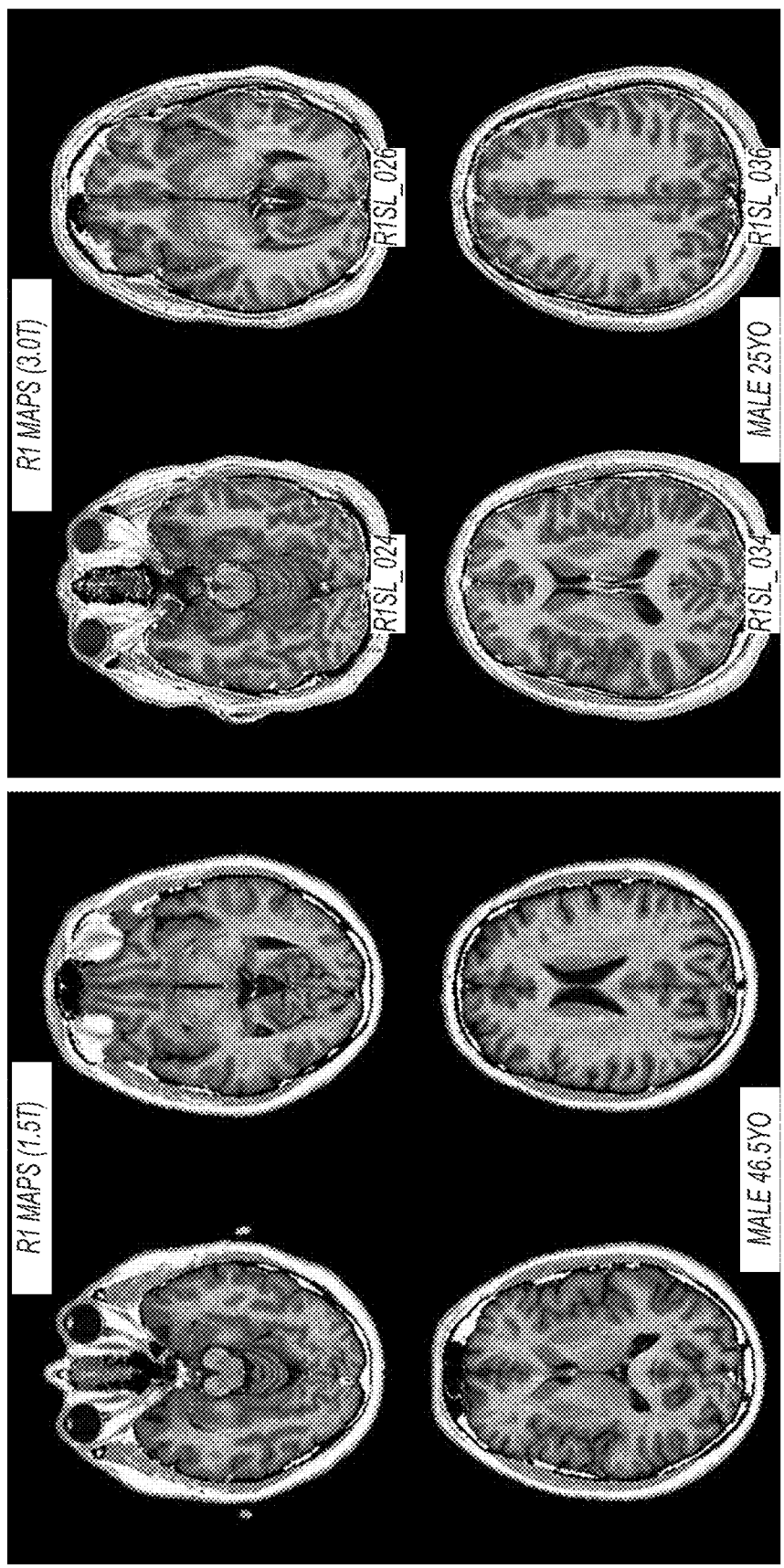
FIG. 7 shows additional examples of quantitative MRI maps obtained with 1.5 T and 3.0 T MRI scanners showing the subtle white matter texture Selected R1 maps of two male healthy volunteers scanned at 1.5 T (left) and 3.0 T (right) respectively showing subtle but clearly perceptible WM graininess. The WMF technique described in this work uses R1-weighted Synthetic MRI (see Eq. 1) to accentuate this texture thus allowing to ultimately extract the underlying WM matrix, as discussed in the text; in accordance with the main invention principle as described herein.

The longitudinal magnetization relaxation rate R1 (=1/T1) of brain tissue includes three distinct physical phenomena depending on the location and microscopic environment of the 1H-protons (FIG. 2). Specifically, the total R1 relaxation rate can be well described as the sum of three terms (see equation in FIG. 1): a kinetic term, a magnetization transfer term, and a paramagnetic term. The kinetic term represents the dipolar 1H-to-1H dipolar interactions between protons of the same water molecule (intramolecular interactions) as well as the intermolecular interactions between 1H protons of different water molecules. Dipolar interactions are characterized by the so-called correlation time (tau), which is similar in magnitude for rotational and translational micro-motions. These dipolar interactions are the main cause for R1-relaxation in most locations of brain tissue where magnetization transfer effects are weak (e.g. gray matter (GM) and non-myelin water. Water within the myelin sheaths however has motional restrictions and in addition exchanges with hydration water which is nearly immobile thus leading to a faster magnetization transfer R1 relaxation rate, designated above by $R1_{MT}$. This MT-R1 term is at the heart of the WMF invention described herein. As shown in FIGS. 6 and 7 quantitative R1 maps show a subtle texture in WM. The central idea of the invention reported herein is that by using heavily R1-weighted synthetic pulse sequences, it is possible render directly the geometrical shape of the white matter fiber bundles because only the myelin protons contribute to the synthetic MR signals. Such R1-weighted pulse sequences may be difficult to implement in actual (physical) MRI scanners but in the context of this disclosure it may be, in certain embodiments, straightforward in virtual MRI scanners. The third paramagnetic R1 term is in general very small and caused by dissolved molecular oxygen. Additionally, the key quantitative parameter of this invention, specifically R1 can also be estimated for brain tissues using the formulas established empirically by Fatouros et al. 14); we shall refer to this derived parameter as pseudoR1=(1/PD−B)/A where PD is the proton density and the coefficients (A and B) depend on the strength of the main magnetic field B0 to be used instead of the true-R1 maps for generating connectome renditions via synthetic-MRI. These aspects form a physical basis for certain embodiments of this disclosure.

Figure 8:
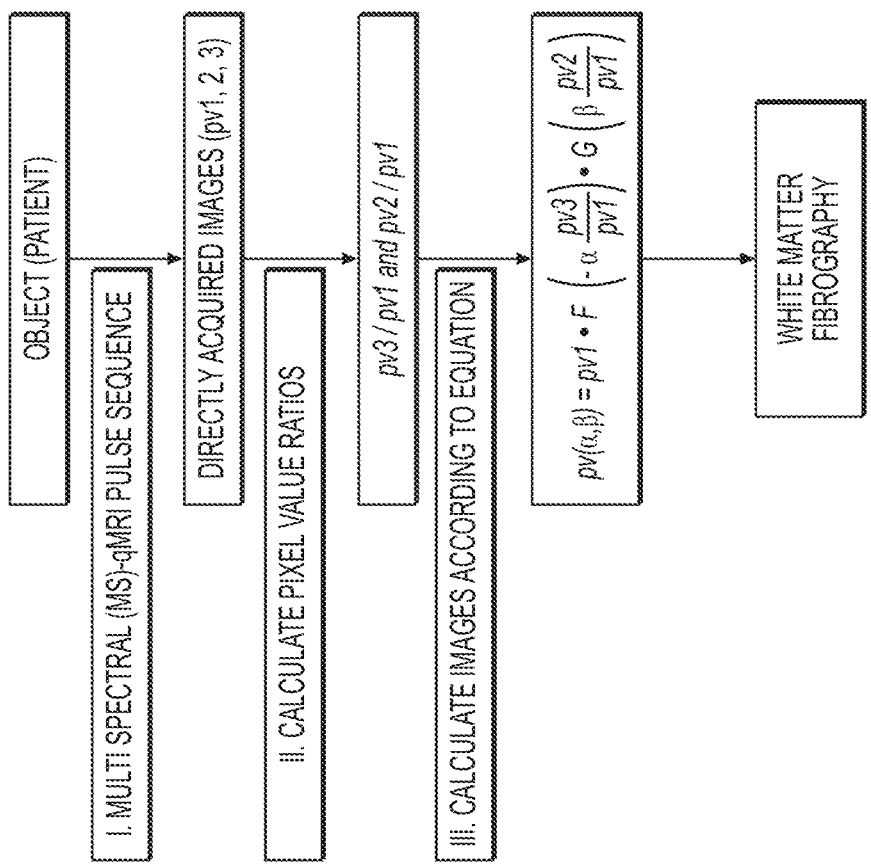
FIG. 8 shows a flow chart describing the general method for WMF; in accordance with an implementation as described herein.

In a first embodiment, a general white matter fibrogram (WMF) generating algorithm is used to generate a connectome for the brain of a subject. A flow chart representative of the embodiment is shown in FIG. 8 (Method 1: General pixel-value-ratio algorithm). A plurality of differently weighted MR images (pv1, pv2, pv3) are acquired with a single or multiple pulse sequences, a WM fibrogram may then be generated by calculating the pixel value ratios (pv3/pv1 and pv2/pv1) and using these ratios as arguments to the functions F and G, which have adjustable parameters α and β, respectively. F and G can be any smooth mathematical functions.

Figure 9:
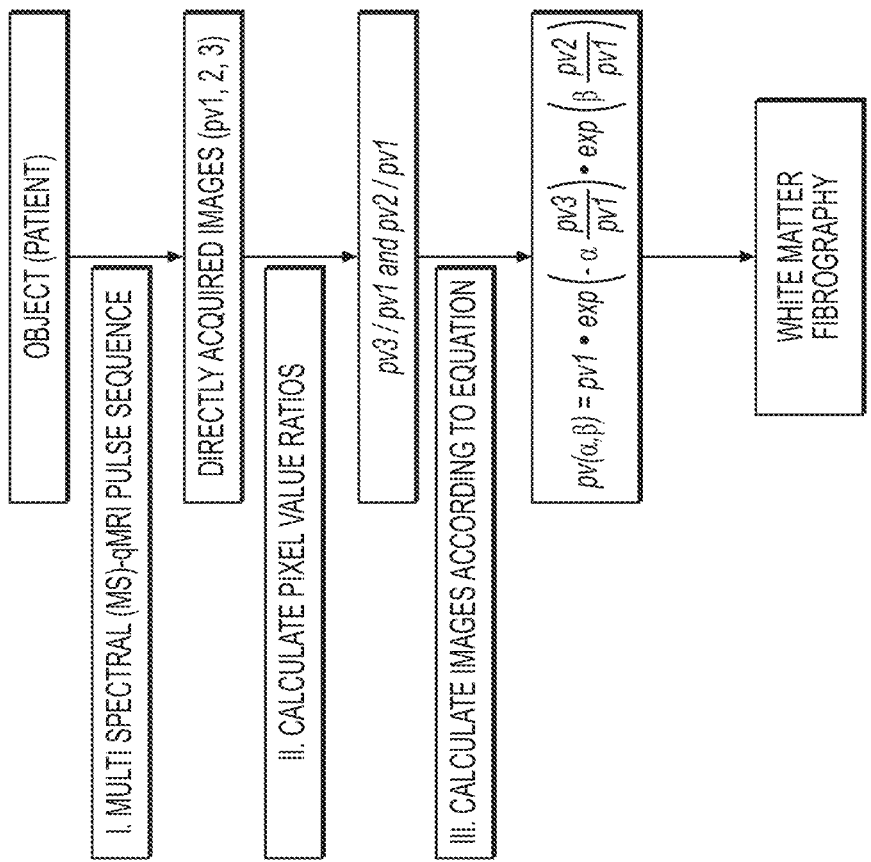
FIG. 9 shows a flow chart describing a specific exponential method for WMF; in accordance with an implementation as described herein.

In a second embodiment an exponential white matter fibrogram (WMF) generating algorithm is used to generate a connectome for the brain of a subject. A flow chart representative of the embodiment is shown in FIG. 9 (Method 2: Exponential pixel-value-ratio algorithm). A plurality of differently weighted MR images (pv1, pv2, pv3) are acquired with a single or multiple pulse sequences, a WM fibrogram can be generated by calculating the pixel value ratios (pv3/pv1 and pv2/pv1) and using these ratios as arguments to the exponential functions F and G, which have adjustable parameters α and β respectively.

Figure 10:
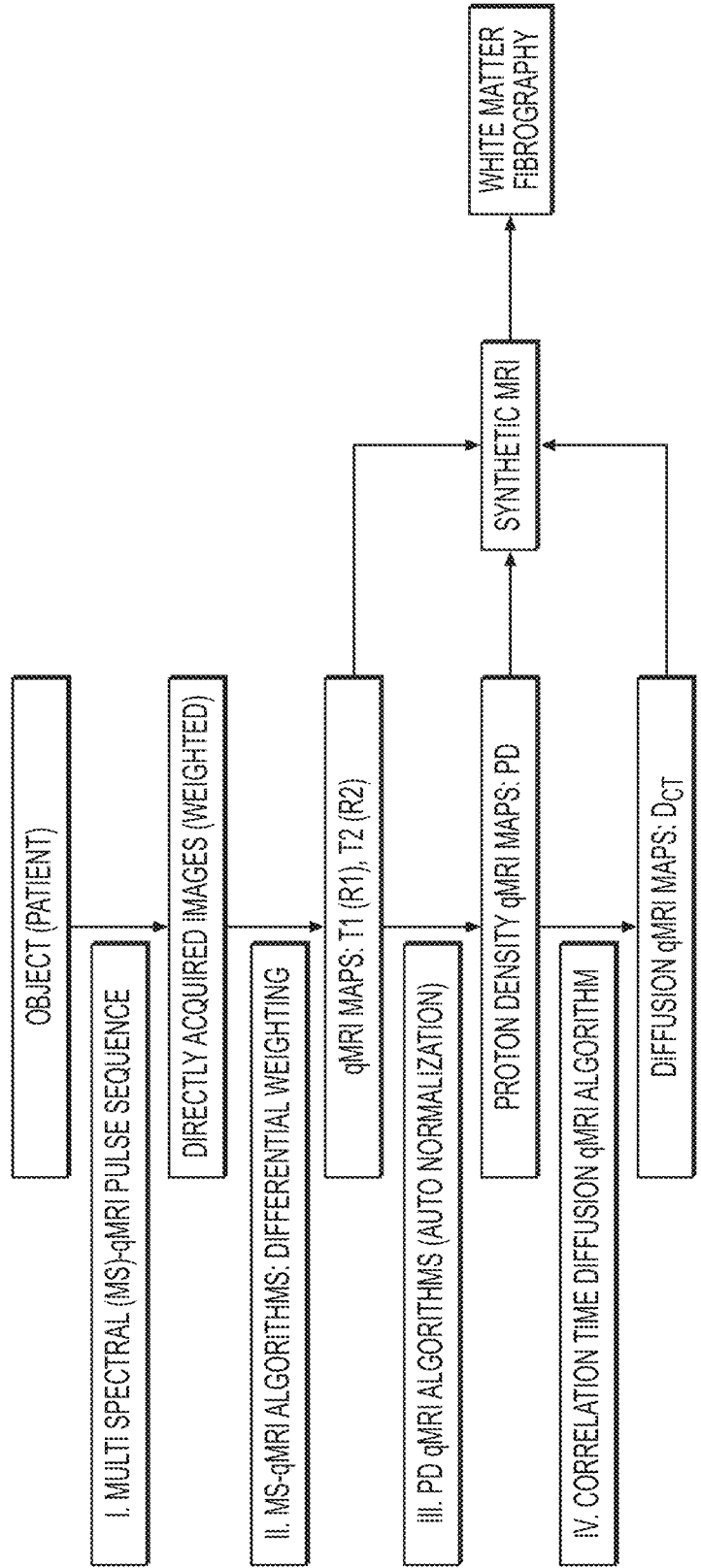
FIG. 10 shows a flow chart describing the full qMRI method for WMF; in accordance with an implementation as described herein.

In a third embodiment a fully quantitative as well as exponential white matter fibrogram (WMF) generating algorithm is used to generate a connectome for the brain of a subject. A flow chart representative of the embodiment is shown in FIG. 10 (Method 3: MS-qMRI algorithm). A plurality of differently weighted MR images (pv1, pv2, pv3) are acquired with a single or multiple pulse sequences, a WM fibrogram can be generated by calculating the pixel value ratios (pv3/pv1 and pv2/pv1) and using these ratios for calculating quantitative maps of the proton density (PD), the longitudinal magnetization relaxation rate (R1) or relaxation time (T1), and the transverse magnetization rate (R2) or relaxation time (T2). This embodiment of the invention offers additional quantitative information in the form of calibrated qMRI maps and additionally offers an intuitive interpretation of the process: a virtual patient being scanned with a virtual MRI scanner. Notably, the synthetic MRI pulse sequence may simulate a real pulse sequence or may be extended to include more general pulse sequences with no specific physical and hardware limitations.

Figure 11:
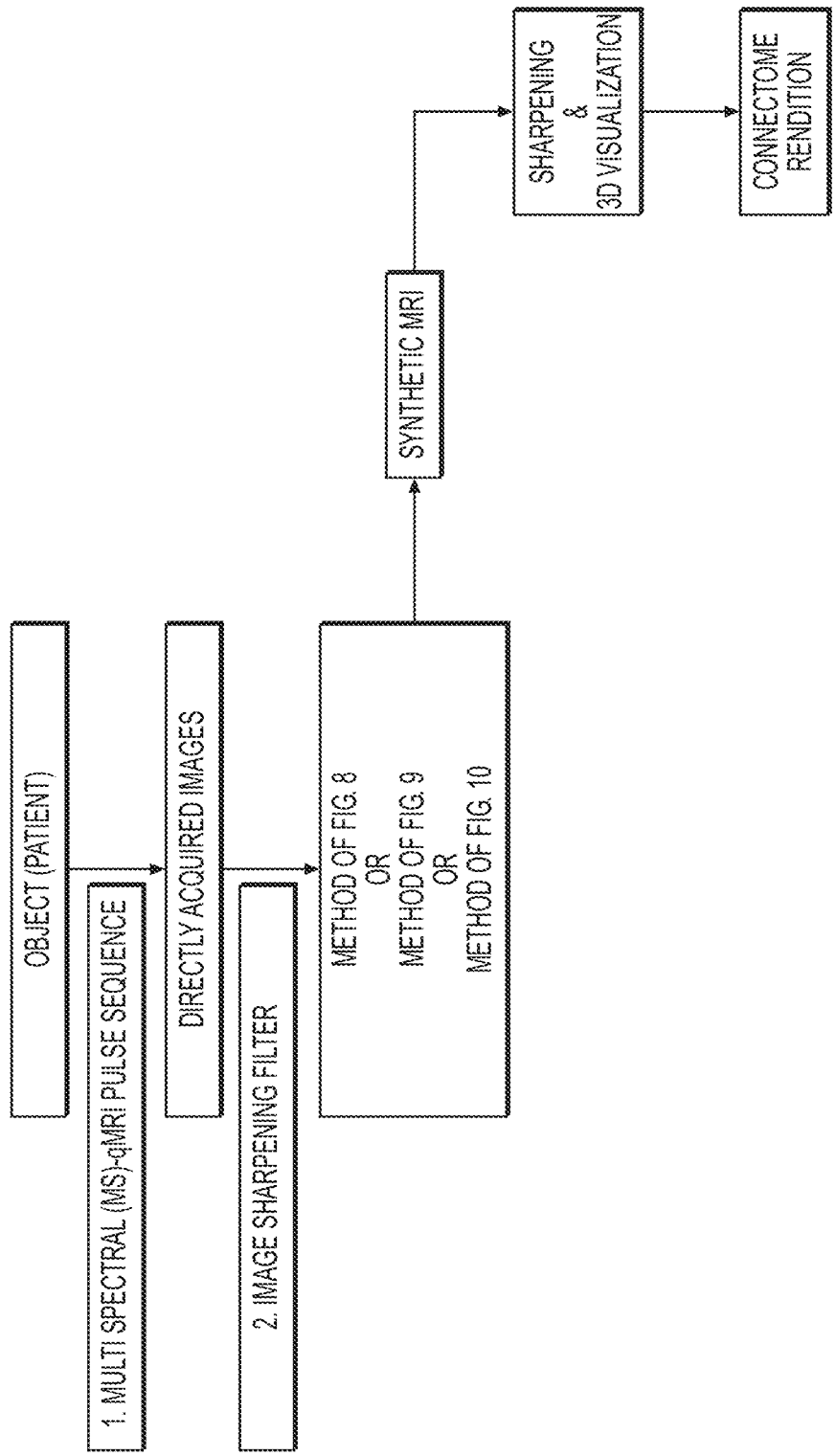
FIG. 11 shows a flowchart of a white matter fibrography embodiment including brain segmentation, also known as skull stripping. Directly acquired images with various levels of T1-, T2-, and PD-weightings are generated by scanning with an MS-qMRI pulse sequence and processed with algorithms for generating the spatially coregistered PD, T1, and T2 maps. The relaxation time maps are further processed to generate maps of the relaxation rates R1 and R2. The resulting PD and R1 maps are then used as the virtual patient for synthesizing the heavily R1-weighted images which exhibit the clearly discernable WM texture. Upon sharpening and 3D-to-2D projection, connectome renditions are generated.

In a fourth embodiment of the invention (FIG. 11), the three preceding methods (FIGS. 8, 9, and 10) can use an image sharpening applied filter upon reading the directly acquired images and/or after the generation of the heavily R1-weighted synthetic images, as shown in FIG. 11.

Figure 12:
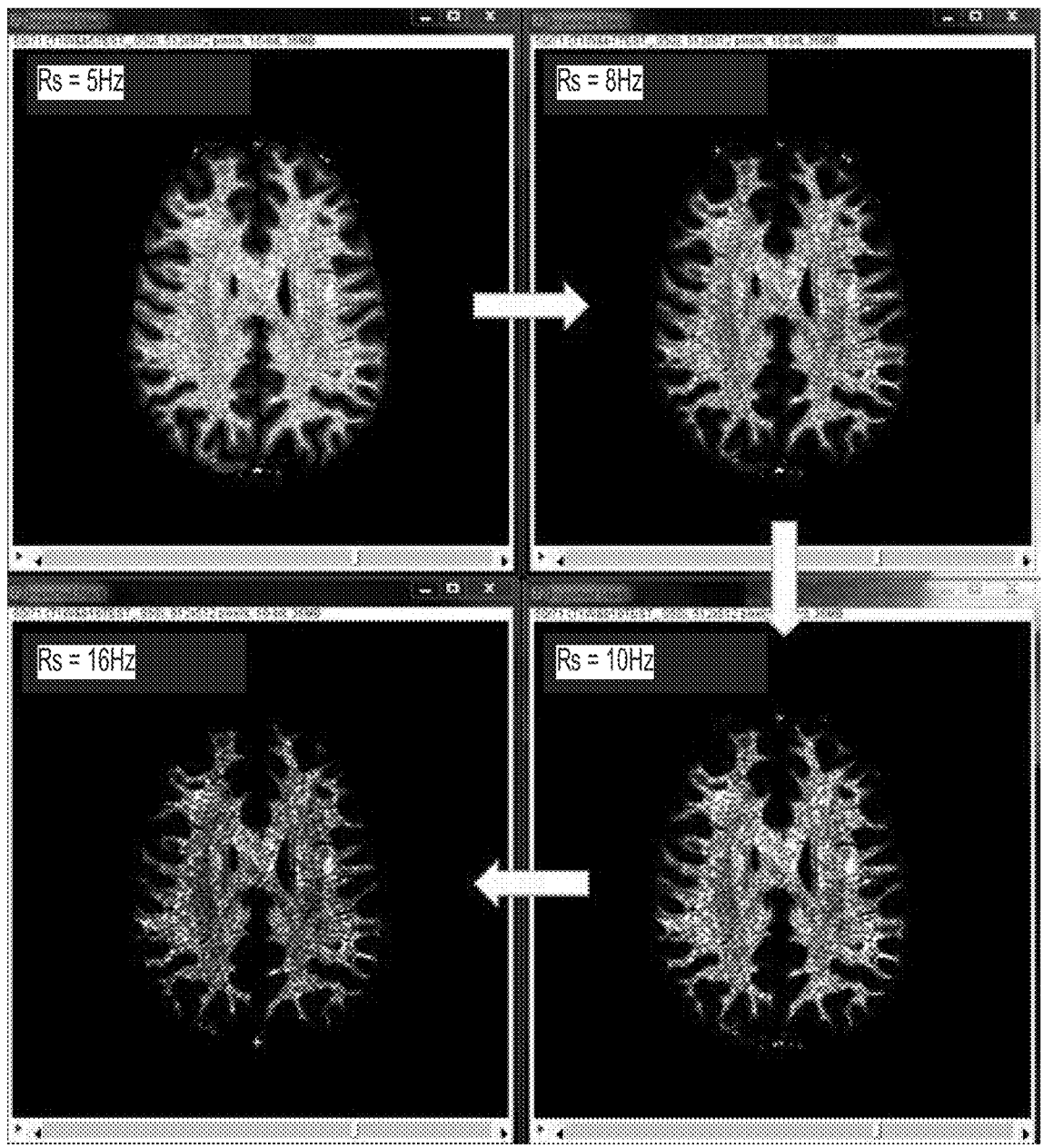
FIG. 12 shows the white matter texture enhancement obtainable with Synthetic MRI with R1 weighting; in accordance with an implementation as described herein.

The WM texture enhancement effects obtained with R1-weighted synthetic MRI increase as a function of increasing the value of the weighting parameter omega (Ω). This effect is illustrated in FIG. 12 for four values of the parameter Ω in the range between 5 Hz and 16 Hz.

The WM texture enhancement effects are studied systematically (FIG. 13) to find an optimal range for Ω taking consideration of the image noise level. Calibration of Ω results in an optimal range of 5 Hz to 16 Hz. This range applies to MRI scanners with B0=1.5 T and 3.0 T. Different Ω ranges and values may differ at B0 fields outside the 1.5-to-3.0 T clinical range.

Figure 14:
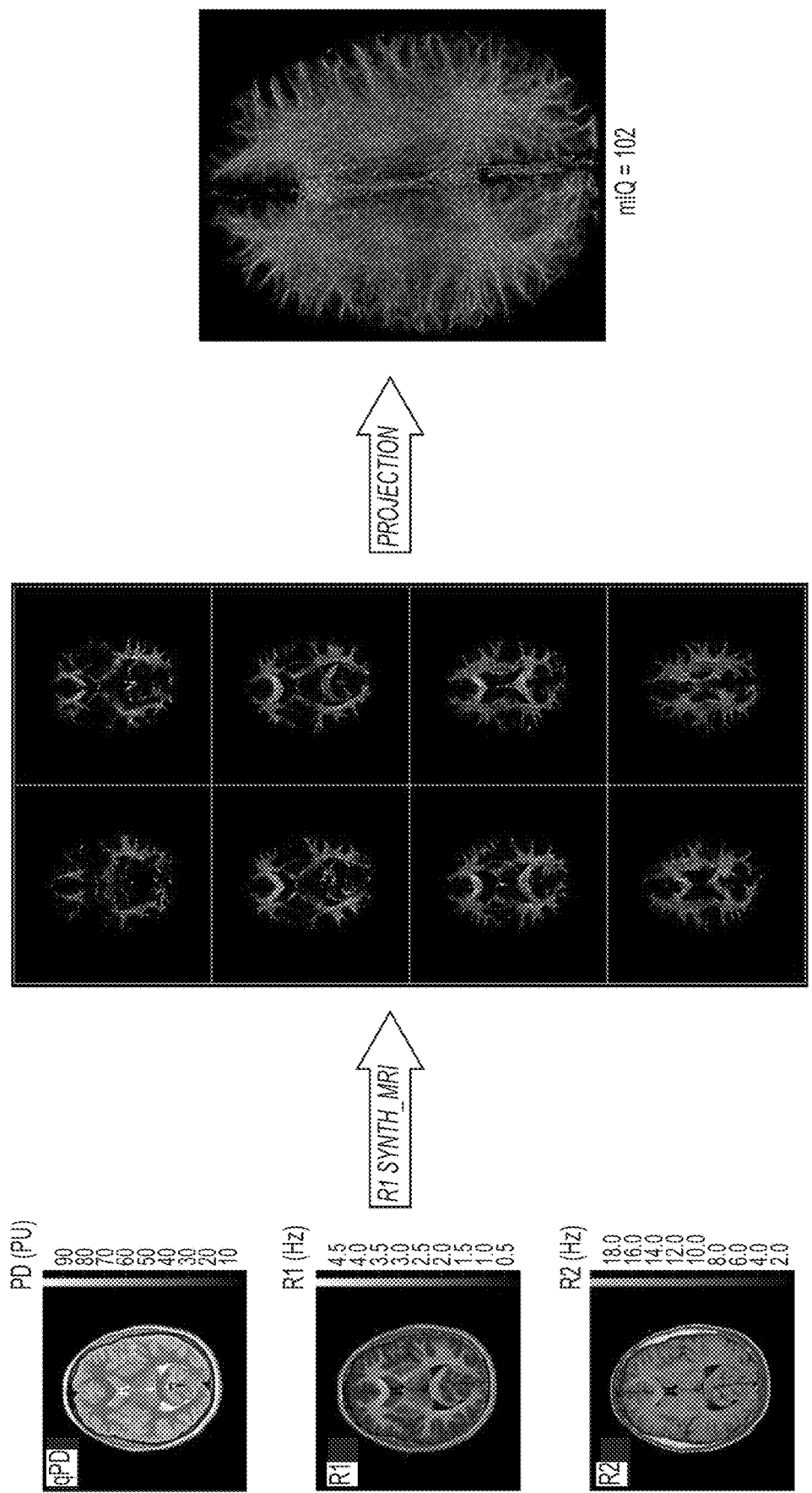
FIG. 14 shows graphically the WMF image processing pipeline from qMRI maps to R1-weighted images, to full connectome rendition; in accordance with the main invention principle as described herein.

Using a Ω value of 10 Hz, the full image processing pipeline is shown graphically in FIG. 14. Starting with the PD, R1, and R2 qMRI maps (left panel) to the WM texture enhanced images of several slices (center panel), to a full rendition of the connectome of a 15 year old female with normal cognition.

D. Materials and Methods

1. Ethics and Subjects: Boston University Medical Center

This data was acquired as part of a prospective study protocol that was approved by the Institutional Review Board (IRB) of Boston University Medical Center. All subjects provided written consent.

For the aging study, 12 subjects were selected from our brain qMRI database. For data consistency only subjects scanned at 1.5 T using the same MS-qMRI pulse sequence (mixed-TSE) (15) and who had a normal by MRI clinical report were chosen. Subjects who received intravenous contrast administration were not included. In addition, two healthy volunteer subjects were scanned at 3.0 T using this same IRB approved protocol.

2. Ethics and Subjects: ELGAN Study

The Extremely Low Gestational Age Newborn (ELGAN) study is prospective observational study that was approved by the Institutional Review Boards of the 12 participating institutions (42). Participating institutions of the ELGAN study are from three geographic hubs: 1) The New England Hub (Baystate Children's Hospital, Springfield, Mass., Children's Hospital of Boston, Boston, Mass., Tufts Medical Center, Boston, Mass., UMass Memorial Hospital, Boston, Mass., Yale-New Haven Children's Hospital, New Haven, Conn.). 2) The North Carolina Hub (East Carolina University, Greenville, N.C., North Carolina Children's Hospital, Chapel Hill, N.C., Wake Forest School of Medicine, Winston-Salem, N.C.). 3) The Lake Michigan Hub (Michigan State University, East Lansing, Mich., Helen DeVos Children's Hospital, Grand Rapids, MR, University of Chicago Medical Center, Chicago, Ill., William Beaumont Hospital, Royal Oak, Mich.). Images used in this disclosure are from one site: from North Carolina Children's Hospital, Chapel Hill, N.C.

3. Measures of Cognition

General cognitive ability (or IQ) was assessed with the School-Age Differential Ability Scales-II (DAS-II) Verbal and Nonverbal Reasoning scales (43) as reviewed in detail elsewhere (44). Two 15 year-old females were chosen for this paper to illustrate the marked connectome differences.

4. MS-qMRI at BMC (1.5 T and 3.0 T)

Mixed-TSE is a multislice four time points MS-qMRI pulse sequence that has been described in the literature (15). It combines in a single acquisition the principles of T1-weighting by inversion recovery and of T2-weighting by dual-echo sampling. The mixed-TSE pulse sequence begins with a slice selective inversion pulse and acquires dual TSE data, i.e., two effective echo times TE1eff and TE2eff at two different inversion times TI1 and TI2. In this way, four self-coregistered images per slice are generated, each with different levels of T1- and T2-weightings: the first two correspond to the two echoes acquired at inversion time TI1, and, analogously, the second two correspond with the echoes at the second inversion time TI2. The mixed-TSE pulse sequence interrogates two interleaved packages of slices sequentially acquired in the same acquisition. The inter-slice gap of each package is chosen equal to the slice thickness, resulting in a contiguous image dataset with negligible inter-slice cross talk artifacts. The directly acquired images can be processed to generate qMRI maps portraying the T1 (and R1), T2, and PD distributions simultaneously and with the native spatial resolution and anatomic coverage of the directly acquired mixed-TSE scan.

The second MS-qMRI pulse sequence tri-TSE was implemented in the two 3.0 T MRI scanners of our hospital; this is a three time points MS-qMRI pulse sequence that achieves T1-weighting by magnetization saturation and PD- and T2-weightings via a dual-echo (DE) TSE imaging. As such Tri-TSE consists of a single echo-TSE scan that is run in temporal concatenation, and with the same pre-scan settings, with a DE-TSE scan; all together it generates T1-, T2, and PD-weighted directly acquired images, which can be qMRI processed to generate coregistered maps of T1, T2, and PD. Tri-TSE was implemented at 3.0 T at high spatial resolution on the two clinical scanners of our institution (Discovery MR750w, GE Healthcare, Waukesha, Wis. and Achieva, Philips Healthcare, Cleveland, Ohio).

5. MS-qMRI for the ELGAN Study (1.5 T and 3.0 T)

Tri-TSE images were acquired with MRI scanners built by three manufacturers: General Electric Healthcare (n=3), Philips Healthcare (n=2), and Siemens Healthcare (n=7) with magnetic field strengths of 3.0 T (11 sites) and 1.5 T (one site). In all cases, the body quadrature coil and the head phased array coil were used for RF transmission and signal reception respectively.

6. Image Processing

The multiple directly-acquired images per slice of the mixed-TSE or tri-TSE or DE-TSE acquisitions were used to create maps of the relaxation times, the relaxation rates, and the normalized proton density using qMRI algorithms programmed in Mathcad (PTC, Needham, Mass.) and Python 3.5, using the Canopy integrated development environment (Enthought, Austin, Tex.). The skull and extracranial tissues were removed using a dual clustering segmentation algorithm (45). Longitudinal magnetization relaxation rate (R1) heavily images of the intracranium were then generated with a synthetic MRI engine. The skull stripped R1-weighted synthetic images, which show well-defined white matter structure, were processed with Fiji (48): first sharpened with the "Unsharp mask" filter (radius=1 and mask weight=0.6), orange colorized, and then 3D-to-2D projected using the Volume Viewer plugin of Fiji (https://imagej.nih.gov/ij/plugins/volume-viewer.html). This procedure results in connectome renditions as presented in the various figures of this disclosure.

7. Synthetic MRI and R1 Contrast Optimization

An exponential R1-weighting image synthesis algorithm was implemented with a simple exponential R1 weighting function:

$$I_{Synth}(\Omega) = PD \, \exp(-\Omega/R1) \qquad [1].$$

Figure 13:
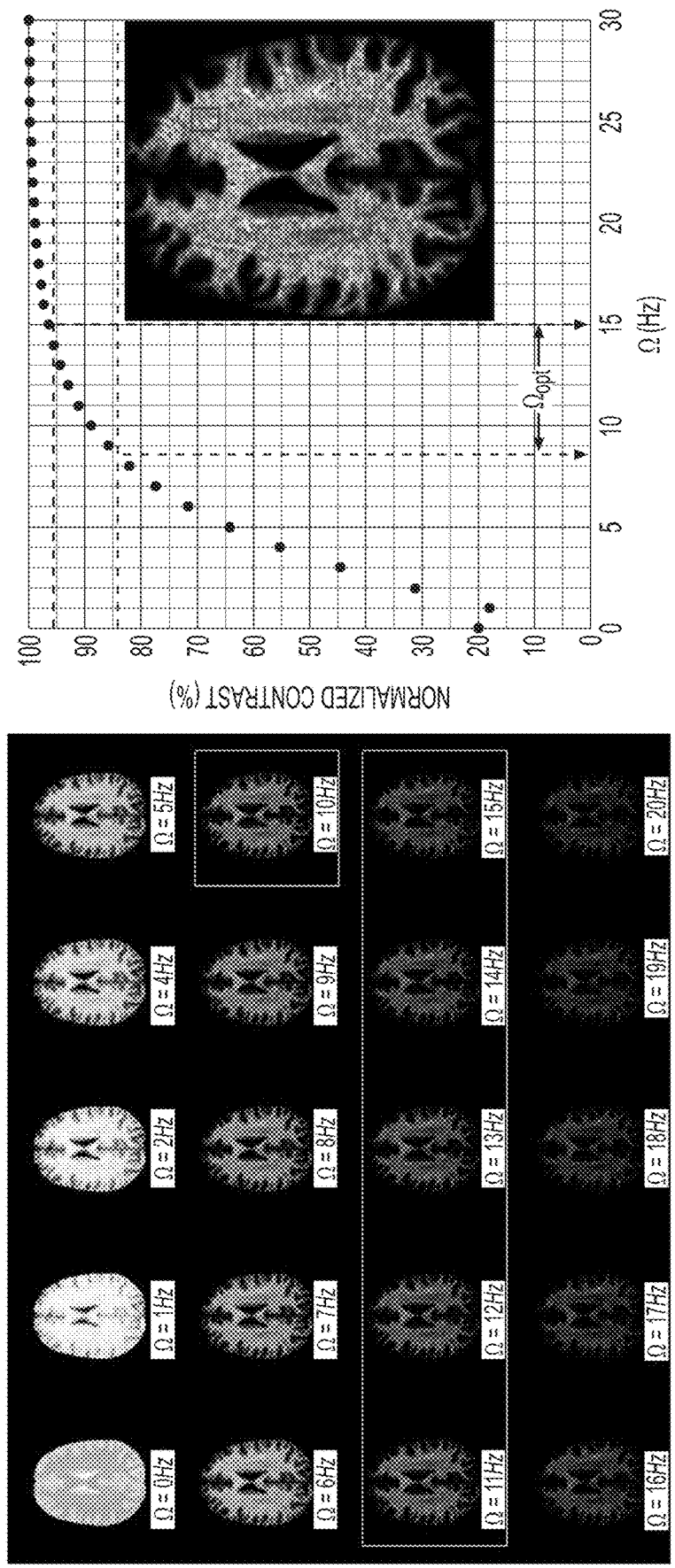
FIG. 13 shows the calibration procedure used for determining the optimal R1 weighting range for Synthetic MRI based connectome generation; in accordance with the main invention principle as described herein.

In this formula, PD is the proton density and Ω is the relaxation rate weighting factor, which has a practical range of $\Omega \in (0, \sim 25 \text{ Hz})$ with the maximum value being a function of the signal-to-noise ratio available in the PD and R1 maps (see FIG. 13).

The imaging effects resulting from progressively increasing the level of synthetic R1 weighting, as imparted by increasing the value of the parameter Ω in Eq. 1, are demonstrated in FIG. 13 (left panel) for a typical slice of a 46.5 yo male scanned at 1.5 T. WM differentiation between two distinguishable WM tissue compartments is clearly visible starting at about $\Omega=4$ Hz and becomes increasingly emphasized at higher $\Omega$ values while the overall signal-to-noise (SNR) decreases exponentially. A range for optimum connectome rendition that balances contrast maximization vs. SNR deterioration can be estimated by plotting the contrast between the two WM tissue compartments over a region-of-interest (ROI) vs. $\Omega$. An ROI of a typical WM region (FIG. 13, right panel) was chosen and the following formula was used:

$$C_{ROI}(\Omega) = 100 \frac{(\max_{ROI}(\Omega) - \min_{ROI}(\Omega))}{\max_{ROI}(\Omega)}. \quad [2]$$

Figure 15:
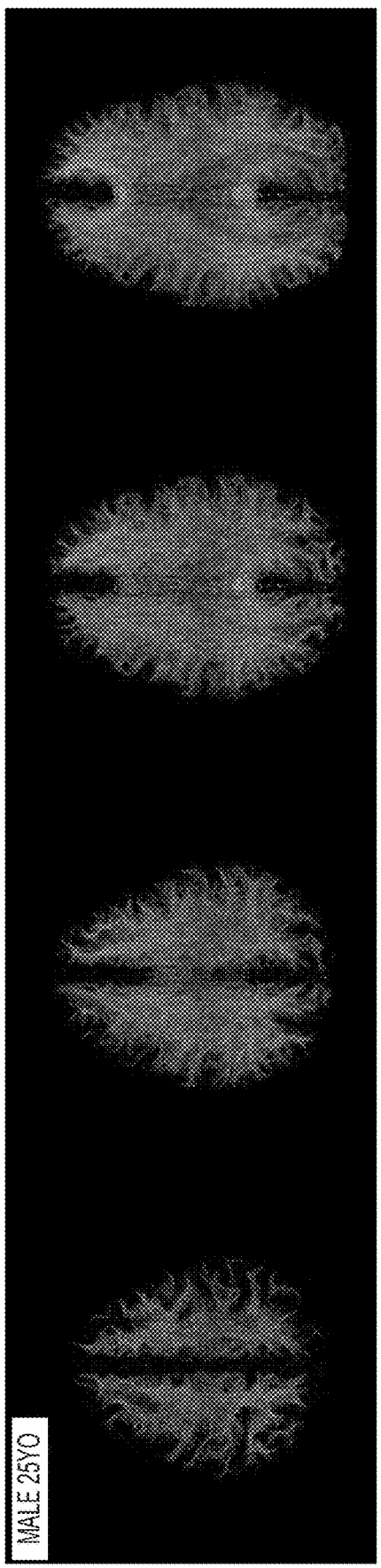
FIG. 15 shows selected connectome renditions from medium high spatial resolution data obtained with 3.0 T MRI scanners of different manufacturers. Top row (male 25 yo): Axial connectome projections progressively including added anatomical coverage in the superior to inferior direction, starting from the head apex to the pons. A high level of left-right symmetry is observed all these partial connectome renditions. Bottom row (male 52 yo): coronal, axial, and sagittal partial projections illustrating the basic connectome features of the normal adult brain WM matrix as observed from three orthogonal directions.
Figure 15:
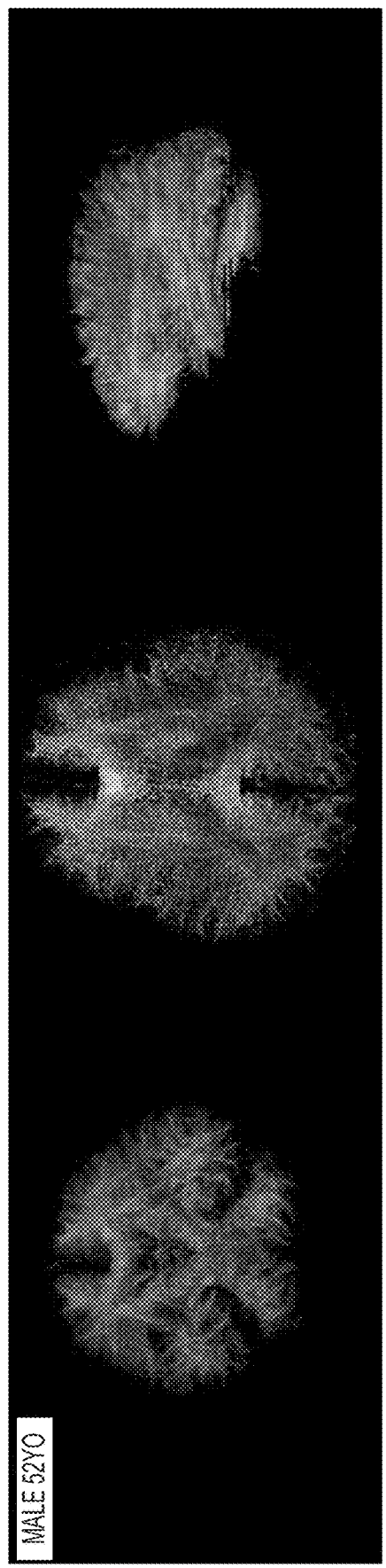

Assuming typical image noise levels in the 5%-10% range, the curve in FIG. 15 (right panel) predicts an optimal range of $\Omega \in (6\ Hz, 15\ Hz)$ and this is further confirmed by the corresponding synthetic images at the left panel.

8. Image Processing Pipeline (qVision)

The image processing pipeline (qVision v6.x) consists of numerous functions for segmentation and mapping algorithms programmed in Python (version 3.6.9, 64 bits with the Enthought Deployment Manager) installed in MS Windows personal computers. This sequential multi-subject image processing pipeline is fully automated, except for two preparation steps done with Fiji (freeware: https://fiji.sc/): 1) editing intracranial matter (ICM) segment after dual clustering segmentation and 2) manual delineation of the superior aspect of the cerebellum. The total preparation time of each subject was about 30 min and needed to be performed once as the cerebrum and cerebellum segments were stored in the database. After this preparation phase, qVision proceeds without any human intervention processing automatically all subjects in the database with a processing time of about 30 minutes per subject at the native acquisition geometry of 80 slices and matrix size=512×512. For each subject, it saves the PD-T1-T2 qMRI maps and histograms, and MS-qMRI reports for cerebrum and cerebellum separately.

9. MS-qMRI Algorithms

The Tri-TSE qMRI mapping formulas for PD, T1, and T2 are given below (formulas 3, 4, and 5, respectively). These pixel-by-pixel formulas express the three qMRI parameters as functions of pulse sequence parameters in accordance with an approximate Bloch equation model of the Tri-TSE pulse sequence.

Given the Tri-TSE directly acquired images DA1, DA2, and DA3, we calculated the PD, T1, and T2 coregistered maps using the three formulas below. These were derided using a general Bloch equation of the Tri-TSE pulse sequence that is applicable to the three vendors, because TSE readout specifics are treated by the adjustable calibration factors cf2 and cf3.

$$PD = \left(\frac{cf1}{C_{coil}}\right) \frac{\left(DA1\exp\left(\frac{TE1eff}{T_2}\right) + DA2\exp\left(\frac{TE2eff}{T_2}\right)\right)}{\left(1 - \exp\left[-\frac{(TRlong - TSEshot\_de)}{T_1}\right]\right)} \quad [3]$$

In this equation, cf1 is a scalar that is auto adjusted to normalize PD to the mean value of CSF. The array $c_{coil}$ is a map of the sensitivity profile of the receiver coil, modeled as the Fourier Transform of the very low spatial frequency components of DA1.

$$T_1 = Root_{(hybr)} \quad [4]$$

$$\left\{T_1 + \frac{TRshort}{\ln\left(\frac{1 - \left(\frac{DA3}{DA1}\right)\left(\frac{\left(1 - \exp\left(-\frac{TRlong}{T_1}\right)\right) - }{cf2\exp\left[-\frac{(TRlong - TSEshot\_de)}{T_1}\right]}\right)}{\left(1 + cf2\exp\left[\frac{TSEshot\_se}{T_1}\right]\right)}\right)}\right\}$$

At each pixel location T1 is calculated as the root of the expression inside bracket using the modified hybrid Powell method (https://docs.scipv.org/doc/scipv/reference/optimize.root-hybr.html #optimize-root-hybr).

$$T_2 = cf3 \frac{(TE1eff - TE2eff)}{\ln\left(\frac{DA2}{DA1}\right)} \quad [5]$$

The qMRI processing pipeline has three harmonization parameters, namely cf1, cf2, and cf3 the values of which are fixed for each site and were determined by running the pipeline at half the spatial resolution.

10. Tissue Segmentation

The ICM in toto including cerebrospinal fluid (CSF), meninges (MN), gray matter (GM), and white matter (WM) were segmented using a three-channel dual-clustering algorithm. The operational principle being that of interrogating every pixel in the three-dimensional dataset as to whether it belongs to a predefined volume in PD-T1-T2 space—i.e. a qMRI cluster—and simultaneously, whether it is surrounded by qMRI-similar pixels—i.e. spatial cluster—. The resulting pixel clusters were further checked for internal connectivity thus improving the ICM segmentation accuracy. As mentioned above, the ICM segments were visually inspected and edited using Fiji's manual editing tools thus leading accurate ICM segments, which were then separated into cerebral and cerebellar segments using the manual editing tools of Fiji.

11. White Matter Texture Enhancement by R1-Weighted Synthetic MRI

WM texture hidden in PD maps can be revealed by using R1-weighted Synthetic-MRI using formula [1], in which the useful range of the weighting parameter is: $\Omega = \{0, 5R1(WM)\}$.

In qVision, this parameter is automatically adjusted for each subject to $\Omega_{opt}=4\ R1(WM)$ to generate optimal texture conspicuity.

12. Spatial Entropy Mapping

If considering a generic variable, the values of which follow a certain probability distribution, entropy is interpreted as the information content of that distribution. As such, information is defined in terms of the prior probabilities of certain values (events) occurring; the greater the prior uncertainty of such an occurrence, the greater the information gained if such an event occurs.

In the special case of spatial information, i.e. images and maps, the correspondent meaning of spatial entropy (SE) is a pixelwise measure of the amount of local structural information, or spatial complexity of a given region of space. The SE of an image A at a given pixel (m, n) is calculated with formula [6] (Celik 2014):

$$SE\{A\}_{m,n} = - \sum_{disk(j,k,R)} h(m, n)_{(j,k)} \log_2(h(m, n)_{(j,k)}) \quad [6]$$

in which $h(m,n)_{(j,k)}$ is the histogram value of the gray-levels in a disk of radius R, or equivalently the probability of occurrence of that pixel value in the disk; in this implementation a disk of radius R is centered about pixel (m, n). We used the entropy function of Scikit-Image (van der Walt, Schönberger et al. 2014) to generate spatial entropy maps of $I_{Synth}$ (Eq. 1) with a disk of radius of 4 pixels as identified through the optimization procedure outlined in Example 7. With appropriate conversion factors, the SE units reported herein are kBytes.

13. Myelin Water Maps

Synthetic R1-weighted images portray the myeloarchitectural framework of the brain, which conforms to the shape of WM fibers. To transform these qualitative images into quantitative myelin water maps, two mathematical operations are needed: First transformation of the synthetic R1-weighted images into binary maps. This is done through isolation of high intensity pixels from the white matter texture images such that only those associated with the shortest T1 components remain. It has previously been demonstrated these components are directly associated with myelin water in the central nervous system (Labadie, Lee et al. 2013, Lutti, Dick et al. 2014). Second, we use the resulting binary maps as masks to the previously calculated, water-calibrated proton density maps. The corresponding formula [7] is:

$$MW_{image} = PD \text{ binary}\{I_{synth}(\Omega_{opt})\} \quad [7]$$

Figure 25:
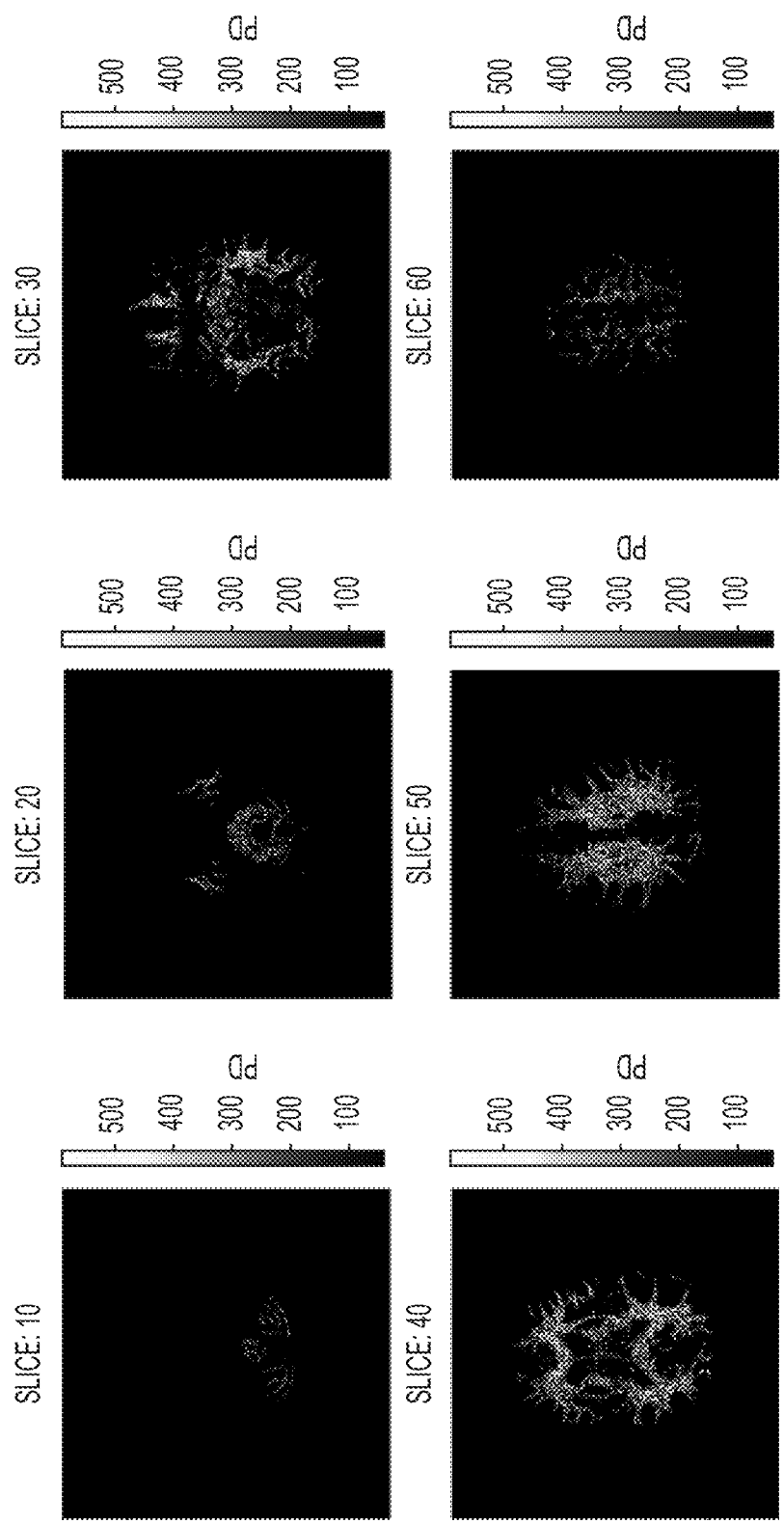
FIG. 25 shows myelin water images calibrated to the proton density of intraventricular cerebrospinal fluid (i.e. water equivalent: PDcsf=1000 in the scale above). The full MWI dataset has the native high spatial resolution of the Tri-TSE dataset and provides full head coverage (80 slices, voxel=0.5×0.5×2 mm$^3$).

This process leads to MW PD maps such as those in FIG. 25. The initial calibration of PD relative to the value of water (or cerebrospinal fluid) results in automatic MW PD calibration. Furthermore, the binary image can be used to mask the T1 and T2 maps, further enhancing the quantitative power of the technique for more complete characterization of myelin water and the connectome.

E. Examples

Example 1: Scanning Platform Independence

As a first step for validating WMF, MRI scanning platform independency was shown by analyzing imaging data at a medium-high spatial resolution (voxel=0.5×0.5×2 mm³). Comparable quality imaging data generated with two 3.0 T MRI scanners of different manufacturers was processed in under 8 min of scan time each. The resulting connectome renditions of the two healthy volunteers shown in FIG. 15 have comparable quality in terms of signal-to-noise, fiber delineation, left-right symmetry, and organization. Also noticeable is the high fiber density in the prefrontal lobe, which characterizes the adult human brain.

Example 2: Effects of Advancing Age (1.5 T)

Figure 16:
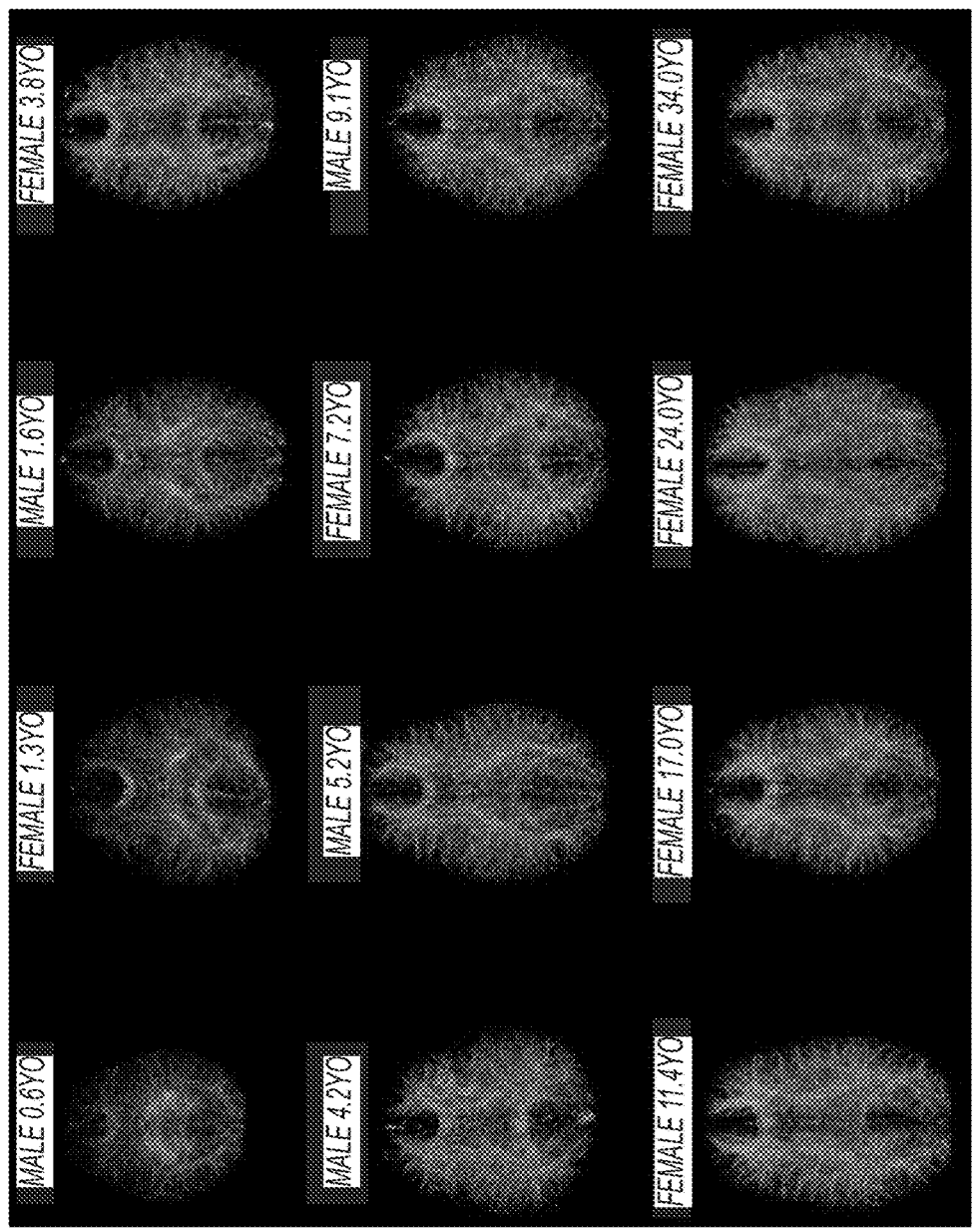
FIG. 16 shows connectome maturation from infancy (0.6 years) to young adulthood (34 years) at 1.5 T. Developmental sequence of the normal brain connectomes as a function of increasing age illustrates the main anatomical and myelinated fiber distribution patterns of WM change. From 0.6 years to 1.6 years, myelination occurs at a very fast pace expanding in all directions peripherally from the center. Our findings are in agreement with prior descriptions: as described in reference (17) and references therein; a central to peripheral progression of myelination can be observed, starting in the brainstem and thalamus (in utero), and progressing to primary sensory and later to association cortical areas.
Figure 16:
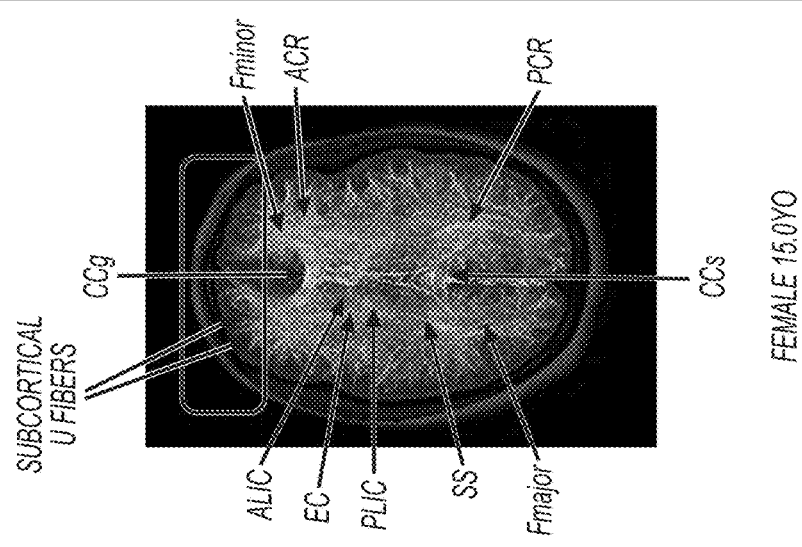

A second WMF validation step illustrates the normal brain age-related changes: whole brain axial connectome renditions as a function of increasing age are shown in FIG. 16 using lower spatial resolution (voxel=0.94×0.94×3 mm³) data generated at 1.5 T. High organizational level and basic bilateral symmetry is observed at all ages. Myelination progresses at a very fast pace during the first two years of life during infancy to toddler's first year. The genu of the corpus callosum (CC) is clearly visible at 0.6 years and myelinates anteriorly-to-posteriorly with the CC splenium becoming clearly discernable as early as 1.3 years of age. Globally, the posterior aspect of the brain is markedly more myelinated during infancy and myelination progresses in the posterior-to-anterior direction as well as from the brain's center to the periphery towards the cortex; WM fibers become thinner as these approach the cortex. From early adolescence to young adulthood, the prefrontal WM becomes increasingly myelinated exhibiting higher myelin density that the posterior aspect of the brain.

Example 3: Ischemic Stroke (3.0 T)

Figure 17:
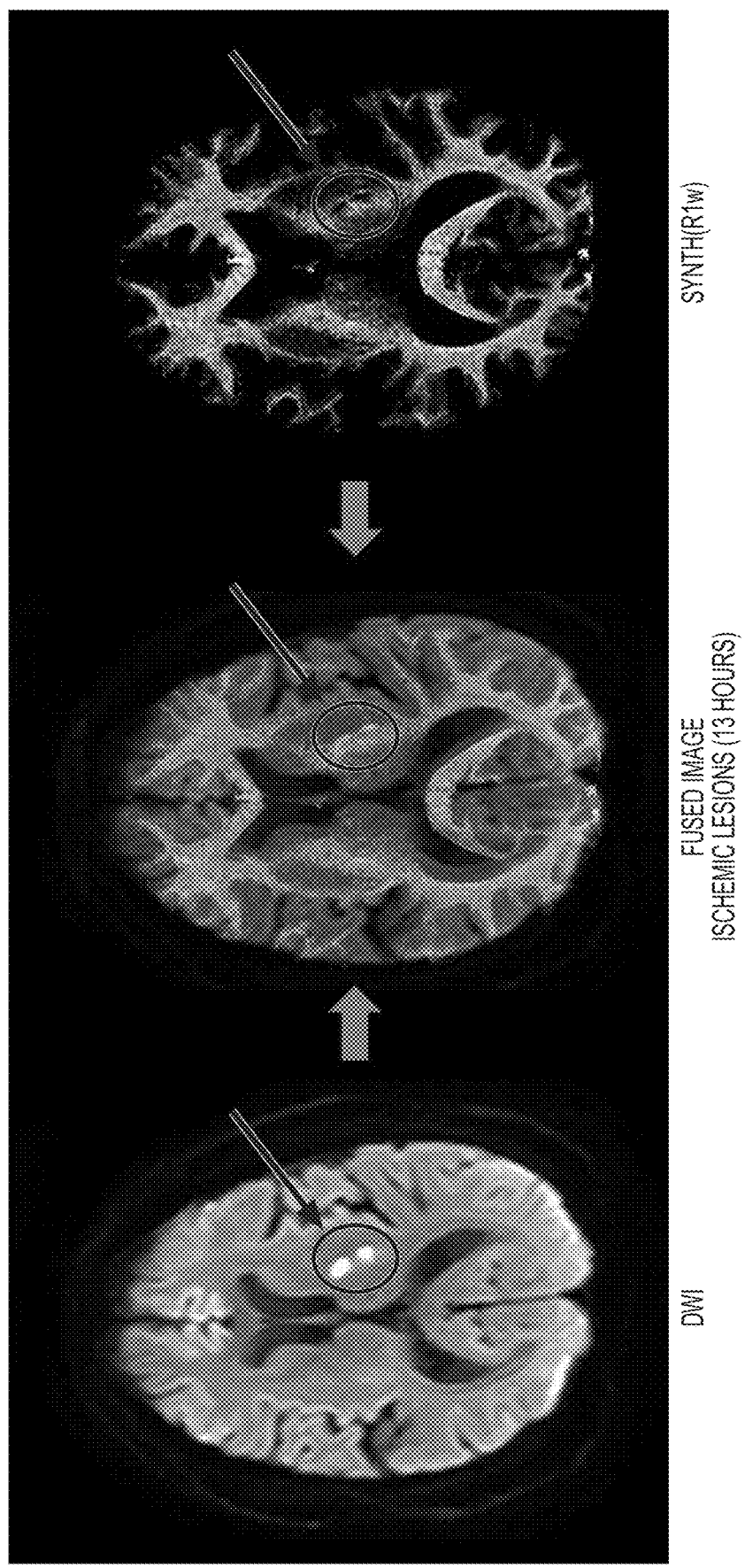
FIG. 17 shows matter damage 13 hours into an acute ischemic stroke. Two 13 hours-old ischemic lesions in left corona radiata and internal capsule demonstrated in the diffusion weighted (left) and ADC map (center) are also clearly observed as a signal void the heavily R1-weighted synthetic image.

A third WMF technique validation step assesses WM integrity under the stress of ischemia. Two acute ischemic stroke lesions (arrow) in a 48 yo female are shown in FIG. 17 via standard dMRI as bright lesions in diffusion weighted image (DWI) and dark lesions in the map of the apparent diffusion coefficient (ADC) thus confirming restricted diffusion. The two lesions appear as signal voids in the R1-weighted image likely indicating irreversible WM obliteration at this stage 13 hours after last time seeing well.

Example 4: Connectome Organization and Cognitive Impairment (3.0 T)

Figure 18:
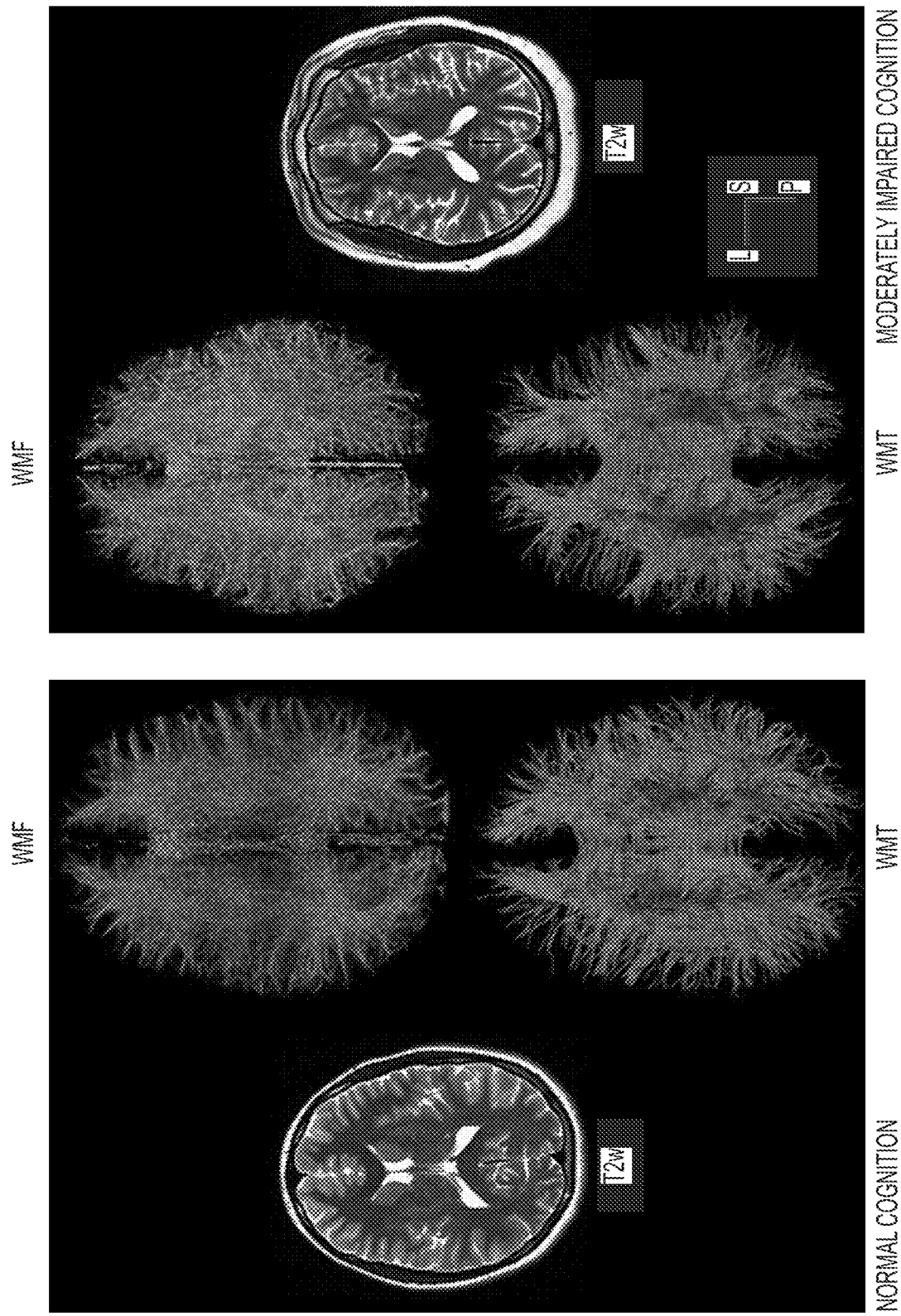
FIG. 18 shows connectome order and disorder and measures of cognition. Left panel: Normal cognition subject born at gestational age (GA) of 27.9 weeks and birthweight (BW) equal to 861 g: IQ (verbal)=99, IQ (nonverbal)=105 resulting in composite IQ=102. Right panel: The moderately impaired female adolescent was born at GA of 26.3 weeks (BW=683 g): IQ (verbal)=54, IQ (nonverbal)=74 resulting in composite IQ=64. Composite IQ=(verbal IQ+nonverbal IQ)/2. Also shown below each fibrogram is the corresponding tractogram generated via DTI.

A fourth step towards WMF technique validation exemplifies the technique's potential for characterizing the level of connectome fiber organizational order or disorder in the context of neurocognitive impairment. The full brain connectomes shown in FIG. 6 are from two 15 yo females of the ELGAN study that differ in neurocognitive abilities as evidenced in part by the DAS-II IQ scores (see legend of FIG. 18). The subject with normal cognition has a highly organized, coherent, and symmetric connectome characterized by a uniform WM fiber curved parallelism; the general appearance of which is similar in overall appearance to published high quality dMRI-WMT whole brain connectomes (12). In contradistinction, the connectome of the moderately impaired subject has much reduced fiber parallelism and overall less organizational coherence throughout the brain but particularly in the posterior aspects. Remarkably, the T2-weighted images (upper corners) of the subjects are very similar and medically unremarkable thus proving an example of the added medical information provided by WMF.

Example 5: Illustration of the Images Obtained at the Different Stages of the Quantitative WMF Algorithm The qMRI maps (qPD, R1, and R2) are further processed with a heavily R1-weighted synthetic pulse sequence embodied in the formula $I_{Synth}(\Omega)=PD \exp(-\Omega/R1)$ in order to generate images that reveal the finer structure of white matter (FIG. 14, center panel). The visual acuity of these intermediary images can be further increasing by using a sharpening filter. A wide array of such sharpening filters are commonly available; here the unsharp mask filter was used followed by a simple projection operation to generate the fibrogram of the right hand side panel of FIG. 14.

Example 6: White Matter Fibrograms of Eight Prematurely Born Adolescents

Figure 19:
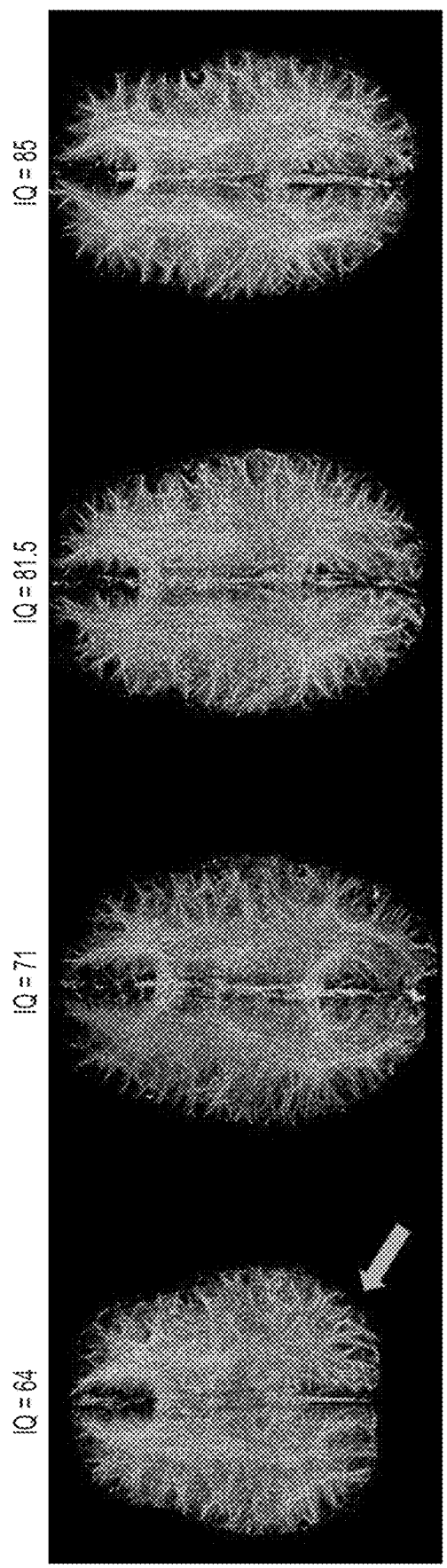
FIG. 19 shows white matter fibrograms of eight prematurely born adolescents (15 years of age) displayed as a function of increasing IQ from left-to-right and top-to-bottom. This figure illustrates the apparent fibrogram differences as well as the consistent high fibrogram quality; in accordance with the image processing methods described herein.
Figure 19:
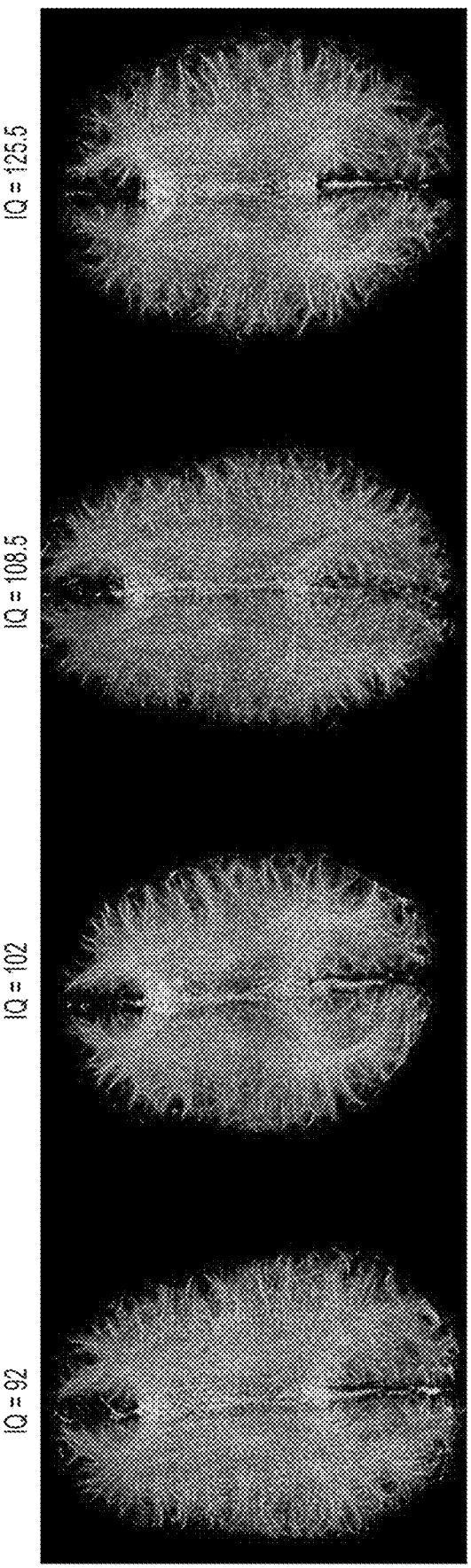
Figure 20:
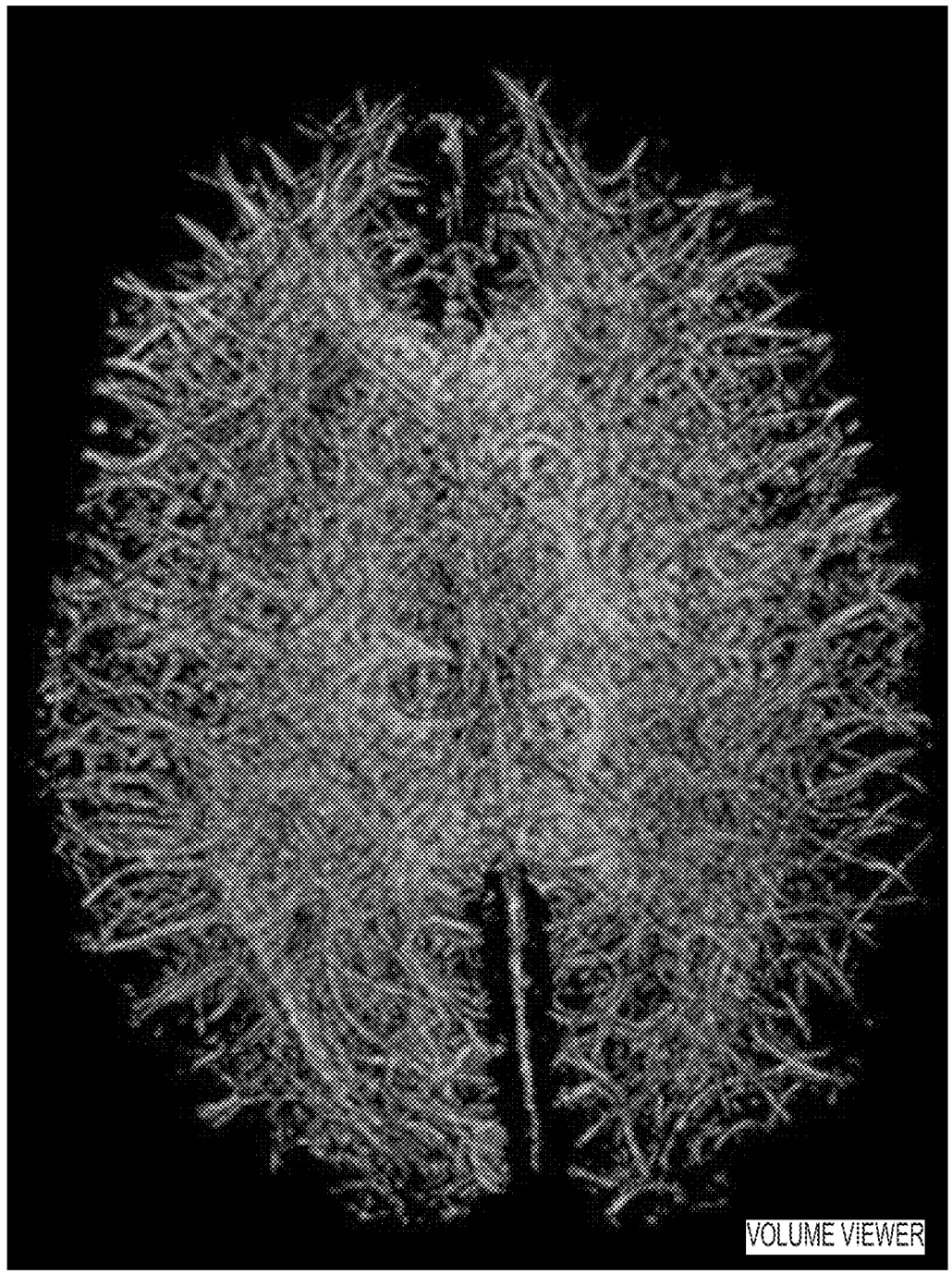
FIG. 20 shows a white matter fibrogram rendered at higher and isotropic spatial resolution via directly acquired image interpolation along the three spatial directions. Resulting interpolated voxel=0.25 mm$^3$.
Figure 21:
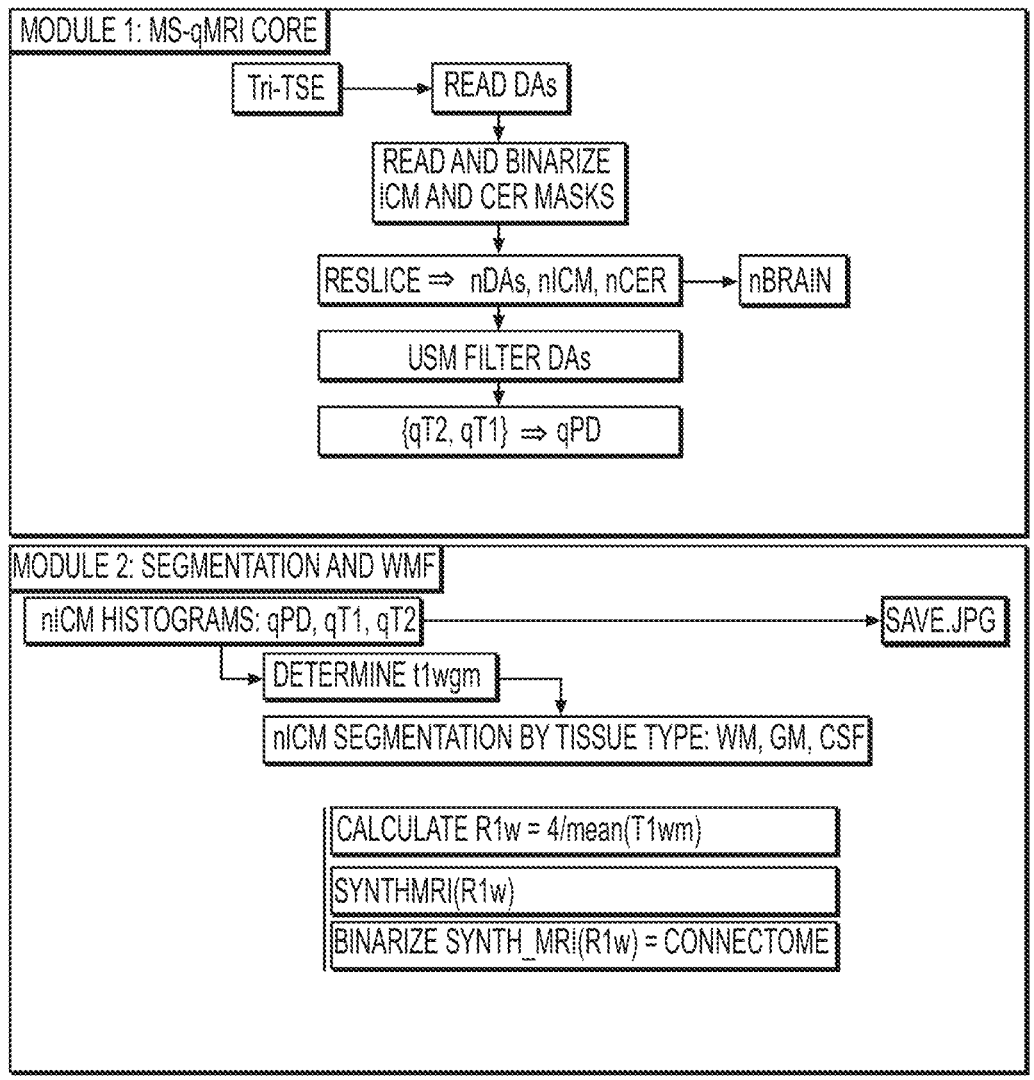
FIG. 21 presents an operational flowchart showing the computational steps that are conducive to the main objective of this disclosure, which is the characterization and quantification of the WMF-connectome renditions. In one embodiment of this invention, the three directly acquired images (DA1, DA2, and DA3) of the triple turbo spin echo (Tri-TSE) pulse sequence are processed leading to qMRI maps of PD, T1, and T2. These are subsequently used to generate several anatomical segments of the central nervous system (ICM, cerebrum, cerebellum, WM, GM, and CSF). The heavily R1 (=1/T)-weighted synthetic images with optimized WM texture are generated by Synthetic-MRI leading to WMF connectome renditions. The R1-weighted synthetic images are thresholded to retain only the pixels with the highest R1 values, which form the foundational scaffolding of the connectome. The images of such connectome scaffoldings can be used in several ways: 1). To map measures of microarchitectural order such as spatial entropy and 2) to mask the PD, T1, T2 maps to produce measures of hydration (PD) and non-aqueous tissue composition via connectome MR relaxometry of T1 or T2 or any other spatially coregistered qMRI map available, for example by standard diffusion MRI.

White matter fibrograms of eight prematurely born adolescents of the ELGAN study as a function of increasing intelligence quotient (IQ), from left to right and top to bottom as labelled in FIG. 19. The fibrogram of the adolescent with moderately impaired cognition has decreased fiber coherence with clearly noticeable random fiber orientations in the posterior aspect of the brain (arrow in FIG. 19). The fibrograms of the two adolescents with normal cognition show well organized and coherently configured fibers.

Example 7: Spatial Entropy: Mapping

Figures 22A, 22B:
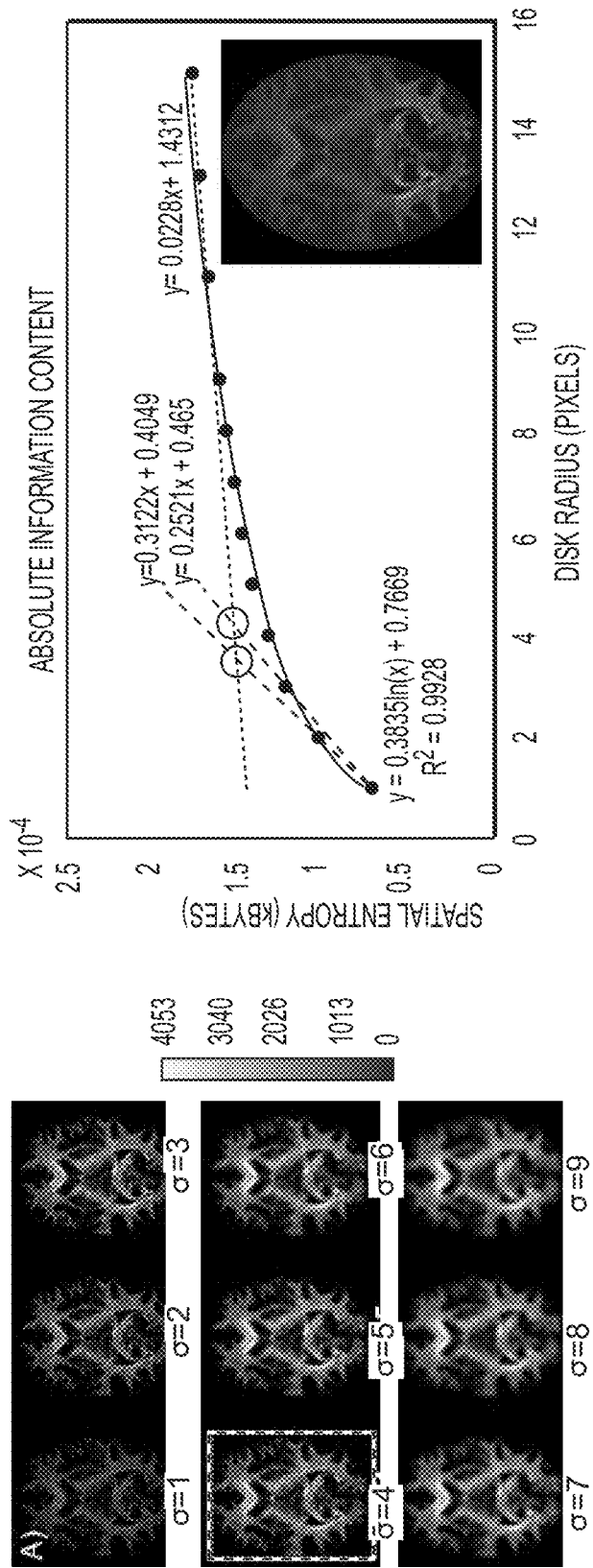
FIGS. 22A and 22B present a spatial entropy disk radius optimization. A) Single slice spatial entropy map of a 15-year-old female calculated with increasing disk radii (a). Large disks result in visual map blurring. B) Graph of single slice region of interest (inset) for frontal white matter versus disk radius. Disk radius of 4 pixels provides optimal information content while preserving the spatial signal.

Spatial entropy calculations with Eq. 6 requires specifying a small region (or disk) about each pixel for calculating the distribution probabilities of values within the disk. Choosing a circular disk is customary. The disk radius expressed in pixels must be optimized according to the tradeoff between two competing criteria: to provide maximum spatial information and minimal structural overlap so that for each pixel, the spatial entropy is a direct measure of the local myeloarchitecture. Such optimal radii are therefore specific to the imaged object structure in relation to the voxel size. In the case shown in FIG. 22, such optimum radius is approximately 4 pixels.

The optimal disk radius was determined via calculation of the mean SE of a single slice at the level of the corpus callosum. Carrying out this calculation for a range of disk radii gives a strong logarithmic fit, where the knee of the curve corresponds to the optimal radii. Since the calculation of entropy has difficulty interpreting non-integer radii due to limitations in the spatial resolution of the source image, we estimated the knee by calculating the point of intersection of three lines. The lines drawn are represented as dashed lines in FIG. 22B and can be thought of as approximations of two distinct regimes to the logarithmic curve. Given the rapid rate of change at small disk radii, two lines were used to approximate this regime. The average of the intersection points (circled) gives an optimal integer disk radius of 4 pixels.

Example 8: Spatial Entropy and Age

Figure 23A:
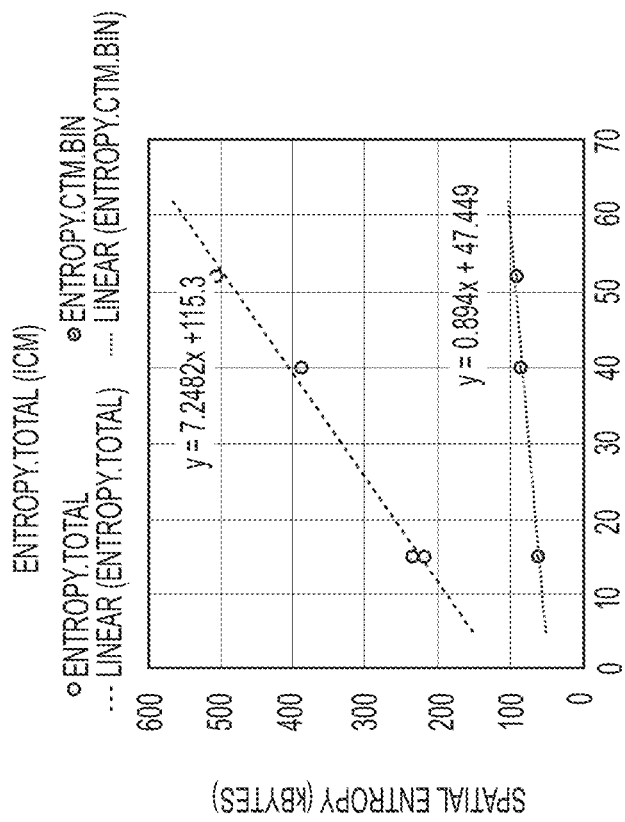
FIGS. 23A and 23B show spatial entropy measures and connectome renderings as function of increasing age. A) Graph of total and reduced entropy as functions of age for the 4 subjects in the bottom insert (B). Note the high rates of increase for both types spatial entropy, which would not be intuitive by visual inspection of the connectome renderings.
Figure 23B:
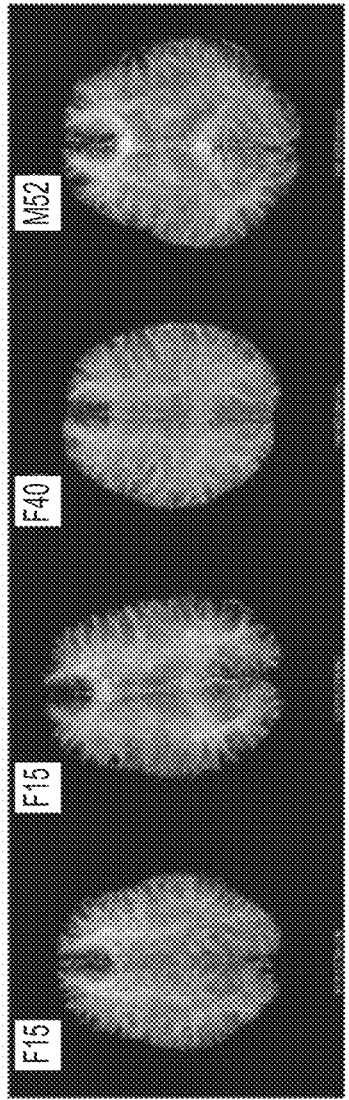

To provide evidence of spatial entropy as a valid and sensitive measure of connectome information content, we calculated the total SE of the brains of 4 subjects as a function of increasing age, specifically: two female adolescents and two healthy adults. As shown in FIG. 23, the total spatial entropies increase linearly with age, consistent with the increasing connectome complexity with brain maturation. Notably, the rate of complexity increase based on connectome skeletons (red data points) is much slower than that of the full connectome with a much higher local complexity (blue data points).

Example 9: Myelin Water Mapping

Figures 24A, 24B:
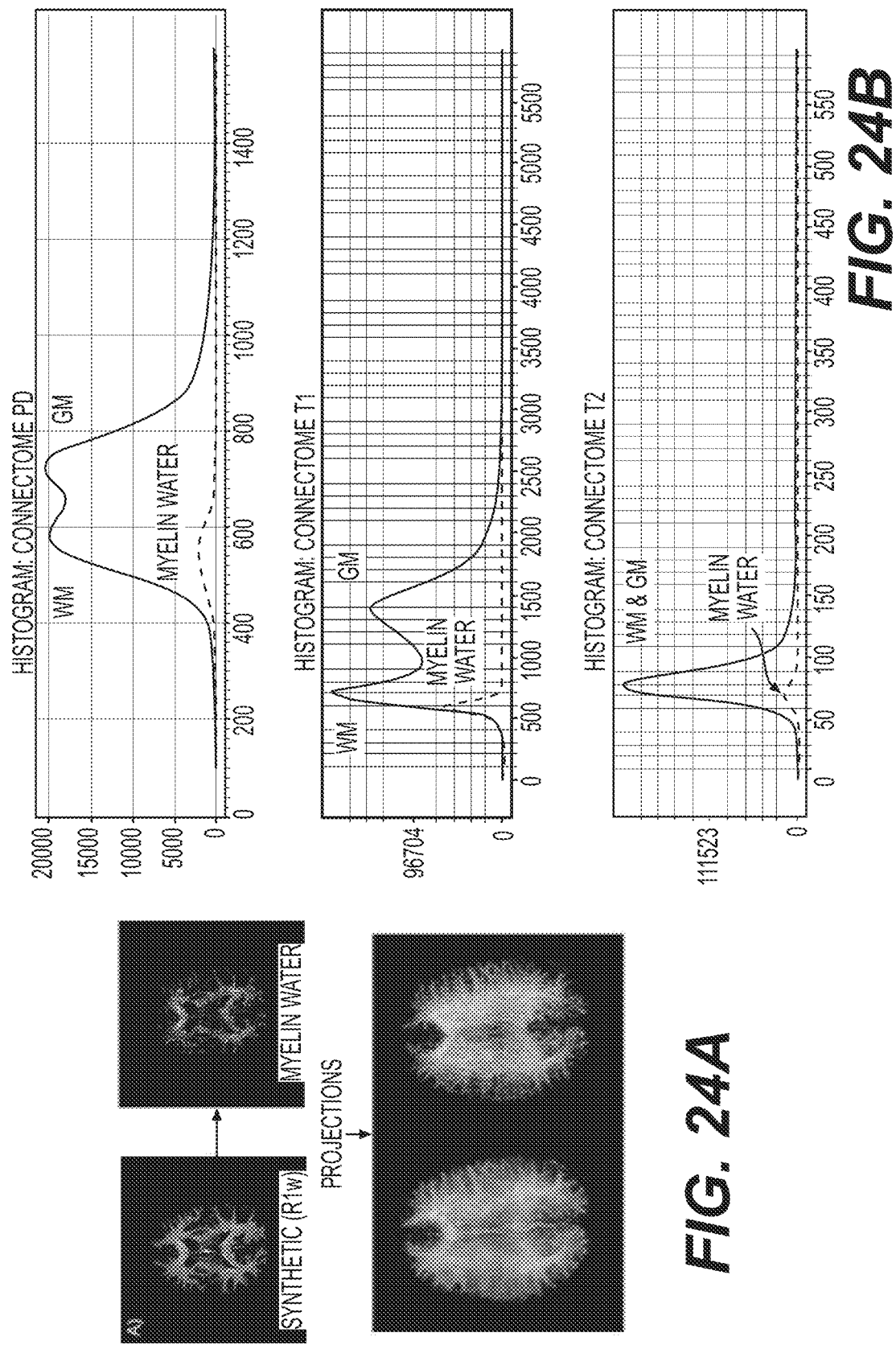
FIGS. 24A and 24B present visual mechanism of white matter fibrography. A) Heavily R1-weighted synthetic images are thresholded to isolate large signal pixels, which correlate with short T1 components of the white matter (B). Thresholding, binarization, and subsequent masking of the PD map reveals the skeleton of the axon fiber network corresponding to the water trapped within the myelin sheath. WMF connectome renderings of both representations of the fiber network demonstrate myelin water maps reveals the underlying skeleton of the synthetic rendering. B) Representative qMRI histograms of the intracranial matter (blue) and myelin water (red).

The algorithm for isolating the myelin water pixels with the methods of this disclosure is illustrated in FIG. 24. It shows that indeed the skeleton of the connectome is a reduced and version of the full connectome with fewer and thinner fibers. The associated PD, T1, and T2 histograms further support the interpretation of the connectome skeleton as consisting of the water protons with shortest T1s.

Further examples of myelin water maps are shown in FIG. 25. These maps are quantitative by construction with formula of Eq. 7, which is the product of qPD with a binary mask.

F. Discussion

1. WMF: Summary of Findings.

The examples herein demonstrate development and testing of a new and fundamentally different MRI based technique for in vivo brain connectomics termed WFM. The data show that the WMF connectome renditions are anatomically realistic and similar from subject to subject, change with age in a manner consistent with known patterns of normal brain development, can demonstrate major WM injury (ischemia) as well as reveal fiber disorganization anomalies. Such WM fiber disorder is likely associated with low measures of cognition sequelae of extreme preterm birth of the studied adolescent subject. In addition, WMF connectomes can be generated with clinically compatible scan-times using commercial configuration MRI scanners of three prominent MRI manufacturers.

WMF does not use the PFG diffusion encoding technique of Stejskal-Tanner (8) and is therefore different from dMRI-WMT at the image acquisition frontend as well as at the image processing backend. In certain embodiments of the invention, at the image acquisition frontend, the best suited pulse sequences for WMF are generally MS-qMRI variants of the fast (turbo) spin echo pulse sequence which are scan-time efficient and can achieve arguably the finest MR image quality in terms of high SNR, geometric accuracy, and high spatial resolution. Furthermore, these MS-qMRI pulse sequences are highly resilient to artifacts from magnetic field inhomogeneity and motion. These advantageous technical qualities can translate into directly acquired images of high geometrical accuracy and detail that are therefore particularly useful for unravelling the finer structural features of the connectome. At the image processing backend, WMF uses qMRI mapping algorithms and image synthesis programs that are direct and deterministic, and therefore WM fibers are observed—or detected—as opposed to created—or inferred—via mathematical modeling.

2. Validation Considerations

The data do not attempt validating WMF against dMRI-WMT because the highest quality dMRI-WMT connectome renditions may not be achievable with the commercial configuration MRI scanners and dMRI-WMT is still works-in-progress. The technical difficulties of dMRI-WMT connectomics have been analyzed in several comprehensive modern reviews (18, 20-22) and this is an active research area with continuous and encouraging improvements particularly with regards to finding an optimum balance between spatial encoding (k-space sampling) vs. diffusion encoding (q-space sampling), the so-called k-q tradeoff of dMRI-WMT (23).

The NMR origins of dMRI-WMT date back to the papers by Torrey (24) and Stejskal (25) that laid down the theoretical physics foundations and the diffusion tensor (DT) mathematical framework for the NMR description of diffusional anisotropy in complex materials and biological tissue. dMRI-WMT was made possible by incorporating diffusion encoding gradient pulses into imaging pulse sequences thus paving the road for in vivo connectomics, starting with DT imaging (26-31) WM tractography (32). The bare DT model is however rudimentary for describing the organizational complexities of WM thus stimulating the development of the so-called "higher-order" models (35-37) for dMRI-WMT connectomics. Although much progress has been made at the image processing backend of dMRI-WMT, fundamental limitations may not be solved in the near future. Thomas et al. (16) report that even with exceptional quality images generated ex vivo under ideal experimental conditions—absence of motion artifacts—and processed with the most sophisticated tractography algorithms currently available, dMRI-WMT alone is unlikely to provide an anatomically accurate rendering of the brain connectome. This work's main finding is "that a tractography technique that shows high sensitivity (a high rate of true positives) most likely will show low specificity (a high rate of false positives). In addition, the anatomical accuracy of tractography techniques was found to be highly dependent on a number of technical parameters, such as the type of diffusion model, the angular threshold, and the composition of the seed ROI" (16). It would seem therefore that the main difficulty of dMRI-WMT connectomics ultimately is to the ill-posed nature of the mathematical problem (38) in addition to the steep but conceivably surmountable technological challenges at image acquisition (7).

3. Scientific and Clinical Applications

The spectra of scientific and clinical applications of WMF and dMRI-WMT connectomics likely overlap and at the most fundamental level begin with deriving an understanding of normal brain architecture, normal brain development, and implications on cognition and behavior. WMF could be instrumental for the assessment of numerous neuropsychiatric diagnoses including Schizophrenia, Alzheimer's disease, depression, and many other conditions (see reference (12) for a more exhaustive list). The list of possible clinical applications further includes, cancer, pre-surgical planning, stroke, WM diseases, and traumatic brain injury. Perhaps the most beneficial WMF assets relate to its potential as a routine clinical tool, the full potential of which may not be estimated at this early stage of implementation and development.

The maximum spatial resolution of the directly acquired images and therefore of the connectome renditions of this report could be improved without significantly increasing scan-time by using acceleration imaging techniques such as compressed sense (39), simultaneous multislice imaging (40, 41), as well as more powerful MRI hardware (7).

4. R1-Weighted Synthetic MRI and Myelin Water

WMF technique uses R1-weighting (Eq. 1) for attenuating the intravoxel MR signals stemming from $^1$H-protonic species with lower R1 values. In all likelihood the residual high-R1 (i.e. short-T1) signals observed via WMF stem from $^1$H-protons of water or lipids of the myelin sheaths environment. Experimental evidence supporting the existence of such short-T protonic species in WM has been reported recently in the context of myelin water imaging (40, 41) and therefore, WMF by R1-weighted Synthetic MRI could be a viable technique for myelin water imaging.

Notably, the possibility of generating heavily R1-weighted images, which is straightforward with Synthetic MRI, may difficult to replicate with actual Physical MRI; physical pulse sequence cannot generate contrast weighting according to Eq. 1. It thus seem that Synthetic MRI can extend the capabilities of Physical MRI. This further highlights the need for, and the benefits of developing more efficient and powerful MS-qMRI pulse sequences as well as more sophisticated qMRI algorithms for generating accurate renditions of the "virtual patient" at the highest possible spatial resolution and image fidelity.

5. Characterizing Connectome Renditions in Terms of Fiber Organization, Order, and Complexity Via Spatial Entropy (SE) Analysis Neuroimaging research can help guide developments for neuroprotective and neurorestorative interventions (Volpe 2019) and quantitative magnetic resonance imaging (qMRI) is exceptionally fitting for minimal-risk white matter injury and gray matter disturbance investigations as it generates rich information without ionizing radiation.

The most studied qMRI parameters of the brain have been measures of water mobility by diffusion MRI (dMRI), using advanced experimental methods (Alexander, Dyrby et al. 2019, Schultz and Vilanova 2019, Sotiropoulos and Zalesky 2019) and high-level theory and tissue models (Caspers and Axer 2019, Dell'Acqua and Tournier 2019, Novikov, Fieremans et al. 2019). dMRI studies have identified WM microstructure differences between PT and term born cohorts through childhood (Nagy, Westerberg et al. 2003, Thompson, Inder et al. 2011), adolescence (Vangberg, Skranes et al. 2006, Mullen, Vohr et al. 2011) and into adulthood (Kontis, Catani et al. 2009). As noted by Dubner et al. (Dubner, Dodson et al. 2019), these microstructural differences were detected in the absence of gross WM abnormalities thus demonstrating the high sensitivity of dMRI for finding subtle pathology at the subvoxel scale.

Myelin water imaging (MWI), originally described by Mackay et al. (Mackay, Whittall et al. 1994), has served as the reference standard, non-diffusion-based technique for visualizing and quantifying the myelin content within the connectome. Myelin is a lipid-rich, layered substance that surrounds nerve cell axons in the central nervous system (CNS). While its 1H-protons are not directly detectable with clinical MRI techniques, myelin water 1H-protons that reside between the lipid layers, are both MRI detectable (T2s>10 ms) and exhibit spatial distribution that "parallels" the myelinated axonal network. Furthermore, analyses of T1 relaxometric CNS data yields myelin water associated, shortest T1 components (Labadie, Lee et al. 2013, Labadie, Lee et al. 2014, Lutti, Dick et al. 2014).

Quantifying in vivo myelin content and mapping its spatial distribution has also shown to be crucial for assessing dysmaturation. Recent studies have shown that many diseases and disorders including multiple sclerosis, neuromyelitis, neurofibromatosis, schizophrenia, autism, and stroke—for a more complete listing see—involve abnormal myelin content and/or abnormal myelin distribution patterns. Being nearly immobile, myelin 1H-protons are not directly detectable with current MRI techniques; however, myelin water 1H-protons that reside between myelin sheaths, are not only MRI detectable (T2s>10 ms) but exhibit similar spatial distribution of the myelinated axonal network.

This disclosed continuation is meant to extend the principles of white matter fibrography via Synthetic MRI from qualitative three-dimensional renditions of the connectome toward characterization and quantification. Herein, we report a computational methods (qVision) for image processing able to calculate the qMRI maps and histograms from multispectral qMRI scans. These are subsequently used to generate several anatomical segments of the central nervous system (ICM, cerebrum, cerebellum, WM, GM, and CSF). Finally, qVision represents a method for processing the qualitative heavy R1-weighted images, with optimized WM texture, to characterize the connectome rendition's fiber organization and order complexity via spatial entropy (SE) analysis. By isolating, characterizing, and quantifying myelin water, qVision assesses the spatial distribution of myelin observed in dMRI and MWI, and further applies commonly accepted properties of tissue composition in terms of hydration (PD), and MR relaxometry (T1, T2).

G. Exemplary Embodiments of Making a White Matter Fibrogram Representing the Connectome of the Brain of a Subject The following exemplary embodiments are provided for illustration only and are not intended to be limiting.

Embodiment 1. A method of making a white matter fibrogram representing the connectome of the brain of a subject, comprising: (a) performing a multispectral multi-slice magnetic resonance scan on the brain of a subject, (b) storing image data indicative of a plurality of magnetic resonance weightings of each of a plurality of slices of the brain of the subject to provide directly acquired images, (c) processing the directly acquired images to generate a plurality of quantitative maps of the brain indicative of a plurality of qMRI parameters of the subject, (d) constructing a plurality of magnetic resonance images indicative of white matter structure from the quantitative maps, and (e) rendering a white matter fibrogram of the brain of the subject from the plurality of magnetic resonance images.

Embodiment 2. The method of Embodiment 1, wherein the multispectral multislice magnetic resonance scan of (a) comprises performing a 2D scan.

Embodiment 3. The method of Embodiment 2, wherein the 2D scan is a multispectral 2D scan.

Embodiment 4. The method of Embodiment 3, wherein the multispectral 2D scan is selected from the group consisting of a 2D mixed-TSE scan, a 2D meTSEmr scan, 2D DE-TSE scan, and a 2D Tri-TSE scan.

Embodiment 5. The method of Embodiment 1, wherein the multispectral multislice magnetic resonance scan of (a) comprises performing a 3D scan.

Embodiment 6. The method of Embodiment 5, wherein the 3D scan is a multispectral 3D scan.

Embodiment 7. The method of Embodiment 6, wherein the multispectral 3D scan is selected from the group consisting of a 3D mixed-TSE scan, a 3D meTSEmr scan, a 3D DE-TSE scan, and a 3D Tri-TSE scan.

Embodiment 8. The method of any one of Embodiments 1 to 7, wherein (b) comprises storing the directly acquired images.

Embodiment 9. The method of Embodiment 8, wherein the directly acquired images are stored in a location selected from a remote computer, a dedicated workstation, a smart device (phone or tablet), and a computer cloud.

Embodiment 10. The method of any one of Embodiments 1 to 9, wherein (c) comprises processing the directly acquired images in an MRI scanner console, and/or (d) comprises processing the magnetic resonance images in an MRI scanner console, and/or (e) comprises processing the magnetic resonance images in an MRI scanner console.

Embodiment 11. The method of any one of Embodiments 1 to 9, wherein (c) comprises processing the directly acquired images in a remote computer or dedicated workstation, and/or (d) comprises processing the magnetic resonance images in a remote computer or dedicated workstation, and/or (e) comprises processing the magnetic resonance images in a remote computer or dedicated workstation.

Embodiment 12. The method of any one of Embodiments 1 to 9, wherein (c) comprises processing the directly acquired images in a smart device (phone or tablet), and/or (d) comprises processing the magnetic resonance images in a smart device (phone or tablet), and/or (e) comprises processing the magnetic resonance images in a smart device (phone or tablet).

Embodiment 13. The method of any one of Embodiments 1 to 9, wherein (c) comprises processing the directly acquired images in a server in a computer cloud, and/or (d) comprises processing the magnetic resonance images in a server in a computer cloud, and/or (e) comprises processing the magnetic resonance images in a server in a computer cloud.

Embodiment 14. The method of any one of Embodiments 1 to 13, wherein (d) comprises performing a synthetic MRI scan.

Embodiment 15. The method of Embodiment 14, wherein the synthetic MRI scan of (d) is selected from a synthetic MRI scan with quantitative R1 weighting, a synthetic MRI scan with quantitative pseudoR1 weighting, and a synthetic MRI scan with qualitative R1 weighting.

Embodiment 16. The method of any one of Embodiments 1 to 15, wherein (c) comprises processing the directly acquired images with an image sharpening filter, and/or (d) comprises processing the magnetic resonance images with an image sharpening filter, and/or (e) comprises processing the magnetic resonance images with an image sharpening filter.

Embodiment 17. The method of Embodiment 16, wherein the image sharpening filter is an unsharp mask filter or a deconvolution filter.

Embodiment 18. The method of any one of Embodiments 1 to 17, wherein (e) comprises performing a 3D to 2D projection algorithm and the white matter fibrogram of (e) is a 3D to 2D projection image.

Embodiment 19. The method of any one of Embodiments 1 to 17, wherein (e) comprises performing a 3D to 2D maximum intensity algorithm and the white matter fibrogram of (e) is a 3D to 2D maximum intensity projection.

Embodiment 20. The method of any one of Embodiments 1 to 17, wherein (e) comprises performing an algorithm selected from the group consisting of a volume rendering algorithm and a tractography algorithm.

Embodiment 21. The method of any one of Embodiments 1 to 20, wherein (c) comprises processing a plurality of directly acquired images to generate qMRI maps portraying at least one of the T1, T2, and PD distributions at the native spatial resolution of the directly acquired images.

Embodiment 22. The method of any one of Embodiments 1 to 20, wherein (c) comprises processing a plurality of directly acquired images to generate qMRI maps portraying at least one of the R1, R2, and PD distributions at the native spatial resolution of the directly acquired images.

Embodiment 23. The method of any one of Embodiments 1 to 20, wherein (c) comprises processing a plurality of directly acquired images to generate synthetic MR images weighted by R1.

Embodiment 24. The method of Embodiment 23, wherein the directly acquired images are processed with an algorithm comprising a relaxation rate weighting factor ($\Omega$) of from 0 Hz to 25 Hz.

Embodiment 25. The method of any one of Embodiments 1 to 20, wherein (c) comprises processing a plurality of directly acquired images to generate synthetic MR images weighted by pseudoR1.

Embodiment 26. The method of Embodiment 25, wherein the directly acquired images are processed with an algorithm comprising a relaxation rate weighting factor ($\Omega$) of from 0 Hz to 25 Hz.

Embodiment 27. A system configured for making a white matter fibrogram representing the connectome of the brain of a subject, comprising: i) a magnetic resonance imaging machine configured to apply an external magnetic field and a plurality of excitation pulses to a subject in the magnetic resonance imaging machine; ii) a control system connected to the magnetic resonance imaging machine and configured to perform the method of any one of Embodiments 1 to 26; and iii) a computer processor configured to receive magnetic resonance image data and render a connectome from the data.

H. Exemplary Alternative Embodiments of Making a White Matter Fibrogram Representing the Connectome of the Brain of a Subject The following exemplary alternative embodiments are provided for illustration only and are not intended to be limiting.

Alternative Embodiment 1. A method of making a white matter fibrogram representing the connectome of the brain of a subject, comprising: (a) performing a multi-slice magnetic resonance scan on the brain of a subject, (b) storing image data indicative of a plurality of magnetic resonance weightings of each of a plurality of slices of the brain of the subject to provide directly acquired images, (c) constructing a plurality of magnetic resonance images indicative of white matter structure from the data, and (d) rendering a white matter fibrogram of the brain of the subject from the plurality of magnetic resonance images.

Alternative Embodiment 2. The method of Alternative Embodiment 1, wherein (c) comprises performing a synthetic MRI scan.

Alternative Embodiment 3. The method of Alternative Embodiment 1, wherein (c) comprises performing a synthetic MRI scan with quantitative R1 weighting.

Alternative Embodiment 4. The method of anyone of Alternative Embodiments 1 to 3, wherein (c) comprises processing images with an image sharpening filter.

Alternative Embodiment 5. The method of Alternative Embodiment 4, wherein the image sharpening filter is selected from an unsharp mask filter and a convolution filter.

Alternative Embodiment 6. The method of anyone of Alternative Embodiments 1 to 5, wherein (d) comprises performing a 3D to 2D projection algorithm and the white matter fibrogram of (d) is a 3D to 2D projection image.

Alternative Embodiment 7. The method of anyone of Alternative Embodiments 1 to 5, wherein (d) comprises performing a 3D to 2D maximum intensity algorithm and the white matter fibrogram of (d) is a 3D to 2D maximum intensity projection.

Alternative Embodiment 8. The method of anyone of Alternative Embodiments 1 to 5, wherein (d) comprises performing a volume rendering algorithm.

Alternative Embodiment 9. The method of anyone of Alternative Embodiments 1 to 5, wherein (d) comprises performing a tractography algorithm.

Alternative Embodiment 10. The method of anyone of Alternative Embodiments 1 to 9, wherein the multi-slice magnetic resonance scan of (a) is performed by a method comprising: (i) applying a first excitation pulse to a first slice of the subject; (ii) detecting a first plurality of echo signals emitted by the first slice after the first excitation pulse; (iii) waiting a first period of time; (iv) applying a second excitation pulse to the first slice during partial recovery of a longitudinal magnetization of the first slice; and (v) detecting a second plurality of echo signals emitted by the first slice after the second excitation pulse.

Alternative Embodiment 11. The method of Alternative Embodiment 10, wherein detecting the first plurality of echo signals comprises obtaining an electrical response from each echo signal in the first plurality of echo signals.

Alternative Embodiment 12. The method of Alternative Embodiment 10, wherein the detected first plurality of echo signals are spin echoes, gradient echoes, or a combination of spin echoes and gradient echoes.

Alternative Embodiment 13. The method of Alternative Embodiment 10, wherein a first echo signal in the first plurality of echo signals and a first echo signal in the second plurality of echo signals are combined to form a plurality of fast spin echo readouts, a plurality of turbo spin echo readouts, or a plurality of gradient and spin echo readouts.

Alternative Embodiment 14. The method of Alternative Embodiment 10, wherein steps (i)-(iii) are applied to one or more additional slices of the subject during the first period of time.

Alternative Embodiment 15. The method of Alternative Embodiment 10, the method further comprising: (vi) waiting a second period of time; and (vii) repeating steps (i)-(v) a predetermined number of times.

Alternative Embodiment 16. The method of Alternative Embodiment 15, wherein steps (iv)-(vi) are applied to one or more additional slices of the subject during the second period of time.

Alternative Embodiment 17. The method of Alternative Embodiment 10, wherein the first excitation pulse is applied when the longitudinal magnetization of the first slice is equal to a net magnetization $M_0$.

Alternative Embodiment 18. The method of Alternative Embodiment 1, wherein the multi-slice magnetic resonance scan of (a) is performed by a method comprising use of a mixed turbo spin echo (TSE) pulse sequence.

Alternative Embodiment 19. The method of Alternative Embodiment 1, wherein the multi-slice magnetic resonance scan of (a) is performed by a method comprising use of a tri-TSE pulse sequence.

Alternative Embodiment 20. The method of anyone of Alternative Embodiments 1 to 9, wherein the multi-slice magnetic resonance scan of (A) is performed by a method comprising: (i) applying a first excitation pulse to a first slice of the subject; (ii) detecting a first set of at least three echo signals emitted by the first slice after the first excitation pulse; (iii) waiting a first period of time; (iv) repeating steps (a) through (iii) a first predetermined number of times; (v) applying a second excitation pulse to the first slice; (vi) detecting a second set of at least three echo signals emitted by the first slice after the second excitation pulse; (vii) waiting a second period of time; and (viii) repeating steps (v) through (vii) a second predetermined number of times.

Alternative Embodiment 21. The method of Alternative Embodiment 20, wherein detecting the first plurality of echo signals comprises obtaining an electrical response from each echo signal in the first plurality of echo signals.

Alternative Embodiment 22. The method of Alternative Embodiment 20, wherein the detected first plurality of echo signals are spin echoes, gradient echoes, or a combination of spin echoes and gradient echoes.

Alternative Embodiment 23. The method of Alternative Embodiment 20, wherein a first echo signal in the first plurality of echo signals and a first echo signal in the second plurality of echo signals are combined to form a plurality of fast spin echo readouts, a plurality of turbo spin echo readouts, or a plurality of gradient and spin echo readouts.

Alternative Embodiment 24. The method of Alternative Embodiment 20, wherein steps (i)-(iii) are applied to one or more additional slices of the subject during the first period of time.

Alternative Embodiment 25. The method of Alternative Embodiment 20, wherein steps (v)-(vii) are applied to one or more additional slices of the subject during the second period of time.

Alternative Embodiment 26. The method of Alternative Embodiment 20, wherein the first excitation pulse is applied when the longitudinal magnetization of the first slice is equal to a net magnetization $M_0$.

Alternative Embodiment 27. The method of any one of Alternative Embodiments 1 to 26, wherein (c) comprises processing a plurality of directly acquired images to generate qMRI maps portraying at least one of the T1, T2, and PD distributions simultaneously and with a native spatial resolution.

Alternative Embodiment 28. The method of any one of Alternative Embodiments 1 to 26, wherein (c) comprises processing a plurality of directly acquired images to generate qMRI maps portraying the relaxation rates R1, R2, and PD distributions simultaneously and with a at least the native spatial resolution of the directly acquired images.

Alternative Embodiment 29. The method of any one of Alternative Embodiments 1 to 26, wherein (c) comprises processing a plurality of directly acquired images to generate qMRI maps portraying the relaxation times T1, T2, and PD distributions simultaneously and with a at least the native spatial resolution of the directly acquired images.

Alternative Embodiment 30. The method of any one of Alternative Embodiments 1 to 29, wherein (c) comprises processing a plurality of directly acquired images to generate synthetic MR images weighted by R1.

Alternative Embodiment 31. The method of anyone of Alternative Embodiments 1 to 29, wherein (c) comprises processing images with an exponential R1-weighting image synthesis algorithm.

Alternative Embodiment 32. The method of Alternative Embodiment 30 or 31, wherein the algorithm comprises a relaxation rate weighting factor ($\Omega$) of from 0 Hz to 25 Hz.

Alternative Embodiment 33. The method of any one of Alternative Embodiments 1 to 32, wherein parts (c) and (d) are implemented in the control console of an MRI scanner.

Alternative Embodiment 34. The method of any one of Alternative Embodiments 1 to 32, wherein parts (c) and (d) are implemented in a remote workstation.

Alternative Embodiment 35. The method of any one of Alternative Embodiments 1 to 32, wherein methods in parts (c) and (d) are run in a server remotely operated by a computer.

Alternative Embodiment 36. The method of any one of Alternative Embodiments 1 to 32, wherein parts (c) and (d) are implemented in a cloud.

Alternative Embodiment 37. A system configured for making a white matter fibrogram representing the connectome of the brain of a subject, comprising: a magnetic resonance imaging machine configured to apply an external magnetic field and a plurality of excitation pulses to a subject in the magnetic resonance imaging machine; a control system connected to the magnetic resonance imaging machine and configured to perform any of the methods of any of Alternative Embodiments 1 to 36; and a computer processor configured to receive magnetic resonance image data and render a connectome from the data.

I. Exemplary Embodiments of Characterizing the Brain of a Subject

The following exemplary embodiments are provided for illustration only and are not intended to be limiting.

Embodiment 1. A method of characterizing the brain of a subject, comprising: (a) performing a multispectral multislice magnetic resonance scan on the brain of a subject, (b) storing image data indicative of a plurality of magnetic resonance weightings of each of a plurality of slices of the brain of the subject to provide directly acquired images, (c) processing the directly acquired images to generate a plurality of quantitative maps of the brain indicative of a plurality of qMRI parameters of the subject, (d) constructing a plurality of magnetic resonance images indicative of white matter structure from the quantitative maps, and (e) generating a spatial entropy map of the brain of the subject from the plurality of magnetic resonance images; and/or generating a myelin water map of the brain of the subject from the plurality of magnetic resonance images.

Embodiment 2. The method of alternative embodiment 1, wherein in e) only a spatial entropy map is generated.

Embodiment 3. The method of alternative embodiment 1, wherein in e) only a myelin water map is generated.

Embodiment 4. The method of alternative embodiment 1, wherein in e) both a spatial entropy map and a myelin water map are generated.

Embodiment 5. The method of any one of alternative embodiments 1 to 4, wherein in e) the spatial entropy map is generated using an integer disk radius of from 3 to 5 pixels.

Embodiment 6. The method of alternative embodiment 5, wherein in e) the spatial entropy map is generated using an disk radius of 4.

Embodiment 7. The method of any one of alternative embodiments 1 to 4, wherein in e) the spatial entropy map is generated using disk radius of from 3.5 to 4.5.

Embodiment 8. The method of any one of Embodiments 1 to 7, wherein the multispectral multislice magnetic resonance scan of (a) comprises performing a 2D scan.

Embodiment 9. The method of Embodiment 8, wherein the 2D scan is a multispectral 2D scan.

Embodiment 10. The method of Embodiment 9, wherein the multispectral 2D scan is selected from the group consisting of a 2D mixed-TSE scan, a 2D meTSEmr scan, 2D DE-TSE scan, and a 2D Tri-TSE scan.

Embodiment 511. The method of a any one of Embodiments 1 to 7, wherein the multispectral multislice magnetic resonance scan of (a) comprises performing a 3D scan.

Embodiment 12. The method of Embodiment 11, wherein the 3D scan is a multispectral 3D scan.

Embodiment 13. The method of Embodiment 12, wherein the multispectral 3D scan is selected from the group consisting of a 3D mixed-TSE scan, a 3D meTSEmr scan, a 3D DE-TSE scan, and a 3D Tri-TSE scan.

Embodiment 14. The method of any one of Embodiments 1 to 13, wherein (b) comprises storing the directly acquired images.

Embodiment 15. The method of Embodiment 14, wherein the directly acquired images are stored in a location selected from a remote computer, a dedicated workstation, a smart device (phone or tablet), and a computer cloud.

Embodiment 16. The method of any one of Embodiments 1 to 15, wherein (c) comprises processing the directly acquired images in an MRI scanner console, and/or (d) comprises processing the magnetic resonance images in an MRI scanner console, and/or (e) comprises processing the magnetic resonance images in an MRI scanner console.

Embodiment 7. The method of any one of Embodiments 1 to 15, wherein (c) comprises processing the directly acquired images in a remote computer or dedicated workstation, and/or (d) comprises processing the magnetic resonance images in a remote computer or dedicated workstation, and/or (e) comprises processing the magnetic resonance images in a remote computer or dedicated workstation.

Embodiment 18. The method of any one of Embodiments 1 to 15, wherein (c) comprises processing the directly acquired images in a smart device (phone or tablet), and/or (d) comprises processing the magnetic resonance images in a smart device (phone or tablet), and/or (e) comprises processing the magnetic resonance images in a smart device (phone or tablet).

Embodiment 19. The method of any one of Embodiments 1 to 15, wherein (c) comprises processing the directly acquired images in a server in a computer cloud, and/or (d) comprises processing the magnetic resonance images in a server in a computer cloud, and/or (e) comprises processing the magnetic resonance images in a server in a computer cloud.

Embodiment 20. The method of any one of Embodiments 1 to 19, wherein (d) comprises performing a synthetic MRI scan.

Embodiment 21. The method of Embodiment 20, wherein the synthetic MRI scan of (d) is selected from a synthetic MRI scan with quantitative R1 weighting, a synthetic MRI scan with quantitative pseudoR1 weighting, and a synthetic MRI scan with qualitative R1 weighting.

Embodiment 22. The method of any one of Embodiments 1 to 21, wherein (c) comprises processing the directly acquired images with an image sharpening filter, and/or (d) comprises processing the magnetic resonance images with an image sharpening filter, and/or (e) comprises processing the magnetic resonance images with an image sharpening filter.

Embodiment 23. The method of Embodiment 22, wherein the image sharpening filter is an unsharp mask filter or a deconvolution filter.

Embodiment 24. The method of any one of embodiments 1 to 23, wherein the myelin water mapping in (e) comprises thresholding R1-weighted synthetic images to isolate large signal pixels, which correlate with short T1 components of the white matter.

Embodiment 25. The method of any one of embodiments 1 to 23, wherein the myelin water mapping in (e) comprises performing thresholding, binarization, and masking of a PD map to reveal the skeleton of the axon fiber network corresponding to the water trapping within the myelin sheath.

Embodiment 26. The method of any one of Embodiments 1 to 25, wherein (e) comprises performing an algorithm selected from the group consisting of calculating anatomically localized spatial entropy measures, global spatial entropy measures, anatomically localized myelin water measures, and/or global myelin water measures.

Embodiment 27. The method of any one of Embodiments 1 to 26, wherein (c) comprises processing a plurality of directly acquired images to generate qMRI maps portraying at least one of the T1, T2, and PD distributions at the native spatial resolution of the directly acquired images.

Embodiment 28. The method of any one of Embodiments 1 to 26, wherein (c) comprises processing a plurality of directly acquired images to generate qMRI maps portraying at least one of the R1, R2, and PD distributions at the native spatial resolution of the directly acquired images.

Embodiment 29. The method of any one of Embodiments 1 to 26, wherein (c) comprises processing a plurality of directly acquired images to generate synthetic MR images weighted by R1.

Embodiment 30. The method of Embodiment 29, wherein the directly acquired images are processed with an algorithm comprising a relaxation rate weighting factor ($\Omega$) of from 0 Hz to 25 Hz.

Embodiment 31. The method of any one of Embodiments 1 to 6, wherein (c) comprises processing a plurality of directly acquired images to generate synthetic MR images weighted by pseudoR1.

Embodiment 32. The method of Embodiment 31, wherein the directly acquired images are processed with an algorithm comprising a relaxation rate weighting factor ($\Omega$) of from 0 Hz to 25 Hz.

Embodiment 33. A method of any one of Embodiments 1 to 32, further comprising determining the total spatial entropy content of the spatial entropy map of the brain of the subject.

Embodiment 34. The method of Embodiment 33, further comprising comparing the total entropy of the brain of the subject to a total entropy standard of a defined subject parameter.

Embodiment 35. The method of Embodiment 34, wherein the defined subject parameter is one or a combination of any two or more of age, gender, ethnicity, and cognitive functional on status, state of physical health, and state of mental health.

Embodiment 36. The method of Embodiment 35, wherein the total entropy measured for the subject is higher than the total entropy standard for the defined subject parameter and the subject is determined to have a condition correlated to the parameter.

Embodiment 37. The method of Embodiment 35, wherein the total entropy measured for the subject is lower than the total entropy standard for the defined subject parameter and the subject is determined to not have a condition correlated to the parameter.

Embodiment 38. A system configured for making a white matter fibrogram representing the connectome of the brain of a subject, comprising: i) a magnetic resonance imaging machine configured to apply an external magnetic field and a plurality of excitation pulses to a subject in the magnetic resonance imaging machine; ii) a control system connected to the magnetic resonance imaging machine and configured to perform the method of any one of Embodiments 1 to 37; and iii) a computer processor configured to receive magnetic resonance image data and render a connectome from the data.

J. Exemplary Alternative Embodiments of Characterizing the Brain of a Subject The following exemplary alternative embodiments are provided for illustration only and are not intended to be limiting.

Alternative Embodiment 1. A method of characterizing the brain of a subject, comprising: (a) performing a multi-slice magnetic resonance scan on the brain of a subject, (b) storing image data indicative of a plurality of magnetic resonance weightings of each of a plurality of slices of the brain of the subject to provide directly acquired images, (c) constructing a plurality of magnetic resonance images indicative of white matter structure from the data, and (d)

generating a spatial entropy map of the brain of the subject from the plurality of magnetic resonance images; and/or generating a myelin water map of the brain of the subject from the plurality of magnetic resonance images.

Alternative Embodiment 2. The method of alternative embodiment 1, wherein in d) only a spatial entropy map is generated.

Alternative Embodiment 3. The method of alternative embodiment 1, wherein in d) only a myelin water map is generated.

Alternative Embodiment 4. The method of alternative embodiment 1, wherein in d) both a spatial entropy map and a myelin water map are generated.

Alternative Embodiment 5. The method of anyone of alternative embodiments 1 to 4, wherein in d) the spatial entropy map is generated using an integer disk radius of from 3 to 5 pixels.

Alternative Embodiment 6. The method of alternative embodiment 5, wherein in d) the spatial entropy map is generated using an disk radius of 4.

Alternative Embodiment 7. The method of any one of alternative embodiments 1 to 4, wherein in d) the spatial entropy map is generated using disk radius of from 3.5 to 4.5.

Alternative Embodiment 8. The method of any one of alternative embodiments 1 to 7, wherein the myelin water mapping in (d) comprises thresholding R1-weighted synthetic images to isolate large signal pixels, which correlate with short T1 components of the white matter.

Alternative Embodiment 9. The method of any one of alternative embodiments 1 to 7, wherein the myelin water mapping in (d) comprises performing thresholding, binarization, and masking of a PD map to reveal the skeleton of the axon fiber network corresponding to the water trapping within the myelin sheath.

Alternative Embodiment 10. The method of any one of alternative embodiments 1 to 9, further comprising determining the total spatial entropy content of the brain of the subject.

Alternative Embodiment 11. The method of alternative embodiment 10, further comprising comparing the total entropy of the brain of the subject to a total entropy standard of a defined subject parameter.

Alternative Embodiment 12. The method of alternative embodiment 11, wherein the defined subject parameter is one or a combination of any two or more of age, gender, ethnicity, cognitional status, state of physical health, and state of mental health.

Alternative Embodiment 13. The method of alternative embodiment 12, wherein the total entropy measured for the subject is higher than the total entropy standard for the defined subject parameter and the subject is determined to have a condition correlated to the parameter.

Alternative Embodiment 14. The method of alternative embodiment 12, wherein the total entropy measured for the subject is lower than the total entropy standard for the defined subject parameter and the subject is determined to not have a condition correlated to the parameter.

Alternative Embodiment 15. The method of any one of Alternative Embodiments 1 to 14, wherein (c) comprises performing a synthetic MRI scan.

Alternative Embodiment 16. The method of any one of Alternative Embodiments 1 to 14, wherein (c) comprises performing a synthetic MRI scan with quantitative R1 weighting.

Alternative Embodiment 17. The method of any one of Alternative Embodiments 1 to 16, wherein (c) comprises processing images with an image sharpening filter.

Alternative Embodiment 18. The method of Alternative Embodiment 17, wherein the image sharpening filter is selected from an unsharp mask filter and a convolution filter.

Alternative Embodiment 19. The method of any one of Alternative Embodiments 1 to 18, wherein (d) comprises performing a 3D to 2D projection algorithm and the white matter fibrogram of (d) is a 3D to 2D projection image.

Alternative Embodiment 20. The method of any one of Alternative Embodiments 1 to 18, wherein (d) comprises performing a 3D to 2D maximum intensity algorithm and the white matter fibrogram of (d) is a 3D to 2D maximum intensity projection.

Alternative Embodiment 21. The method of any one of Alternative Embodiments 1 to 18, wherein (d) comprises performing a volume rendering algorithm.

Alternative Embodiment 22. The method of any one of Alternative Embodiments 1 to 19, wherein (d) comprises performing a tractography algorithm.

Alternative Embodiment 23. The method of any one of Alternative Embodiments 1 to 22, wherein the multi-slice magnetic resonance scan of (a) is performed by a method comprising: (i) applying a first excitation pulse to a first slice of the subject; (ii) detecting a first plurality of echo signals emitted by the first slice after the first excitation pulse; (iii) waiting a first period of time; (iv) applying a second excitation pulse to the first slice during partial recovery of a longitudinal magnetization of the first slice; and (v) detecting a second plurality of echo signals emitted by the first slice after the second excitation pulse.

Alternative Embodiment 24. The method of Alternative Embodiment 23, wherein detecting the first plurality of echo signals comprises obtaining an electrical response from each echo signal in the first plurality of echo signals.

Alternative Embodiment 25. The method of Alternative Embodiment 23, wherein the detected first plurality of echo signals are spin echoes, gradient echoes, or a combination of spin echoes and gradient echoes.

Alternative Embodiment 26. The method of Alternative Embodiment 23, wherein a first echo signal in the first plurality of echo signals and a first echo signal in the second plurality of echo signals are combined to form a plurality of fast spin echo readouts, a plurality of turbo spin echo readouts, or a plurality of gradient and spin echo readouts.

Alternative Embodiment 27. The method of Alternative Embodiment 23, wherein steps (i)-(iii) are applied to one or more additional slices of the subject during the first period of time.

Alternative Embodiment 28. The method of Alternative Embodiment 23, the method further comprising: (vi) waiting a second period of time; and (vii) repeating steps (i)-(v) a predetermined number of times.

Alternative Embodiment 29. The method of Alternative Embodiment 28, wherein steps (iv)-(vi) are applied to one or more additional slices of the subject during the second period of time.

Alternative Embodiment 30. The method of Alternative Embodiment 23, wherein the first excitation pulse is applied when the longitudinal magnetization of the first slice is equal to a net magnetization $M_0$.

Alternative Embodiment 31. The method of any one of Alternative Embodiments 1 to 14, wherein the multi-slice magnetic resonance scan of (a) is performed by a method comprising use of a mixed turbo spin echo (TSE) pulse sequence.

Alternative Embodiment 32. The method of any one of Alternative Embodiments 1 to 14, wherein the multi-slice magnetic resonance scan of (a) is performed by a method comprising use of a tri-TSE pulse sequence.

Alternative Embodiment 33. The method of any one of Alternative Embodiments 1 to 22, wherein the multi-slice magnetic resonance scan of (A) is performed by a method comprising: (i) applying a first excitation pulse to a first slice of the subject; (ii) detecting a first set of at least three echo signals emitted by the first slice after the first excitation pulse; (iii) waiting a first period of time; (iv) repeating steps (a) through (iii) a first predetermined number of times; (v) applying a second excitation pulse to the first slice; (vi) detecting a second set of at least three echo signals emitted by the first slice after the second excitation pulse; (vii) waiting a second period of time; and (viii) repeating steps (v) through (vii) a second predetermined number of times.

Alternative Embodiment 34. The method of Alternative Embodiment 33, wherein detecting the first plurality of echo signals comprises obtaining an electrical response from each echo signal in the first plurality of echo signals.

Alternative Embodiment 35. The method of Alternative Embodiment 33, wherein the detected first plurality of echo signals are spin echoes, gradient echoes, or a combination of spin echoes and gradient echoes.

Alternative Embodiment 36. The method of Alternative Embodiment 33, wherein a first echo signal in the first plurality of echo signals and a first echo signal in the second plurality of echo signals are combined to form a plurality of fast spin echo readouts, a plurality of turbo spin echo readouts, or a plurality of gradient and spin echo readouts.

Alternative Embodiment 37. The method of Alternative Embodiment 33, wherein steps (i)-(iii) are applied to one or more additional slices of the subject during the first period of time.

Alternative Embodiment 38. The method of Alternative Embodiment 33, wherein steps (v)-(vii) are applied to one or more additional slices of the subject during the second period of time.

Alternative Embodiment 39. The method of Alternative Embodiment 33, wherein the first excitation pulse is applied when the longitudinal magnetization of the first slice is equal to a net magnetization $M_0$.

Alternative Embodiment 40. The method of any one of Alternative Embodiments 1 to 39, wherein (c) comprises processing a plurality of directly acquired images to generate qMRI maps portraying at least one of the T1, T2, and PD distributions simultaneously and with a native spatial resolution.

Alternative Embodiment 41. The method of any one of Alternative Embodiments 1 to 39, wherein (c) comprises processing a plurality of directly acquired images to generate qMRI maps portraying the relaxation rates R1, R2, and PD distributions simultaneously and with a at least the native spatial resolution of the directly acquired images.

Alternative Embodiment 42. The method of any one of Alternative Embodiments 1 to 39, wherein (c) comprises processing a plurality of directly acquired images to generate qMRI maps portraying the relaxation times T1, T2, and PD distributions simultaneously and with a at least the native spatial resolution of the directly acquired images.

Alternative Embodiment 43. The method of any one of Alternative Embodiments 1 to 42, wherein (c) comprises processing a plurality of directly acquired images to generate synthetic MR images weighted by R1.

Alternative Embodiment 44. The method of any one of Alternative Embodiments 1 to 42, wherein (c) comprises processing images with an exponential R1-weighting image synthesis algorithm.

Alternative Embodiment 45. The method of Alternative Embodiment 43 or 44, wherein the algorithm comprises a relaxation rate weighting factor ($\Omega$) of from 0 Hz to 25 Hz.

Alternative Embodiment 46. The method of any one of Alternative Embodiments 1 to 45, wherein parts (c) and (d) are implemented in the control console of an MRI scanner.

Alternative Embodiment 47. The method of any one of Alternative Embodiments 1 to 45, wherein parts (c) and (d) are implemented in a remote workstation.

Alternative Embodiment 48. The method of any one of Alternative Embodiments 1 to 45, wherein methods in parts (c) and (d) are run in a server remotely operated by a computer.

Alternative Embodiment 49. The method of any one of Alternative Embodiments 1 to 45, wherein parts (c) and (d) are implemented in a cloud.

Alternative Embodiment 50. A system configured for making a white matter fibrogram representing the connectome of the brain of a subject, comprising: a magnetic resonance imaging machine configured to apply an external magnetic field and a plurality of excitation pulses to a subject in the magnetic resonance imaging machine; a control system connected to the magnetic resonance imaging machine and configured to perform any of the methods of any of Alternative Embodiments 1 to 49; and a computer processor configured to receive magnetic resonance image data and render a connectome from the data.

K. Conclusion

WMF is a promising complementary alternative to dMRI-WMT for studying the microarchitecture of white matter, which can generate undistorted high spatial resolution connectomes in clinically feasible (<10 min) scan times using standard clinical MRI hardware. This work could have implications for the assessment of WM disease, traumatic brain injury, and for improving preoperative surgical planning, and building ultrahigh spatial resolution connectomes.

It is to be understood that while various illustrative implementations have been described, the forgoing description is merely illustrative and does not limit the scope of the invention. While several examples have been provided in the present disclosure, it should be understood that the disclosed systems, components and methods may be embodied in many other specific forms without departing from the scope of the present disclosure.

The examples disclosed can be implemented in combinations or sub-combinations with one or more other features described herein. A variety of apparatus, systems and methods may be implemented based on the disclosure and still fall within the scope of the invention. Also, the various features described or illustrated above may be combined or integrated in other systems or certain features may be omitted, or not implemented.

While various embodiments and alternative embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure.

REFERENCES

1. Sporns O, Tononi G, & Kötter R (2005) The human connectome: a structural description of the human brain. *PLOS Computational Biology* 1(4):e42.
2. Sotiropoulos S N & Zalesky A (2017) Building connectomes using diffusion MRI: why, how and but. *NMR in Biomedicine*:n/a-n/a.
3. Swanson L W & Lichtman J W (2016) From Cajal to connectome and beyond. *Annual Review of Neuroscience* 39(1):197-216.
4. Craddock R C, et al. (2013) Imaging human connectomes at the macroscale. *Nat Meth* 10(6):524-539.
5. Van Essen D C, et al. (2012) The Human Connectome Project: A data acquisition perspective. *NeuroImage* 62(4):2222-2231.
6. Assaf Y, et al. (2013) The CONNECT project: combining macro- and micro-structure. *NeuroImage* 80:273-282.
7. McNab J A, et al. (2013) The Human Connectome project and beyond: Initial applications of 300 mT/m gradients. *NeuroImage* 80:234-245.
8. Stejskal E & Tanner J (1965) Spin diffusion measurements: spin echoes in the presence of a time-dependent field gradient. *Journal of Chemical Physics*, Vol. 42:288-292.
9. Le Bihan D & Breton E (1985) Imagerie de diffusion in vivo par résonance magnétique nucléaire. In vivo magnetic resonance imaging of diffusion. *CR Acad Sci Paris* 301(15):1109-1112.
10. Merboldt K D, Hanicke W, & Frahm J (1985) Self-diffusion NMR imaging using stimulated echoes. *Journal of Magnetic Resonance* 64(3):479-486.
11. Taylor D & Bushell M (1985) The spatial mapping of translational diffusion coefficients by the NMR imaging technique. *Physics in Medicine and Biology* 30:345.
12. Wandell B A (2016) Clarifying human white matter. *Annual Review of Neuroscience* 39(1):103-128.
13. Riederer S J, et al. (1984) Automated MR image synthesis: feasibility studies. *Radiology* 153(1):203-206.
14. Fatouros P, Marmarou A. Use of magnetic resonance imaging for in vivo measurements of water content in human brain: method and normal values. Journal of neurosurgery. 1999; 90(1):109.
15. Jara H., Sakai O, Mankal P, Irving R P, Norbash A M. Multispectral quantitative magnetic resonance imaging of brain iron stores: a theoretical perspective. Top Magn Reson Imaging. 2006; 17(1):19-30.
16. Thomas C, et al. (2014) Anatomical accuracy of brain connections derived from diffusion MRI tractography is inherently limited. *Proceedings of the National Academy of Sciences* 111(46):16574-16579.
17. Shawna Farquharson, et al. (2013) White matter fiber tractography: why we need to move beyond DTI. *Journal of neurosurgery* 118(6):1367-1377.
18. Jones D K, Knösche T R, & Turner R (2013) White matter integrity, fiber count, and other fallacies: The do's and don'ts of diffusion MRI. *Neuroimage* 73:239-254.
19. O'Muircheartaigh J, et al. (2014) White matter development and early cognition in babies and toddlers. *Human Brain Mapping* 35(9):4475-4487.
20. Jones D K & Cercignani M (2010) Twenty-five pitfalls in the analysis of diffusion MRI data. *NMR in Biomedicine* 23(7):803-820.
21. Le Bihan D & Johansen-Berg H (2012) Diffusion MRI at 25: exploring brain tissue structure and function. *NeuroImage* 61(2):324-341.
22. O'Donnell L J & Pasternak O (2015) Does diffusion MRI tell us anything about the white matter? An overview of methods and pitfalls. *Schizophrenia Research* 161(1):133-141.
23. Fan Q, et al. (2017) HIgh b-value and High Resolution Integrated Diffusion (HIBRID) imaging. *NeuroImage* 150:162-176.
24. Torrey H (1956) Bloch equations with diffusion terms. *Physical Review*, vol. 104 (3):563-565.
25. Stejskal E (1965) Use of spin echoes in a pulsed magnetic-field gradient to study anisotropic restricted diffusion and flow. *Journal of Chemical Physics*, Vol. 43:3597-3603.
26. Basser P J, Mattiello J, & LeBihan D (1994) Estimation of the effective self-diffusion tensor from the NMR spin echo. *J Magn Reson B* 103(3):247-254.
27. Basser P J, Mattiello J, & LeBihan D (1994) MR diffusion tensor spectroscopy and imaging. *Biophys J* 66(1):259-267.
28. Basser P J & Pierpaoli C (1996) Microstructural and physiological features of tissues elucidated by quantitative-diffusion-tensor MRI. *J Magn Reson B* 111(3):209-219.
29. Pierpaoli C & Basser P J (1996) Toward a quantitative assessment of diffusion anisotropy. *Magn Reson Med* 36(6):893-906.
30. Pierpaoli C, Jezzard P, Basser P J, Barnett A, & Di Chiro G (1996) Diffusion tensor MR imaging of the human brain. *Radiology* 201(3):637-648.
31. Mattiello J, Basser P J, & Le Bihan D (1997) The b matrix in diffusion tensor echo-planar imaging. *Magn Reson Med* 37(2):292-300.
32. Basser P J, Pajevic S, Pierpaoli C, Duda J, & Aldroubi A (2000) In vivo fiber tractography using DT-MRI data. *Magnetic Resonance in Medicine* 44(4):625-632.
33. Tuch D S, et al. (2002) High angular resolution diffusion imaging reveals intravoxel white matter fiber heterogeneity. *Magnetic Resonance in Medicine* 48(4):577-582.
34. Tuch D S (2004) Q-ball imaging. *Magnetic Resonance in Medicine* 52(6):1358-1372.
35. Alexander D C (2005) Multiple-fiber reconstruction algorithms for diffusion MRI. *Annals of the New York Academy of Sciences* 1064(1):113-133.
36. Behrens T E, Berg H J, Jbabdi S, Rushworth M F, & Woolrich M W (2007) Probabilistic diffusion tractography with multiple fibre orientations: What can we gain? *Neuroimage* 34(1):144-155.
37. Jeurissen B, Leemans A, Jones D K, Tournier J D, & Sijbers J (2011) Probabilistic fiber tracking using the residual bootstrap with constrained spherical deconvolution. *Human brain mapping* 32(3):461-479.
38. Mangin J F, et al. (2013) Toward global tractography. *NeuroImage* 80 (Supplement C):290-296.
39. Feng L, et al. (2017) Compressed sensing for body MRI. *Journal of Magnetic Resonance Imaging* 45(4):966-987.
40. Barth M, Breuer F, Koopmans P J, Norris D G, & Poser B A (2016) Simultaneous multislice (SMS) imaging techniques. *Magnetic Resonance in Medicine* 75(1):63-81.
41. Gagoski B A, et al. (2015) RARE/turbo spin echo imaging with simultaneous multislice Wave-CAIPI. *Magnetic Resonance in Medicine* 73(3):929-938.
42. MacKay A L & Laule C (2016) Magnetic resonance of myelin water: an in vivo marker for myelin. *Brain Plasticity* 2(1):71-91.

43. Labadie C, et al. (2014) Myelin water mapping by spatially regularized longitudinal relaxographic imaging at high magnetic fields. *Magnetic Resonance in Medicine* 71(1):375-387.
44. O'Shea T M, et al. (2009) The ELGAN study of the brain and related disorders in extremely low gestational age newborns. *Early Human Development* 85(11):719-725.
45. Elliot C (2007) Differential Ability Scales-II (DAS-II) San Antonio. *TX Pearson.*
46. Joseph R M, et al. (2016) Neurocognitive and academic outcomes at age 10 years of extremely preterm newborns. *Pediatrics* 137(4).
47. Jara H (2013) *Theory of quantitative magnetic resonance imaging* (World Scientific Publishing Co. Pte. Ltd., Singapore).
48. Schindelin J, et al. (2012) Fiji: an open-source platform for biological-image analysis. *Nature methods* 9(7):676.
49. Alexander, D. C., et al. (2019). "Imaging brain microstructure with diffusion MRI: practicality and applications." *NMR in Biomedicine* 32(4): e3841.
50. Caspers, S. and M. Axer (2019). "Decoding the microstructural correlate of diffusion MRI." *NMR in Biomedicine* 32(4): e3779.
51. Celik, T. (2014). "Spatial Entropy-Based Global and Local Image Contrast Enhancement." *IEEE Transactions on Image Processing* 23(12): 5298-5308.
52. Dell'Acqua, F. and J.-D. Tournier (2019). "Modelling white matter with spherical deconvolution: How and why?" *NMR in Biomedicine* 32(4): e3945.
53. Dubner, S. E., et al. (2019). "White matter microstructure and cognitive outcomes in relation to neonatal inflammation in 6-year-old children born preterm." *NeuroImage: Clinical* 23:101832.
53. Jara, H. (2020). White matter fibrography by synthetic magnetic resonance imaging. https://patents.google.com/patent/US20190365273A1/en, USPTO.
54. Kontis, D., et al. (2009). "Diffusion tensor MRI of the corpus callosum and cognitive function in adults born preterm." *Neuroreport* 20(4): 424-428.
55. Labadie, C., et al. (2013). "Myelin water mapping by spatially regularized longitudinal relaxographic imaging at high magnetic fields." *Magnetic Resonance in Medicine*: n/a-n/a.
56. Labadie, C., et al. (2014). "Myelin water mapping by spatially regularized longitudinal relaxographic imaging at high magnetic fields." *Magnetic Resonance in Medicine* 71(1):375-387.
57. Lutti, A., et al. (2014). "Using high-resolution quantitative mapping of R1 as an index of cortical myelination." *Neuroimage* 93: 176-188.
58. Mackay, A., et al. (1994). "In vivo visualization of myelin water in brain by magnetic resonance." *Magnetic Resonance in Medicine* 31(6): 673-677.
59. Mullen, K. M., et al. (2011). "Preterm birth results in alterations in neural connectivity at age 16 years." *Neuroimage* 54(4): 2563-2570.
60. Nagy, Z., et al. (2003). "Preterm Children Have Disturbances of White Matter at 11 Years of Age as Shown by Diffusion Tensor Imaging." *Pediatric Research* 54(5): 672-679.
61. Novikov, D. S., et al. (2019). "Quantifying brain microstructure with diffusion MRI: Theory and parameter estimation." *NMR in Biomedicine* 32(4): e3998.
62. Schultz, T. and A. Vilanova (2019). "Diffusion MRI visualization." *NMR in Biomedicine* 32(4): e3902.
63. Sotiropoulos, S. N. and A. Zalesky (2019). "Building connectomes using diffusion MRI: why, how and but." *NMR in Biomedicine* 32(4): e3752.
64. Thompson, D. K., et al. (2011). "Characterization of the corpus callosum in very preterm and full-term infants utilizing MRI." *Neuroimage* 55(2): 479-490.
65. van der Walt, S., et al. (2014). "scikit-image: image processing in Python." *PeerJ* 2: e453.
66. Vangberg, T. R., et al. (2006). "Changes in white matter diffusion anisotropy in adolescents born prematurely." *Neuroimage* 32(4): 1538-1548.
67. Volpe, J. J. (2019). "Dysmaturation of Premature Brain: Importance, Cellular Mechanisms, and Potential Interventions." *Pediatric Neurology* 95: 42-66.

What is claimed is:

1. A method of characterizing the brain of a subject, comprising:
    (a) performing a multispectral multislice magnetic resonance scan on the brain of a subject,
    (b) storing image data indicative of a plurality of magnetic resonance weightings of each of a plurality of slices of the brain of the subject to provide directly acquired images,
    (c) processing the directly acquired images to generate a plurality of quantitative maps of the brain indicative of a plurality of qMRI parameters of the subject,
    (d) constructing a plurality of magnetic resonance images indicative of white matter structure from the quantitative maps, and
    (e) generating a spatial entropy map of the brain of the subject from the plurality of magnetic resonance images; and/or generating a myelin water map of the brain of the subject from the plurality of magnetic resonance images.

2. The method of claim 1, wherein in e) only a spatial entropy map is generated.

3. The method of claim 1, wherein in e) only a myelin water map is generated.

4. The method of claim 1, wherein in e) both a spatial entropy map and a myelin water map are generated.

5. The method of claim 1, wherein in e) the spatial entropy map is generated using an integer disk radius of from 3 to 5 pixels.

6. The method of claim 5, wherein in e) the spatial entropy map is generated using a disk radius of 4.

7. The method of claim 1, wherein in e) the spatial entropy map is generated using disk radius of from 3.5 to 4.5.

8. The method of claim 1, wherein the multispectral multislice magnetic resonance scan of (a) comprises performing a 2D scan.

9. The method of claim 1, wherein the multispectral multislice magnetic resonance scan of (a) comprises performing a 3D scan.

10. The method of claim 1, wherein (b) comprises storing the directly acquired images.

11. The method of claim 1, wherein (d) comprises performing a synthetic MRI scan.

12. The method of claim 1, wherein the myelin water mapping in (e) comprises thresholding R1-weighted synthetic images to isolate large signal pixels, which correlate with short T1 components of the white matter.

13. The method of claim 1, wherein the myelin water mapping in (e) comprises performing thresholding, binarization, and masking of a PD map to reveal the skeleton of the axon fiber network corresponding to the water trapping within the myelin sheath.

14. The method of claim 1, wherein (e) comprises performing an algorithm selected from the group consisting of calculating anatomically localized spatial entropy measures, global spatial entropy measures, anatomically localized myelin water measures, and/or global myelin water measures.

15. A method of claim 1, further comprising determining the total spatial entropy content of the brain of the subject.

16. The method of claim 15, further comprising comparing the total entropy of the brain of the subject to a total entropy standard of a defined subject parameter.

17. The method of claim 16, wherein the defined subject parameter is one or a combination of any two or more of age, gender, ethnicity, cognition status, state of physical health, and state of mental health.

18. The method of claim 17, wherein the total entropy measured for the subject is higher than the total entropy standard for the defined subject parameter and the subject is determined to have a condition correlated to the parameter.

19. The method of claim 17, wherein the total entropy measured for the subject is lower than the total entropy standard for the defined subject parameter and the subject is determined to not have a condition correlated to the parameter.

* * * * *